(12) United States Patent
Messmer et al.

(10) Patent No.: US 9,745,364 B2
(45) Date of Patent: Aug. 29, 2017

(54) METHODS AND COMPOSITIONS FOR DIAGNOSIS AND TREATMENT OF B CELL CHRONIC LYMPHOCYTIC LEUKEMIA

(75) Inventors: Bradley T. Messmer, La Jolla, CA (US); Nicholas Chiorazzi, Tenafly, NJ (US); Emilia Albesiano, Baltimore, MD (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 13/354,774

(22) Filed: Jan. 20, 2012

(65) Prior Publication Data

US 2012/0141462 A1 Jun. 7, 2012

Related U.S. Application Data

(63) Continuation of application No. 10/575,671, filed as application No. PCT/US2004/033176 on Oct. 8, 2004, now Pat. No. 8,119,340.

(60) Provisional application No. 60/509,473, filed on Oct. 8, 2003.

(51) Int. Cl.
*C07K 16/00* (2006.01)
*G01N 33/68* (2006.01)

(52) U.S. Cl.
CPC ......... *C07K 16/00* (2013.01); *G01N 33/6878* (2013.01)

(58) Field of Classification Search
None
See application file for complete search history.

(56) References Cited

U.S. PATENT DOCUMENTS 5,693,762 A * 12/1997 Queen et al. ............... 530/387.3
7,371,383 B2 * 5/2008 Reed et al. ................. 424/145.1
2009/0117095 A1 5/2009 Messmer

OTHER PUBLICATIONS

Miller et al (J Rheumatol, 1996, 23(12): Abstract).*
Pugh-Bernard et al (J Clin Invest, 2001, 108: 1061-1070).*
Potter et al (J Exp Med, 1993, 178: 14-19-1428).*
Sasaki et al (J Clin Invest, 1988, 82(3): 748-754).*
Communicataion pursuant to Article 94(3) EPC regarding Application No. 04 7954 503.5, dated Mar. 1, 2012.
Preliminary Notice of Reasons for Rejection regarding Japanese Patent Application No. 2006-534362, dated Dec. 14, 2011, including English translation.
Borche, L, et al., "Evidence That Chronic Lymphocytic Leukemia B Lymphocytes Are Frequently Committed to Production of Natural Autoantibodies," Blood, 1990, vol. 76, pp. 562-589.
Brezinscheck, H-P, et al, "Analysis of the Human VH Gene Repertoire. Differential Effects of Selection and somatic Hypermutation on Human Peripherals CD5+/IgM+," The Journal of Clinical Investigation, 1997, vol. 99, No. 10, pp. 2488-2501.
Chiorazzi, N. and Ferrarini, M., "Immunoglobulin Variable Region Gene Characteristics and Surface Membrane Phenotype Define B-CLL Subgroups with Distinct Clinical Courses," Chronic Lymphoid Leukemias, 2001, B.D. Cheson, editor, Marcel Dekker, NY, pp. 81-9109.
Damle, R.N., et al., "Ig V Gene Mutation Status and CD38 Expression As Novel Prognostic indicators in Chronic Lymphocytic Leukemia," Blood, 1999, vol. 94, No. 6, pp. 1840-1847.
Fais, F., et al., "Chronic Lymphocytic Leukemia B Cells Express Restricted Sets of Mutated and Unmutates Antigen Receptors," The Journal of Clinical Investigation, 1998, vol. 102, No. 8, pp. 1515-1525.
Ghia, P., "Monoclonal CD5+ and CD5-B-lymphocyte expansions are frequent in the peripheral blood of the elderly," Blood, 2004, vol. 103, No. 6, pp. 2337-2342.
Ghiotto, F., et al., "Remarkably similar antigen receptors among a subset of patients with chronic lymphocytic leukemia," The Journal of Clinical Investigation, 2004, vol. 113, No. 7, pp. 1006-1016.
Hamblin, T.J., et al., "Unmutated IG VH Genes Are Associated With a More Aggressive Form of Chronic Lymphocytic Leukemia," Blood, 1999, vol. 94, No. 6, pp. 1848-1854.
He, X., et al., "VH3-21 B Cells Escape from a State of Tolerance in Rheumatoid Arthritis and Secrete Rheumatoid Factor," Molecular Medicine, 1995, vol. 1, No. 7, pp. 766-780.
Isaacson, P.G., "Gastric MALT lymphoma: From concept to cure," Annals of Oncology, 1999, vol. 10, pp. 637-645.
Johnson, T.A., "IG VH1 genes expressed in B cell chronic lymphocytic leukemia exhibit distinctive molecular 'features,'" The Journal of Immunology, 1997, vol. 158, No. 1, pp. 235-246.
Kirkham, P.M., et al., "Immunoglobulin VH clan and family identity predicts variable domain structure and may influence antigen binding," The EMBO Journal, 1992, vol. 11, No. 2, pp. 603-609.
Kumar, S., et al., "Anti cardiolipin/B-2 glycoprotein activities co-exist on human anti-DNA antibody light chains," Molecular Immunology, 2003, vol. 40, No. 8, pp. 517-530.
Pascual, V., et al. "VH Restriction Among Human Cold Agglutinins, The Vh4-21 Gene Segment is Required to Encode Anti-I and Anti-i Specificites," The Journal of Immunology, vol. 149, No. 7, pp. 2337-2344.
Potter, M., "Antigen-Binding Myeloma Proteins of Mice," Advances In Immunology, 1977, vol. 25, pp. 141-211.
Pugh-Bernard, A.E., et al., "Regulation of inherently autoreactive VH4-34 B cells in the maintenance of human B cell tolerance," The Journal of Clinical Investigation, vol. 108, No. 7, pp. 1061-1070.
Rawstron, A.C., et al., "Monoclonal B lymphocytes withe the characteristics of 'Indolent' chronic lymphocytic leukemia are present in 3.5% of adults with normal blood counts," Blood, 2002, vol. 100, No. 2, pp. 635-639.

(Continued)

*Primary Examiner* — Sean Aeder
(74) *Attorney, Agent, or Firm* — Amster, Rothstein & Ebenstein LLP

(57) ABSTRACT

This invention provides an anti-idiotype antibody that binds to the antigen-binding region of an antibody encoded by antibody genes selected from the group consisting of Set I, Set II, Set III, Set IV, Set V, Set VIa, Set VIb, Set VIc, Set VId, Set VIe, Set VII, and Set VIII, hybridomas and methods of treatments using such.

11 Claims, 16 Drawing Sheets

(56) References Cited

OTHER PUBLICATIONS

Schroder, Jr., H.W. and Dighiero, G., "The pathogenesis of chronic lymphocytic leukemia: analysis of the antibody repertoire," Immunology Today, 1994, vol. 15, No. 6, pp. 288-294.
Scott, M.G., et al., "Clonal Charactgerization of the Human IgG Antibody Repertoire to Haemophilus influenzae Type b Polysaccharide. III. A single VKII Gene and One of Several JK Genes Aer Joined by an Invariant Arginine to Form the Most Common L Chain V Region," The Journal of Immunology, 1988, vol. 143, No. 12, pp. 4110-4116.
Silverman, G.J., et al, "Idiotpic and Subgroup analysis of Human Monoclonal Rheumatoid Factors, Implication for Structural and Genetic Basis of Autoantibodies in Humans," The Journal of Clinical Investigation, 1998, vol. 82, pp. 469-475.
Sthoeger, A.M., et al., "Mechanism of Autoimmune Hermolytic Anemia in Chronic Lymphocytic Leukemia," American Journal of Hematology, 1993, vol. 43, pp. 259-264.
Tobin, G., et al., "Somatically mutated Ig VH3-21 genes characterize a new subset of chronic lymphocytic leukemia," Blood, 2002, vol. 99, No. 6, pp. 2262-2264.
Tobin, G., et al., "Chronic lymphocytic leukemias utilizing the VH-3-21 gene display highly restricted VA-14 gene use and homologues CDR3s: implicating recognition of a common antigen epitope," Blood, 2003, vol. 101, No. 12, pp. 4952-4957.
Valetto, A., et al., "A Subset of IgG+ B-CLL Cells Expresses Virtually Identical Antigen that Bind Similar Peptides. Evidence for Antigen-Selection in the Leukemogenic Process," Abstract #1784, Poster Board#/Session: 456-III (cited incorrectly in International Search Report of PCT/US2004/033176).
Carter P., "Improving the Efficacy of Antibody-Based Cancer Therapies," Nature Reviews, Cancer, Nov. 2001, vol. 1, No. 2, pp. 118-129.
Supplementary European Search Report issued Mar. 20, 2008 in connection with European Patent Application No. EP 04794503.5.
Jul. 14, 2005 Written Opinion and International Search Report issued in connection with PCT International Patent Application No. PCT/US2004/033176.
Apr. 10, 2006 International Preliminary Report on Patentability issued in connection with PCT International Patent Application No. PCT/US2004/033176.
The International Search Report for PCT Application No. PCT/US2004/033176.
The Written Opinion of the Internatinal Searching Authority for PCT Application No. PCT/US2004/033176.
The International Preliminary Report on Patentability for PCT Application No. PCT/US2004/033176.
The Office Action for corresponding European Application No. 04 794 503.5, dated Feb. 2, 2010.
The Office Action for corresponding European Application No. 04 794 503.5, dated Apr. 9, 2008.
Valetto, et al., "Chronic Lymphoid Leukemia," Bio. and Clin. Invest. III, Abstract #1784, p. 431a.
Fais, et al., "Chronic Lymphocytic Leukemia B Cells Express Restricted Sets of Mutated and Unmutated Antigen Receptors," J. Clin. Invest., 1998, vol. 102, pp. 1515-1525.
Damle, et al., "Ig V Gene Mutation Status and CD38 Expression as Novel Prognostic Indicators in Chronic Lymphocytic Leukemia," Blood, Sep. 15, vol. 94, pp. 1840-1847.
Chiorazzi, et al., "Immunoglobulin Variable Region Gene Characteristics and Surface Membrane Phenotype Define B-CLL subgroups with Distinct Clinical Courses."
Chronic Lymphoid Leukemia, Marcel Dekker, New York, NY, US (2001), pp. 81-109.
Ghiotto, et al. "Remarkable Similar Antigen Receptors Among a Subset of Patients with Chronic Lynphocytic Leukemia," J. of Clin. Invest., vol. 113:7, pp. 1008-1011.
Carter, "Improving the Efficacy of Antibody-Based Cancer Therapies," Nature Reviews (2001), vol. 1, pp. 119-129.
Chiorazzi, et al., "B Cell Chronic Lymphocytic Leukemia: Lessons Learned from Studies of the B Cell Antigen Receptor," Annu. Rev. Immunol., 2005, 21:841-894.
Valetto, et al., Blood, 92(10) suppl. 1 part 1-2, abstract# 1784, p. 431A.
Fais, et al., J. Clin. Invest., 1998, 102(8): 1515-1525.
Damie, et al., Blood, 1999, 94(6): 1840-1847.
Office Action issued Nov. 17, 2011 in corresponding Canadian Application No. 2,541,360.

* cited by examiner

FIG. 1-1

Set I.

| $V_H4-39$ | | | | | | | | D6-13 | | | | | | | | | | | | $J_H5$ | | | | |
|---|---|---|---|---|---|---|---|---|---|---|---|---|---|---|---|---|---|---|---|---|---|---|---|---|
| C | A | R | H/Q | | | | | G | Y | S | S | S | W | Y | | | | | | N | W | F | D | |
| TGT | GCG | AGA | CA | | | | | GGG | TAT | AGC | AGC | AGC | TGG | TAC | | | | | | AAC | TGG | TTC | GAC | |
| C | A | S | R | | | | | G | Y | S | S | S | W | W | - | - | S | S | | N | W | F | D | CLL039 |
| TGT | GCG | AGC | AGA | | | | | GGG | TAT | AGC | AGC | AGC | TGG | TGG | - | - | TCA | TCT | | AAC | TGG | TTC | GAC | |
| C | A | R | H | L | | | | G | Y | S | S | S | W | Y | - | - | A | A | | N | W | F | D | CLL057 |
| TGT | GCG | AGA | CAT | CTG | | | | GGA | TAT | AGC | AGC | AGC | TGG | TAC | - | - | GCA | GCA | | AAC | TGG | TTC | GAC | |
| C | A | R | R | F | | | | G | Y | S | S | S | W | Y | - | G | - | G | | D | W | F | D | CLL114 |
| TGT | GCG | AGA | CGG | TTC | | | | GGG | TAT | AGC | AGC | AGC | TGG | TAC | - | GGG | - | GGG | | GAC | TGG | TTC | GAC | |
| C | A | R | S | T | | | | G | Y | S | S | S | W | Y | - | - | L | L | | N | W | F | D | CLL202 |
| TGT | GCG | AGA | AGG | ACC | | | | GGG | TAT | AGC | AGC | AGC | TGG | TAC | - | - | TTA | TTA | | AAT | TGG | TTC | GAC | |
| C | A | R | Q | A | | | | G | A | S | S | S | W | Y | - | S | W | R | | N | W | F | D | CLL209 |
| TGT | GCG | AGA | CAA | GCT | | | | GGG | GCT | AGC | AGC | AGC | TGG | TAC | - | TCT | TGG | CGC | | AAC | TGG | TTC | GAC | |
| C | A | R | H | E | | | | G | Y | S | S | S | W | Y | G | P | S | S | | N | W | F | D | Y09249 immunocytoma |
| TGT | GCG | AGA | CAT | GAG | | | | GGG | TAT | AGC | AGC | AGC | TGG | TAC | GGC | CCC | TCC | TCC | | AAC | TGG | TTC | GAC | |
| | | | | | | | | | | | | | | | - | R | S | S | | D | W | F | D | |
| | | | | | | | | | | | | | | | - | AGG | AGC | AGC | | GAC | TGG | TTC | GAC | |

FIG. 1-2

Set II.

```
         VH 4-34                           D5-5                                  JH6
    C  A   R   G               V   D   T   A   M   V           Y   Y   Y   Y
    TGT GCG AGA GG            GTG GAT ACA GCT ATG GTT    AT    TAC TAC TAC TAT

C  A   R   G   Y          G   D   T   P   T   I     R     Y   Y
    TGT GCG AGA GGA TAC        GGG GAT ACA CCT ACC ATT   AGA   TAC TAT                  CLL183
    C  A   R   G   Y          A   D   T   P   V   F     R     Y   Y
    TGT GCG AGA GGA TAT        GCA GAT ACA CCT GTG TTT   CGG   TAC TAC                  CLL240
    C  A   R   G   W          G   D   T   P   M   L     K     Y   Y
    TGT GCG AGA GGC TGG        GGG GAT ACT CCT ATG CTT   AAA   CGC TAC                  CLL342
    C  A   R   A   Y          P   D   T   P   M   V     R     Y   Y
    TGT GCG AGA GCA TAC        CCG GAT ACA CCT ATG GTC   AGG   TAC TAC      AF087422    CLL 4B [1]
    C  A   R   G   F          P   D   T   I   D   V     K     Y   Y
    TGT GCG AGA GGC TTC        CCG GAT ACA CCT ATT GTG   AAG   CGC TAC      AJ239333    CLL ID 47 [2]
```

FIG. 1-3

Set VIa.

```
       VH1-02         D6-19                                    JH4
    C  A  R    D/E                                          Y  F  D  Y
    TGT GCG AGA GA                                      AC TAC TTT GAC TAC
              V   .    Q   W   L   V
              GG  TAG  CAG TGG CTG GTA C
    C  A  R    E    Q   W   L   L   E   H   Y  F  D  Y
    TGT GCG AGG GAG CAG TGG CTG CTT GAG CAC TAC TTT GAC TAC   CLL011
       A  R    V
    C  A  R    E    Q   W   L   L   R        Y  F  D  Y
    TGT GCG AGA GTG CAG TGG CTG GTA TTA AGA  --- CAC TTT GAC TAC   CLL270
       A  R    E    Q   W   L   G   A
    C  A  R    E    Q   W   L   G   A   E    Y  F  D  Y
    TGT GCG AGA GAC CAG TGG CTG GGC GCA GAA --- AAC TTT GAC TAC   CLL266
       A  R    E
    C  A  R    E    Q   W   L   V   L   K    N  F  D  Y
    TGT GCG AGA GAG CAG TGG CTG GGC CTG AAA  --- AAC TTT GAC TAC   CLL340
       A  R    V
    C  A  R    V    Q   W   L   L   L   E    R  F  D  Y
    TGT GCG AGA GTT CAG TGG TTA CTC GAA --- CGA TTT GAC TAC   AJ239371   CLL 3       2
       A  R    N    Q   W   L   G        D  Y  F  D  Y
    C  A  R    N
    TGT GCG AGA AAC CAG TGG CTG GGT CTC --- GAC TAC TTT GAC TAC   AJ487492   SMZL Tierens,A.M. U3
       A  R    E    Q   W   L   V   R    T       S  F  D  Y
    C  A  R
    TGT GCG AGA GAG CAG TGG CTG GTA CTG AGG ACG --- AGC TTT GAC TAC   U86787     CLL-H2B  1   U0
```

FIG. 1-4

Set VIb,c,d

| V$_H$1-03 | | | D6-19 | | | | | | | | | J$_H$4 | | | | | |
|---|---|---|---|---|---|---|---|---|---|---|---|---|---|---|---|---|---|
| C | A | R | D/E | | | | | | | | | Y | F | D | Y | | |
| TGT | GCG | AGA | GA | | | | | | | | | AC | TAC | TTT | GAC | TAC | |
| | | | | V | | Q | W | L | V | L | S | - | - | Y | F | D | Y |
| C | A | R | V | | | Q | W | L | V | | | | | | | | |
| TGT | GCG | AGG | GTA | TAG | CAG | TGG | CTG | GTA | C | CTA | TCT | - - - | TAC | TTT | GAC | TAC | CLL336 |
| C | A | R | E | | | Q | W | L | V | L | - | N | Y | F | D | Y | |
| TGT | GCG | AGG | GAG | | | CAG | TGG | CTG | GTC | CTT | - | AAC | TAC | TTT | GAC | TAC | CLL360 |
| C | A | R | E | | | Q | W | L | V | A | L | - | P | F | D | Y | |
| TGT | GCG | AGG | GAG | | | CAG | TGG | CTG | GTA | GCC | CTA | - - - | CCC | TTT | GAC | TAC | AF376961 LAN Digheiro |
| C | A | K | E | | | Q | W | L | V | A | I | V | N | Y | F | D | Y |
| TGT | GCG | AAG | GAG | | | CAG | TGG | CTG | GCC | A | TTA | AAA | AAC | TAC | TTT | GAC | TAC | L01278 CLL-412 [3] |
| C | A | R | E | | | Q | W | L | G | L | P | - | T | Y | F | D | Y |
| TGT | GCG | AGA | GAG | | | CAG | TGG | CTG | GGT | GCC | ATC | CCT | - - - | ACC | TTT | GAC | TAC | U86801 [4] U3/1 |
| C | A | R | V | | | Q | W | L | G | L | T | G | P | N | F | D | Y |
| TGT | GCG | AGA | GTT | | | CAG | TGG | CTG | GGC | CTA | CCT | ACG | CCG | AAT | TTT | GAC | TAC | U84176 KEM (VH1-46) [5] U0 |
| C | A | R | G | | | Q | W | L | V | I | L | - | N | F | D | Y | |
| TGT | GCT | AGG | GGA | | | CAG | TGG | CTG | GGC | ACG | CTA | - - - | AAC | TTT | GAC | TAC | U84162 BYR (VH1-46) [5] U0 |
| C | A | R | D | | | Q | W | L | V | I | T | - | N | F | D | Y | |
| TGT | GCG | AGG | GAT | | | CAG | TGG | CTG | GTC | ATC | CTA | - - - | AAC | AAC | TTT | GAC | TAC | AF376953 Digheiro PIQ U2 |
| C | A | R | E | | | Q | W | L | V | L | - | - | H | F | D | Y | |
| TGT | GCG | AGA | GAG | | | CAG | TGG | CTG | CCC | ACG | - | - - - | - | CAC | TTT | GAC | TAC | |
| C | A | R | E | | | Q | W | L | V | L | S | - | - | F | D | Y | |
| TGT | GCG | AGG | GAG | | | CAG | TTG | GTA | CTA | TCT | - - - | CAC | TTT | GAC | TAC | | CLL154 (VH1-18) |

FIG. 1-5

Set IV.

| | $V_H$1-69 | | | | | | | D3-16 | | | | | | | | $J_H$3 | | | | |
|---|---|---|---|---|---|---|---|---|---|---|---|---|---|---|---|---|---|---|---|---|
| | C | A | R | D/E | | | | | | | | | | | | | | | | |
| | TGT | GCG | AGA | GA | | | | | | | | | | | | | | | | |
| | | | | | Y | Y | D | Y | V | W | G | S | Y | R | Y | T | D | A | F | D | I |
| | | | | | TAT | TAT | GAT | TAC | GTT | TGG | GGG | AGT | TAT | CGT | TAT | ACC | GAT | GCT | TTT | GAT | GTC |
| C | A | R | G | | G | D | Y | Y | V | W | G | S | Y | R | S | N | D | A | F | D | I | CLL068 |
| TGT | GCG | AGA | GGA | | GGC | GAT | TAT | TAC | GTT | TGG | GGG | AGT | TAT | CGT | TCT | AAT | GAT | GCT | TTT | GAT | ATC | |
| C | A | R | G | | G | I | Y | D | V | W | G | S | Y | R | P | N | D | A | F | D | I | CLL258 |
| TGT | GCG | AGA | GGG | | GGT | ATT | TAT | GAT | GTT | TGG | GGG | AGT | TAT | CGT | CCG | AAT | GAT | GCT | TTT | GAT | ATC | |
| C | A | R | G | | G | N | Y | D | I | W | G | S | Y | R | S | N | D | A | F | D | I | AAC51720 CLL SMI[5] |
| TGT | GCG | AGA | GGG | | GGC | AAT | TAT | GAT | ATT | TGG | GGG | AGT | TAT | CGT | TCC | AAT | GAT | GCT | TTT | GAT | ATC | |
| C | A | R | G | | G | D | Y | D | V | W | G | S | Y | R | P | N | D | A | F | D | I | AJ414008 CLL 022 Russia |
| TGT | GCG | AGA | GGG | | GGG | GAT | TAT | GAT | GTT | TGG | GGG | AGT | TAT | CGT | CCG | AAT | GAT | GCT | TTT | GAT | ATC | |
| C | A | R | G | | G | N | Y | D | I | W | G | S | Y | R | S | N | D | A | F | D | I | AF460965 α-cardiolipin Martin, France |
| TGT | GCG | AGA | GGA | | GGC | AAT | TAT | GAT | ATT | TGG | GGG | AGT | TAT | CGT | TCC | AAT | GAT | GCT | TTT | GAT | ATC | |

FIG. 1-6

Set V.

| | V$_H$1-69 | | | | | | D3-10 | | | | | | | J$_H$5 | | | | |
|---|---|---|---|---|---|---|---|---|---|---|---|---|---|---|---|---|---|---|
| | C | A | R | D/E | | | | | | | | | | Y | Y | | | |
| | TGT | GCG | AGA | GA | | | | | | | | AT | TAC | TAC | TAC | | | |
| | | | | GT | ATT | ACT | ATG | GTT | CGG | GGA | GTT | ATT | ATA | AC | | | | |
| | | | | | I | T | M | V | R | G | V | I | I | | | | | |
| | C | A | E | G | | | M | V | Q | G | V | I | G | I | Y | Y | | |
| TGT | GCG | GAG | GGT | | | ATG | GTT | CAG | GGA | GTT | ATT | GGA | ATT | TAC | TAC | AJ389179 | GN12 $^8$ |
| | C | A | R | S | | | M | V | Q | G | V | I | N | Y | L | Y | | |
| TGT | GCG | AGG | TCT | | | ATG | GTT | CAG | GGA | GTT | ATT | AAC | GTC | TAC | CTC | TAC | AAC51697 | FUH $^5$ |
| | C | A | R | A | | | M | V | R | G | V | I | H | L | D | Y | | |
| TGT | GCG | AGG | GCT | | | ATG | GTT | CGG | GGA | GTT | ATT | CAC | TTG | GAC | TAC | AJ239372 | ID64 $^2$ |
| | C | A | R | V | | | M | V | R | G | V | I | S | L | D | Y | | |
| TGT | GCG | AGA | GTT | | | ATG | GTT | CGG | GGA | GTT | ATT | TCC | CTG | GAC | TAC | AF376959 | SIN Digheiro U0 |

FIG. 1-7

Set III.

```
        V_H3-21                           J_H6
         C    A    R   E/D                 Y   Y   Y   M   D   V   W   G
         TGT  GCG  AGA GA                AT TAC TAC TAC ATG GAC GTC TGG GGC

C   A   R   D   A   Y   G   M   D   V   W   G
TGT GCG AGA GAT GCG AAT GGA ATG GAC GTC TGG GGC   CLL282
 C   A   R   D   R   N   G   M   D   V   W   G
TGT GCG AGA GAT CGG AAC GGT ATG GAC GTC TGG GGC   CLL175
 C   A   R   D   Q   N   G   M   D   V   W   G
TGT GCG AGA GAT CAA AAC GGT ATG GAC GTC TGG GGC   CLL412
 C   A   S   D   R   N   G   M   D   V   W   G
TGT GCG AGC GAT CGA AAC GGT ATG GAC GTC TGG GGC   AJ239379   ID28      [2]
 C   A   R   E   P   Y   G   M   D   V   W   G
TGT GCG AGA GAG CCA TAC GGT ATG GAC GTC TGG GGC   AF174100   sc77u-16  [9]
 C   A   R   D   G   S   G   M   D   V   W   G
TGT GCG AGA GAT GGC TCC GGT ATG GAC GTC TGG GGC   AJ389178   GN11      [8]
 C   A   R   D   A   N   G   M   D   V   W   G
TGT GCG AGA GAT GCT AAC GGC ATG GAC GTC TGG GGC   AF299104   IF case 10 [10] U3
```

FIG. 1-8

Set VIe

| | V$_H$5-51 | | | D6-19 | | | | | | | | J$_H$4 | | | | | | |
|---|---|---|---|---|---|---|---|---|---|---|---|---|---|---|---|---|---|---|
| | C | A | R | Q/H | | | | | | | | Y | F | D | Y | | | |
| | TGT | GCG | AGA | CA | | | | | | | | AC | TAC | TTT | GAC | TAC | | |

| | | | | | | | | | | | | | | | | | |
|---|---|---|---|---|---|---|---|---|---|---|---|---|---|---|---|---|---|
| | | | V | . | Q | W | L | V | | | | | | | | | |
| | GG | GTA | TAG | CAG | TGG | CTG | GTA | C | | | | | | | | | |

| C | A | R | Q | Q | W | L | G | G | D | Y | F | D | Y | | CLL026 | | |
|---|---|---|---|---|---|---|---|---|---|---|---|---|---|---|---|---|---|
| TGT | GCG | AGG | CAG | TGG | CTG | GGT | GGC | GAC | TAC | TTT | GAC | TAC | | | | | |

| C | A | R | R | Q | W | L | A | L | G | H | F | D | Y | AF099198 | Tre [11] 012/0-2 JK2 |
|---|---|---|---|---|---|---|---|---|---|---|---|---|---|---|---|
| TGT | GCG | AGA | AGG | CAG | TGG | CTG | GCC | CTA | GGC | CAC | TTT | GAC | TAC | | |

| C | A | R | Q | Q | W | F | G | V | Y | Y | F | D | Y | AJ414007 | CLL021 Russia U0 |
|---|---|---|---|---|---|---|---|---|---|---|---|---|---|---|---|
| TGT | GCG | AGA | CAG | CAG | TGG | TTC | GGC | GTG | TAC | TAC | TTT | GAC | TAC | | |

| C | A | R | Q | Q | W | L | V | L | P | Y | F | D | Y | AJ239373 | ID38 [2] |
|---|---|---|---|---|---|---|---|---|---|---|---|---|---|---|---|
| TGT | GCG | AGA | CAA | CAG | TGG | CTG | GTA | CTT | CCA | TAC | TTT | GAC | TAC | | |

| C | A | R | Q | Q | W | L | I | V | T | H | F | D | Y | AJ555263 | GO14 |
|---|---|---|---|---|---|---|---|---|---|---|---|---|---|---|---|
| TGT | GCG | AGA | CAG | CAG | TGG | CTG | GTA | GTA | ACT | CAC | TTT | GAC | TAC | | |

| C | A | R | E | Q | W | L | V | L | D | Y | F | D | Y | AJ272398 | AG [12] |
|---|---|---|---|---|---|---|---|---|---|---|---|---|---|---|---|
| TGT | GCG | AGA | GAG | CAG | TGG | CTC | ATA | GTA | GAC | TAC | TTT | GAC | TAC | | |

| C | A | R | Q | Q | W | L | V | L | S | N | F | D | Y | PH1562 | HOW [13] |
|---|---|---|---|---|---|---|---|---|---|---|---|---|---|---|---|
| TGT | GCG | AGA | CAG | CAG | TGG | CTG | GTG | TTG | GAC | TAC | TTT | GAC | TAC | | |

| C | A | R | E | Q | W | L | V | L | | | | | | Not available | |

FIG. 1 - 9

```
      V_H1-02       D6-19                                    J_H4
   C   A   R   D/E                                         F   D   Y
  TGT GCG AGA GA                                          AC TTT GAC TAC
               V   .   Q   W   L   V
              GG GTA TAG CAG TGG CTG GTA C

C   A   R   E   Q   W   L   V   L   E   H   Y   F   D   Y
  TGT GCG AGG GAC CAG TGG CTG GTA CTT GAG CAC TAC TTT GAC TAC   CLL011
   C   A   R   V   Q   W   L   G   L   R   -   H   F   D   Y
  TGT GCG AGA GTG CAG TGG CTG GGC TTA AGA --- CAC TTT GAC TAC   CLL270
   C   A   R   E   Q   W   L   G   A   E   -   N   F   D   Y
  TGT GCG AGA GAG CAG TGG CTG GGC GCA GAA --- AAC TTT GAC TAC   CLL266
   C   A   R   E   Q   W   L   V   L   K   -   N   F   D   Y
  TGT GCG AGG GAG CAG TGG CTG GTA CTG AAA --- AAC TTT GAC TAC   CLL340
   C   A   R   V   Q   W   L   L   L   E   -   R   F   D   Y
  TGT GCG AGA GTT CAG TGG TTA TTA CTC GAA --- CGA TTT GAC TAC   AJ239371   CLL 3   [2]
   C   A   R   N   Q   W   L   G   L   D   -   Y   F   D   Y
  TGT GCG AGA AAC CAG TGG CTG GGT CTC GAC --- TAC TTT GAC TAC   AJ487492   SMZL Tierens,A.M.
   C   A   R   E   Q   W   L   V   R   T   -   S   F   D   Y
  TGT GCG AGA GAG CAG TGG CTG GTA AGG ACG --- AGC TTT GAC TAC   U86787     CLL-H2B [1] U0
   C   A   R   E   Q   W   L   V   L   S   -   Y   F   D   Y
  TGT GCG AGG GAG CAG TGG CTG GTC CTA TCT --- TAC TTT GAC TAC   CLL336
   C   A   R   E   Q   W   L   V   L   -   N   Y   F   D   Y
  TGT GCG AGG GAG CAG TGG CTG GTA CTT --- AAC TAC TTT GAC TAC   CLL360
   C   A   R   E   Q   W   L   A   L   K   -   P   F   D   Y
  TGT GCG AGA GAG CAG TGG CTG GCC TTA AAA --- CCC TTT GAC TAC   AF376961   LAN Digheiro
   C   A   R   K   Q   W   L   A   I   V   N   Y   F   D   Y
  TGT GCG AGA AAG CAG TGG CTG GCC ATC GTC AAC TAC TTT GAC TAC   L01278     CLL-412 [3]
   C   A   R   E   Q   W   L   G   L   P   -   T   F   D   Y
  TGT GCG AGA GAG CAG TGG CTG GGT CTA CCT --- ACC TTT GAC TAC   U86801 [4] U3/1
   C   A   R   V   Q   W   L   G   L   T   G   P   N   D   Y
  TGT GCT AGG GTT CAG TGG CTG GGC CTG ACG GGG CCG AAT GAC TAC   U84176     KEM (VH1-46) [5] U0
   C   A   R   G   Q   W   L   V   I   L   -   N   F   D   Y
  TGT GCG AGG GGA CAG TGG CTG GTC ATC CTA --- AAC TTT GAC TAC   U84162     BYR (VH1-46) [5] U0
   C   A   R   D   Q   W   L   P   T   -   N   N   F   D   Y
  TGT GCG AGA GAT CAG TGG CTG CCC ACG --- AAC AAC TTT GAC TAC   AF376953   Digheiro PIQ U2
   C   A   R   E   Q   W   L   V   L   S   -   H   F   D   Y
  TGT GCG AGG GAG CAG TGG TTG GTA CTA TCT --- CAC TTT GAC TAC   CLL154     (VH1-18)
   C   A   R   Q   Q   W   L   G   G       D   Y   F   D   Y
  TGT GCG AGG CAG CAG TGG CTG GGT GGC     GAC TAC TTT GAC TAC   CLL026
   C   A   R   R   Q   W   L   A   L       G   H   F   D   Y
  TGT GCG AGA AGG CAG TGG CTG GCC CTA     GGC CAC TTT GAC TAC   AF099198   Tre [11] O12/0-2
  JK2
   C   A   R   Q   Q   W   F   G   V       Y   Y   F   D   Y
  TGT GCG AGA CAG CAA TGG TTC GGC GTG     TAC TAC TTT GAC TAC   AJ414007   CLL021 Russia U0
   C   A   R   Q   Q   W   L   V   L       P   Y   F   D   Y
  TGT GCG AGA CAG CAG TGG CTG GTA CTT     CCA TAC TTT GAC TAC   AJ239373   ID38 [2]
   C   A   R   E   Q   W   L   I   V       T   H   F   D   Y
  TGT GCG AGA GAG CAG TGG CTC ATA GTA     ACT CAC TTT GAC TAC   AJ555263   GO14
   C   A   R   Q   Q   W   L   V   L       D   Y   F   D   Y
  TGT GCG AGA CAG CAG TGG CTG GTG TTG     GAC TAC TTT GAC TAC   AJ272398   AG [12]
   C   A   R   E   Q   W   L   V   L                   S   N   F   D   Y
  TGT GCG AGA CAG CAG TGG CTG GTG TTG        Not available       PH1562    HOW [13]
```

| V_H1-69 | | | | D3-16 | | | | | | | | | | | J_H3 | | | | | V_K A27 | | | | | | | | J_K1/4*/5# |
|---|---|---|---|---|---|---|---|---|---|---|---|---|---|---|---|---|---|---|---|---|---|---|---|---|---|---|---|---|
| C | A | R | D/E | Y | Y | D | Y | V | W | G | S | Y | R | Y | D | A | F | D | I | Q | Q | Y | G | S | S | P | P | W T F G |
| tgt gcg aga ga | | | | g tat gat tac gtt tgg ggg agt tat cgt tat acc | | | | | | | | | | | t gat gct ttt gat atc | | | | | cag cag tat ggt agc tca cct cc | | | | | | | | g tgg acg ttc ggc |
| . | . | . | . | . | . | G | G | D | . | . | . | . | . | . | . | . | . | . | . | S | N | . | . | . | . | . | . | CLL068 |
| . | . | . | g. | . | . | G | G | I | . | . | . | . | . | . | . | . | . | . | . | .c .a. | | . | . | . | . | . | . | CLL258 ... G |
| .gg ggt at. | | | | . | . | G | G | I | . | . | . | . | . | . | . | . | . | . | . | P | N | ccg . | . | . | . | . | MF9 ... g. |
| . | . | . | . | . | . | G | G | P | . | . | . | . | . | . | . | . | . | . | . | P | N | . | . | . | . | . | . | SMI ... G |
| .ga ggg cc. | | | | . | . | G | G | N | . | . | I | . | . | . | . | . | . | . | . | S | N | cc .a | | . | . | . | . | CLL022 (natural Ab producing clone) |
| . | . | . | . | . | . | G | G | D | . | . | . | . | . | . | . | . | . | . | . | P | N | . | . | . | . | . | . | α-cardiolipin ... g. |
| .gg gg. g. | | | | . | . | G | G | N | . | . | I | . | . | . | . | . | . | . | . | S | N | ccg .a | | . | . | . | . | ... P |
| .ga ggc a. | | | | . | . | G | G | N | . | . | . | . | . | . | . | . | . | . | . | . | . | cc .a | | . | . | . | . | ... g ..# |
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 1 | 2 | 3 | 4 | 5 | 6 | 7 8 9 10 11 |

| V$_H$1-69 | | D2-2 | | J$_H$6 | | V$_K$L6 | | | J$_K$3 |
|---|---|---|---|---|---|---|---|---|---|
| C A R D/E | | D I V V V P A A I | | Y Y Y | | Q Q R S N W P P | | | |
| tgt gcg aga ga | | ag gat att gta gta gta cca gct ata cc | | at tac tac tac | | Cag cag cgt agc aac tgg cct cc | | | |
| | | | | | | | | F T F G P G | |
| | | | | | | | | a ttc act ttc ggc cct | ggg |

| | 1 | 2 | 3 | 4 | 5 | 6 | 7 | 8 | 9 | 10 | 11 | 12 | 13 | 14 | 15 | 16 | 17 | 18 | | | 1 | 2 | 3 | 4 | 5 | 6 | 7 | 8 | 9 | 10 |
|---|---|---|---|---|---|---|---|---|---|---|---|---|---|---|---|---|---|---|---|---|---|---|---|---|---|---|---|---|---|---|
| FS41 | . | . | . | G | G | . | . | . | . | . | . | . | . | . | . | M | S | . | | | | | | | | | | | | |
| UCA4 | . | . | . | G | A | . | . | . | . | . | . | . | . | .g t.c | . | M | G | . | | | | | | | | | | | | |
| GO13 | . | . | . | G | G | . | .gc gg. | . | . | . | . | . | .g .ga | . | . | M | R | . | | | . | . | . | . | . | . | G | . | . | . |

METHODS AND COMPOSITIONS FOR DIAGNOSIS AND TREATMENT OF B CELL CHRONIC LYMPHOCYTIC LEUKEMIA

CROSS-REFERENCE TO RELATED APPLICATION

This application is a continuation of U.S. Ser. No. 10/575,671, now U.S. Pat. No. 8,119,340 a U.S. National Phase of PCT Application No. PCT/US2004/033176, filed Oct. 8, 2004, now allowed, which claims the benefit of U.S. Provisional Application No. 60/509,473, filed Oct. 8, 2003.

The ".txt" Sequence Listing filed by EFS and which is entitled 50425_400_ST25.txt, is 123 kilobytes in size and which was created on Dec. 22, 2011 is hereby incorporated by reference.

STATEMENT REGARDING FEDERALLY FUNDED RESEARCH OR DEVELOPMENT

The invention was made with government support under grant numbers CA081554 and CA087956 awarded by the National Institutes of Health. The government has certain rights in the invention.

BACKGROUND

The present invention generally relates to methods of diagnosis and treatment of B cell chronic lymphocytic leukemia (B-CLL). More particularly, the invention relates to methods of B-CLL diagnosis and treatment based on the presence of sets of B-CLL patients that have B cell receptor genes in common.

DESCRIPTION OF THE RELATED ART

References Cited

Bendelac, A., M. Bonneville, and J. F. Kearney. Autoreactivity by design: innate B and T lymphocytes. Nat Rev Immunol. 2001:1:177-186.

Borche L et al. Blood 1990; 76:562-569.

Brezinschek H P, Foster S J, Brezinschek R I, Dorner T, Domiati-Saad R, Lipsky P E. Analysis of the human VH gene repertoire. Differential effects of selection and somatic hypermutation on human peripheral CD5(+)/IgM+ and CD5(−)/IgM+ B cells. J Clin Invest. 1997; 99:2488-2501.

Broker B M et al. J Autoimmun 1988; 1:469-481.

Casali P, Schettino E W. Structure and function of natural antibodies. Current Topics in Microbiology & Immunology. 1996; 210:167-179.

Chapman C J, Spellerberg M B, Smith G A, Carter S J, Hamblin T J, Stevenson F K. Autoanti-red cell antibodies synthesized by patients with infectious mononucleosis utilize the VH4-21 gene segment. Journal of Immunology 1993; 151:1051-1061.

Chiorazzi, N., and M. Ferrarini. Immunoglobulin Variable Region Gene Characteristics and Surface Membrane Phenotype Define B-CLL Subgroups with Distinct Clinical Courses. In Chronic Lymphoid Leukemias. B. D. Cheson, editor. Marcel Dekker, New York. 2001; 81-109.

Chiorazzi, N., and M. Ferrarini. B Cell Chronic Lymphocytic Leukemia: Lessons Learned from Studies of the B Cell Antigen Receptor. In Annual Review of Immunology. W. E. Paul, editor. 2003; 21:841-894.

Damle, R. N., T. Wasil, F. Fais, F. Ghiotto, A. Valetto, S. L. Allen, A. Buchbinder, D. Budman, K. Dittmar, J. Kolitz, S. M. Lichtman, P. Schulman, V. P. Vinciguerra, K. R. Rai, M. Ferrarini, and N. Chiorazzi. Ig V gene mutation status and CD38 expression as novel prognostic indicators in chronic lymphocytic leukemia. Blood. 1999; 94:1840-1847.

Fais F, Ghiotto F, Hashimoto S, Sellars B, Valetto A, Allen S L, Schulman P, Vinciguerra V P, Rai K, Rassenti L Z, Kipps T J, Dighiero G, Schroeder H W, Jr., Ferrarini M, Chiorazzi N. Chronic lymphocytic leukemia B cells express restricted sets of mutated and unmutated antigen receptors. J Clin Invest. 1998; 102:1515-1525.

Fais, F., G. Gaidano, D. Capello, A. Gloghini, F. Ghiotto, S. Roncella, A. Carbone, N. Chiorazzi, and M. Ferrarini. Immunoglobulin V region gene use and structure suggest antigen selection in AIDS-related primary effusion lymphomas. Leukemia 1999; 13:1093-1099.

Geiger, K. D., U. Klein, A. Brauninger, S. Berger, K. Leder, K. Rajewsky, M. L. Hansmann, and R. Kuppers. CD5-positive B cells in healthy elderly humans are a polyclonal B cell population. Eur J Immunol. 2000; 30:2918-2923.

Ghia, P., G. Prato, C. Scielzo, S. Stella, M. Geuna, G. Guida, and F. Caligaris-Cappio. Monoclonal CD5+ and CD5-B-lymphocyte expansions are frequent in the peripheral blood of the elderly. Blood. 2004; 103:2337-2342.

Ghiotto, F., F. Fais, A. Valetto, E. Albesiano, S. Hashimoto, M. Dono, H. Ikematsu, S. L. Allen, K. R. Rai, M. Nardini, A. Tramontano, M. Ferrarini, and N. Chiorazzi. Remarkable similar antigen receptors among a subset of patients with chronic lymphocytic leukemia. J Clin Invest. 2004; 113:1008-1016.

Hamblin, T. J., Z. Davis, A. Gardiner, D. G. Oscier, and F. K. Stevenson. Unmutated Ig V(H) genes are associated with a more aggressive form of chronic lymphocytic leukemia. Blood. 1999; 94:1848-1854.

Hashimoto, S., M. Wakai, J. Silver, and N. Chiorazzi. Ann. NY. Acad. Sci. 1992; 651:477-479.

He X, Goronzy J J, Zhong W, Xie C, Weyand C M. VH3-21 B cells escape from a state of tolerance in rheumatoid arthritis and secrete rheumatoid factor. Mol Med. 1995; 1:768-780.

Isaacson, P. G. Gastric MALT lymphoma: from concept to cure. Ann Oncol. 1999; 10:637-645.

Jahn S, Schwab J, Hansen A, Heider H, Schroeder C, Lukowsky A, Achtman M, Matthes H, Kiessig S T, Volk H D. Human hybridomas derived from CD5+ B lymphocytes of patients with chronic lymphocytic leukemia (B-CLL) produce multi-specific natural IgM (kappa) antibodies. Clin Exp Immunol. 1991; 83:413-417.

Johnson T A, Rassenti L Z, Kipps T J. Ig VH1 genes expressed in B cell chronic lymphocytic leukemia exhibit distinctive molecular features. J Immunol. 1997; 158:235-246.

Kirkham, P. M., F. Mortari, J. A. Newton, and H. W. Schroeder, Jr. EMBO. J. 1997; 11:603-609.

Kipps T J, Tomhave E, Pratt L F, Duffy S, Chen P P, Carson D A. Developmentally restricted immunoglobulin heavy chain variable region gene expressed at high frequency in chronic lymphocytic leukemia. Proc Natl Acad Sci USA. 1989; 86:5913-5917.

Kumar, S., S. Nagl, J. K. Kalsi, C. T. Ravirajan, D. Athwal, D. S. Latchman, L. H. Pearl, and D. A. Isenberg. Anti-cardiolipin/beta-2 glycoprotein activities co-exist on human anti-DNA antibody light chains. Mol Immunol. 2003; 40:517-530.

Mann, D. L., P. DeSantis, G. Mark, A. Pfeifer, M. Newman, N. Gibbs, M. Popovic, M. G. Sarngadharan, R. C. Gallo, J. Clark, and et al. HTLV-I-associated B-cell CLL: indirect role for retrovirus in leukemogenesis. Science. 1987; 236:1103-1106.

Martin, F., and J. F. Kearney. B-cell subsets and the mature preimmune repertoire. Marginal zone and B1 B cells as part of a "natural immune memory". Immunol Rev. 2000; 175:70-79.

Pascual, V., K. Victor, M. Spellerberg, T. J. Hamblin, F. K. Stevenson, and J. D. Capra. V H restriction among human cold agglutinins. The VH4-21 gene segment is required to encode anti-I and anti-i specificities. J Immunol. 1992; 149:2337-2344.

Potter, M. Antigen-binding myeloma proteins of mice. Adv Immunol. 1977; 25:141-211.

Pugh-Bernard A E, Silverman G J, Cappione A J, Villano M E, Ryan D H, Insel R A, Sanz I. Regulation of inherently autoreactive VH4-34 B cells in the maintenance of human B cell tolerance. The Journal of Clinical Investigation. 2001; 108:1061-1070.

Radic, M. Z., and M. Weigert. Genetic and structural evidence for antigen selection of anti-DNA antibodies. Annu Rev Immunol. 1994; 12:487-520.

Rawstron, A. C., M. J. Green, A. Kuzmicki, B. Kennedy, J. A. Fenton, P. A. Evans, S. J. O'Connor, S. J. Richards, G. J. Morgan, A. S. Jack, and P. Hillmen. Monoclonal B lymphocytes with the characteristics of "indolent" chronic lymphocytic leukemia are present in 3.5% of adults with normal blood counts. Blood. 2002; 100:635-639.

Schroeder H W J, Dighiero G. The pathogenesis of chronic lymphocytic leukemia: analysis of the antibody repertoire [see comments]. Immunol Today. 1994; 15:288-294.

Scott, M. G., D. L. Crimmins, D. W. McCourt, I. Zocher, R. Thiebe, H. G. Zachau, and M. H. Nahm. Clonal characterization of the human IgG antibody repertoire to Haemophilus influenzae type b polysaccharide. III. A single VKII gene and one of several JK genes are joined by an invariant arginine to form the most common L chain V region. J Immunol. 1989; 143:4110-4116.

Seidl, K. J., J. D. MacKenzie, D. Wang, A. B. Kantor, E. A. Kabat, and L. A. Herzenberg. Frequent occurrence of identical heavy and light chain Ig rearrangements. Int Immunol. 1997; 9:689-702.

Silverman, G. J., R. D. Goldfien, P. Chen, R. A. Mageed, R. Jefferis, F. Goni, B. Frangione, S. Fong, and D. A. Carson. Idiotypic and subgroup analysis of human monoclonal rheumatoid factors. Implications for structural and genetic basis of autoantibodies in humans. J Clin Invest. 1988; 82:469-475.

Smith G, Spellerberg M, Boulton F, Roelcke D, Stevenson F. The immunoglobulin VH gene, VH4-21, specifically encodes autoanti-red cell antibodies against the I or i antigens. Vox Sang. 1995; 68:231-235.

Stevenson F K, Spellerberg M B, Chapman C J, Hamblin T J. Differential usage of an autoantibody-associated VH gene, VH4-21, by human B-cell tumors. Leukemia & Lymphoma. 1995; 16:379-384.

Sthoeger, Z. M., M. Wakai, D. B. Tse, V. P. Vinciguerra, S. L. Allen, D. R. Budman, S. M. Lichtman, P. Schulman, L. R. Weiselberg, and N. Chiorazzi. Production of autoantibodies by CD5-expressing B lymphocytes from patients with chronic lymphocytic leukemia. J Exp Med. 1989; 169:255-268.

Sthoeger Z M et al. Am J Hematol 1993; 43:259-264.

Tobin, G., U. Thunberg, A. Johnson, I. Thorn, O. Soderberg, M. Hultdin, J. Botling, G. Enblad, J. Sallstrom, C. Sundstrom, G. Roos, and R. Rosenquist. Somatically mutated Ig V(H)3-21 genes characterize a new subset of chronic lymphocytic leukemia. Blood. 2002; 99:2262-2264.

Tobin G. et al. Blood 2003; 101:4952-4957.

Wakai M, Hashimoto S, Omata M, Sthoeger Z M, Allen S L, Lichtman S M, Schulman P, Vinciguerra V P, Diamond B, Dono M, et al. IgG+, CD5+ human chronic lymphocytic leukemia B cells. Production of IgG antibodies that exhibit diminished autoreactivity and IgG subclass skewing. Autoimmunity. 1994; 19:39-48.

Zemlin, M., M. Klinger, J. Link, C. Zemlin, K. Bauer, J. A. Engler, H. W. Schroeder, Jr., and P. M. Kirkham. Expressed murine and human CDR-H3 intervals of equal length exhibit distinct repertoires that differ in their amino acid composition and predicted range of structures. J Mol Biol. 2003; 334:733-749.

B cell chronic lymphocytic leukemia (B-CLL) is an accumulative disease of slowly proliferating $CD5^+$ B lymphocytes that develops in the aging population. Whereas some patients with B-CLL have an indolent course and die after many years from unrelated causes, others progress very rapidly and succumb within a few years from this currently incurable leukemia. Over the past decade, studies of the structure and function of the B cell antigen receptor (BCR) used by these leukemic cells have helped redefine the nature of this disease.

$CD5^+$ B lymphocytes in B-CLL patients express low levels of surface membrane Ig that serves as their receptor for antigen (BCR). The genetics of this Ig have clinical relevance, as patients with an Ig that is unmutated in the variable (V) regions have a significantly worse outcome than those with significant numbers of mutations in the Ig V region. The biological basis by which the Ig molecule/BCR associates with these distinct outcomes is unclear.

There are several lines of evidence supporting a role for the Ig molecule in the evolution of B-CLL. Analysis of V region gene cassette usage has provided inferential evidence that the Ig molecules on B-CLL cells are not the product of random chance. The distribution of variable region gene cassettes used by B-CLL clones (Schroeder and Dighiero, 1994) differs from that found in normal cells (Brezinschek et al., 1997) with an increased frequency of $V_H$ 3-07, $V_H$ 4-34, and $V_H$ 1-69 genes (Fais et al., 1998). Furthermore, the distribution of mutations among B-CLL cases using these specific $V_H$ genes is selectively and strikingly biased. For instance, the $V_H$ genes of ~40% of B-CLL cases contain <2% differences from the most similar germline gene and ~25% are identical to a germline $V_H$ counterpart. However, 80% of the cases that use a $V_H$ 1-69 are germline and ~90% of these have less than 2% mutation. Conversely, in 93% of cases the $V_H$ 3-07 gene exhibits significant numbers of mutations (≥2% difference from the germline gene). These deviations from randomness in gene use and acquisition of somatic mutations imply that the structure of the antibody molecule, and possibly its antigen specificity thus manifest, played a role in the leukemic transformation of particular B cells.

More recently, sets of B-CLL cases with highly similar Ig molecules have been identified. Our laboratory identified five unmutated IgG-expressing B-CLL cases in which the BCR was remarkably similar in structure (Ghiotto et al. 2003). These Ig molecules used the same $V_H$, D, $J_H$, and in all but one instance the same $V_K$-$J_K$. Furthermore, the HCDR3s were highly similar in sequence and the LCDR3s were virtually identical with a $V_K$-$J_K$ junction contained an invariant, non-templated arginine codon. A larger set of patients expressing a $V_H3$-21/$J_H3$ H chain and a Vλ-3h/Jλ3 L chain have been described by Tobin et al. (2003). These cases also have a HCDR3 that is small and of very similar sequence. The VH3-21 gene is not found at high frequency outside of northern Europe, suggesting an environmental or genetic influence. The patients from both of these groups have a poor clinical course that does not necessarily relate to their VH mutation status.

Functional studies have shown that patients with unmutated Ig V regions can transduce signals through the B cell receptor (BCR), while the mutated BCR cannot. This finding could have major significance since it provides a means by which antigen binding to the BCR might affect the biology of the leukemic cells in vivo. This is especially relevant since many B-CLL cases synthesize autoreactive Ig/BCR molecules (Broker et al., 1988; Borche et al., 1990; Sthoeger et al., 1993) and/or use VH genes that are often found in autoantibodies (Fais et al., 1998). This is consistent with the derivation of the leukemic cells from CD5$^+$ B-cells that in normal individuals are considered the primary source of natural antibodies (Casali and Schettino, 1996).

Despite recent identification of several biomarkers associated with outcome in B-CLL, there is a need for additional prognostic indicators for this disease. Also, there is a long-standing need for therapeutic targets and new therapeutic modalities in B-CLL, for which there is no generally accepted and specific curative regimen. The present invention addresses these needs.

SUMMARY OF THE INVENTION

Accordingly, the inventors have discovered that the B-CLL cells of a significant proportion of B-CLL patients with an aggressive form of the disease share the same classes of $V_H$, D, $J_H$, $V_L$, and $J_L$ antibody genes as other B-CLL patients, forming "sets" of B-CLL patients with highly homologous B cell receptors. This discovery makes practical various therapeutic and diagnostic methods.

Thus, in some embodiments, the invention is directed to isolated and purified preparations of a combination of a light chain antibody gene and a heavy chain antibody gene. In these preparations, the family members of the light chain antibody gene and the heavy chain antibody gene are selected from the group consisting of $V_H4$-39/D6-13/$J_H5$/$V_L$κO12/2/$J_L$κ1/κ2 (Set I), $V_H4$-34/D5-5/$J_H6$/$V_L$κA17/$J_L$κ1/κ2 (Set II), $V_H3$-21/$J_H6$/$V_L$λ3h/$J_L$λ3 (Set III), $V_H1$-69/D3-16/$J_H3$/$V_L$κA27/$J_L$κ1/κ4 (Set IV), $V_H1$-69/D3-10/$J_H6$/$V_L$λ1c/$J_L$λ1 (Set V), $V_H1$-02/D6-19/$J_H4$/$V_L$κO12/2/$J_L$κ1/κ2 (Set VIa), $V_H1$-03/D6-19/$J_H4$/$V_L$κO12/2/$J_L$κ1/κ2 (Set VIb), $V_H1$-18/D6-19/$J_H4$/$V_L$κO12/2/$J_L$κ1 (Set VIc), $V_H1$-46/D6-19/$J_H4$ (Set VId), $V_H5$-51/D6-19/$J_H4$/$V_L$κO12/2/$J_L$κ2 (Set VIe), $V_H1$-69/D3-3/$J_H4$/$V_L$κA19/$J_L$κ4 (Set VII), and $V_H1$-69/D2-2/$J_H6$/$V_L$κL6/2/$J_L$κ3 (Set VIII).

The invention is also directed to cells in culture comprising at least one vector comprising antibody genes from Set I, Set II, Set III, Set IV, Set V, Set VIa, Set VIb, Set VIc, Set VId, Set VIe, Set VII, or Set VIII.

In other embodiments, the invention is directed to isolated and purified antibodies encoded by antibody genes from Set I, Set II, Set III, Set IV, Set V, Set VIa, Set VIb, Set VIc, Set VId, Set VIe, Set VII, or Set VIII.

In further embodiments, the invention is directed to anti-idiotype antibodies that bind to the antigen-binding region of an antibody encoded by antibody genes from Set I, Set II, Set Set IV, Set V, Set VIa, Set VIb, Set VIc, Set VId, Set VIe, Set VII, or Set VIII.

The invention is additionally directed to hybridomas expressing any of the above-described antibodies.

In related embodiments, the invention is directed to bispecific antibodies comprising the binding site of the above-described anti-idiotype antibodies and a binding site that binds to another B-cell antigen.

The present invention is additionally directed to peptide antigens that bind to the antigen-binding region of an antibody encoded by antibody genes of Set I, Set II, Set III, Set IV, Set V, Set VIa, Set VIb, Set VIc, Set VId, Set VIe, Set VII, or Set VIII.

In further embodiments, the invention is directed to aptamers that bind to the antigen-binding region of an antibody encoded by antibody genes of Set I, Set II, Set III, Set IV, Set V, Set VIa, Set VIb, Set VIc, Set VId, Set VIe, Set VII, or Set VIII.

The present invention is also directed to multimeric molecules comprising at least a first and a second binding site. In these embodiments, the first binding site binds to the antigen-binding region of an antibody encoded by antibody genes of Set I, Set II, Set III, Set IV, Set V, Set VIa, Set VIb, Set VIc, Set VId, Set VIe, Set VII, or Set VIII, and the second binding site binds to either (a) the antigen-binding region of an antibody encoded by antibody genes of Set I, Set II, Set III, Set IV, Set V, Set VIa, Set VIb, Set VIc, Set VId, Set VIe, Set VII, or Set VIII or (b) a B-cell antigen.

The invention is additionally directed to isolated and purified preparations of a combination of a light chain antibody gene and a heavy chain antibody gene. In these embodiments, the gene family members of the light chain antibody gene and the heavy chain antibody gene are present in B cells of two or more patients, and the antibody chains of the B cells also share the same isotype, JH, D and JL regions, and the B cells are lymphoproliferative in the patient, or the patient has an autoimmune disease involving the B cells.

In other embodiments, the invention is directed to methods of determining whether a patient with B cell chronic lymphocytic leukemia (B-CLL) has a form of B-CLL that is susceptible to treatment directed to eliminating idiotype-specific B cell receptor-bearing B-CLL cells. The method comprises determining whether the B cell receptors on the patient's B-CLL cells have an idiotype encoded by antibody genes from Set I, Set II, Set III, Set IV, Set V, Set VIa, Set VIb, Set VIc, Set VId, Set VIe, Set VII, or Set VIII.

In related embodiments, the present invention is directed to methods of following the progression of treatment of B-CLL in the patient identified by the above-described method as having a form of B-CLL susceptible to treatment directed to eliminating idiotype-specific B cell receptor-bearing B-CLL cells. The methods comprise determining whether the B cell receptors on the B-CLL cells have an idiotype encoded by antibody genes from Set I, Set II, Set III, Set IV, Set V, Set VIa, Set VIb, Set VIc, Set VId, Set VIe, Set VII, or Set VIII.

In further embodiments, the invention is directed to methods of treating a patient having B-CLL, where the B-CLL is caused by B cells comprising antibody genes from Set I, Set II, Set III, Set IV, Set V, Set VIa, Set VIb, Set VIc, Set VId or Set VIe, Set VII, or Set VIII. The methods comprise administering to the patient any of the anti-idiotype antibodies, peptide antigens, or aptamers described above, or mixtures thereof.

In additional embodiments, the invention is directed to methods of identifying a B-CLL set. The methods comprise identifying the VH, D, JH, VL, and JL antibody gene families present on B-CLL cells, where the same antibody gene families are all present in more than one B-CLL patient.

BRIEF DESCRIPTION OF THE DRAWINGS

FIG. 1 provides VH, D and JH regions of antibody genes from B-CLL cells of Sets I-Vie (1-1: SEQ ID NOS. 1-18 ($V_H$4-39 amino acid sequence and nucleotide sequence, SEQ ID NOS. 1 & 2; D6-13 amino acid sequence and nucleotide sequence, SEQ ID NOS. 3 & 4; $J_H$5 amino acid sequence and nucleotide sequence, SEQ ID NOS. 5 & 6; CLL039, CLL057, CLL114, CLL202, CLL209, YO9249, amino acid and nucleotide sequences SEQ ID NOS. 7-18, respectively); 1-2: SEQ ID NOS. 19-33 ($V_H$4-34 amino acid sequence and nucleotide sequence, SEQ ID NOS. 19 & 20; D5-5 amino acid sequence and nucleotide sequence, SEQ ID NOS. 21 & 22; $J_H$6 nucleotide sequence, SEQ ID NO. 23; CLL183, CLL240, CLL342, AF087422, AJ239333, amino acid and nucleotide sequences SEQ ID NOS. 24-33, respectively); 1-3: SEQ ID NOS. 34-53 ($V_H$1-02 amino acid sequence and nucleotide sequence, SEQ ID NOS. 34 & 35; D6-19 amino acid sequence and nucleotide sequence, SEQ ID NOS. 36 & 37; $J_H$4 amino acid sequence and nucleotide sequence, SEQ ID NOS. 38 & 39; CLL011, CLL270, CLL266, CLL340, AJ239371, AJ487492, U876787 amino acid and nucleotide sequences SEQ ID NOS. 40-53, respectively); 1-4: SEQ ID NOS. 34, 35, 38, 39 and 55-74 ($V_H$1-03 amino acid sequence and nucleotide sequence, SEQ ID NOS. 34 & 35; D6-19 amino acid sequence and nucleotide sequence, SEQ ID NOS. 55 & 56; $J_H$4 amino acid sequence and nucleotide sequence, SEQ ID NOS. 38 & 39; CLL336, CLL360, AF376961, L01278, U86801, U84176, U84162, AF376953, CLL154 amino acid and nucleotide sequences SEQ ID NOS. 58-74, respectively); 1-5: SEQ ID NOS. 34, 35 and 75-88 ($V_H$1-69 amino acid sequence and nucleotide sequence, SEQ ID NOS. 34 & 35; D3-16 amino acid sequence and nucleotide sequence, SEQ ID NOS. 75 & 76; $J_H$3 amino acid sequence and nucleotide sequence, SEQ ID NOS. 77 & 78; CLL068, CLL258, AAC51720, AJ414008, AF460965 amino acid and nucleotide sequences SEQ ID NOS. 79-88, respectively); 1-6: SEQ ID NOS. 34, 35 and 91-99 ($V_H$1-69 amino acid sequence and nucleotide sequence, SEQ ID NOS. 34 & 35; D3-10 amino acid sequence and nucleotide sequence, SEQ ID NOS. 89 & 90; $J_H$5 nucleotide sequence SEQ ID NO. 91; AJ389179 AAC51697 AJ239372 AF376959, amino acid and nucleotide sequences SEQ ID NOS. 92-99, respectively); 1-7: SEQ ID NOS. 34, 35 and 100-115 ($V_H$3-21 amino acid sequence and nucleotide sequence SEQ ID NOS. 34 & 35; $J_H$6 amino acid sequence and nucleotide sequence, SEQ ID NOS. 100 & 101; CLL282, CLL175, CLL412, AJ239379, AF174100, AJ389178, AF299104 amino acid and nucleotide sequences SEQ ID NOS. 102-115, respectively); 1-8: SEQ ID NOS. 1, 2, 38, 39, 36, 37 and 116-128 ($V_H$5-51 amino acid sequence and nucleotide sequence SEQ ID NOS. 1 & 2; D6-19 amino acid sequence and nucleotide sequence, SEQ ID NOS. 36 & 37; $J_H$4 amino acid sequence and nucleotide sequence, SEQ ID NOS. 38 & 39; CLL026, AF099198, AJ414007, AJ239373, AJ555263, AJ272398 amino acid and nucleotide sequences SEQ ID NOS. 116-127, respectively); 1-9: SEQ ID NOS. 34, 35, 54, 36, 37, 40-74, and 116-128 ($V_H$1-02 amino acid sequence and nucleotide sequence, SEQ ID NOS. 34 & 35; D6-19 amino acid sequence and nucleotide sequence, SEQ ID NOS. 36 & 37; $J_H$4 nucleotide sequence, SEQ ID NO. 54; CLL011, CLL270, CLL266, CLL340, AJ239371, AJ487492, U876787 amino acid and nucleotide sequences SEQ ID NOS. 40-53, respectively; CLL336, CLL360, AF376961, L01278, U86801, U84176, U84162, AF376953, CLL154 amino acid and nucleotide sequences SEQ ID NOS. 58-74, respectively; SEQ ID NOS. 38 & 39; CLL026, AF099198, AJ414007, AJ239373, AJ555263, AJ272398 amino acid and nucleotide sequences SEQ ID NOS. 116-127, respectively, and PH1562, SEQ ID NO. 128)).

FIG. 2 shows amino acid alignments of the H chain V regions of all sequences in Sets II, IV, V, VIa-e, and VIII. A period indicates homology with the germline gene. Amino acids in gray are chemically similar to the germline-encoded residues. Underlined positions are known sites of allelic polymorphism. The consensus sequence for the set is shown at the bottom of each alignment. (SEQ ID NOS. 160-167, respectively, for Set IV, Germline, MCLL068, MCLL258, MF9, SMI, CLL022, RIE, Consensus; SEQ ID NOS. 168-172, respectively, for Set VIII, Germline, FS41, UCA4, GO13, Consensus; SEQ ID NOS. 173-181, respectively, for Set V, Germline, CL561, MJ21, RF22, GN12, FUH, ID64, SIN, Consensus; SEQ ID NOS. 182-188, respectively, for Set II, Germline, CJ183, CLL240, CLL342, CLL4B, ID47, Consensus; SEQ ID NOS. 189-197, respectively, for Set Via, Germline, CLL011, CLL266, CLL270, CLL340, CLL3, slv18, CLL-H2B, Consensus; SEQ ID NOS. 198-205, respectively, for Set VIb, Germline, CLL336, CLL360, LAN, CLL-412, POR, PIQ, Consensus; SEQ ID NOS. 206-210, respectively, for Set VIc, Germline, CLL154; SEQ ID NOS. 211-220, respectively, for Set Vid, Germline, BYR, KEM, Consensus, Set Vie, Germline, CLL026, TRE, CLL021, ID38, GO14, AG, HOW, Consensus).

FIG. 3 shows amino acid alignments of the L chain variable regions of all sequences in Sets II, IV, V, VI, and VIII. See FIG. 2 description above. (SEQ ID NOS. 221, 222, 221, 223 and 221, respectively, for Set IV, Germline, CLL068, CLL258, MF9, Consensus; SEQ ID NOS. 224 and 225, respectively, for Set VIII, Germline, GO13; SEQ ID NOS. 226-229, respectively, for Set V, Germline, RF22, GN12, Consensus; SEQ ID NOS. 230, 231, 230, 232 and 230, respectively, for Set I, Germline, CLL183, CLL240, CLL342, Consensus; SEQ ID NOS. 233, 234, 235, 236, 236, 233, 233, 236, 238 and 239, respectively, for Set VI, Consensus, CLL011, CLL266, CLL270, CLL340, CLL336, CLL360, CLL-412, CLL154, TRE, GO14, Consensus).

FIG. 4 shows amino acid and nucleotide sequences of the CDR3 and its junctions of set IV. The H chain sequences are shown at left, and the L chain sequences are shown at right. The most similar germline genes are shown at top. Dots indicate homology with the germline sequence. Dashes indicate no sequence at that position. The numbering at bottom is for convenience of reference and is arbitrary. Sequences from the public databases have their GenBank accession number in parenthesis below the case ID. Distinctive junctional residues exist, including a pair of G codons at the VH-D junction and an N codon at the D-JH junction. The creation of the G codon at the VH-D junction required trimming of the 3' adenosine nucleotide at the end of IgVH, along with N addition. Also, limited trimming at the 5' end of the D segment eliminated the first of the pair of Y codons in all cases. In two instances, D replaced Y and in two other cases N does the same; both of these are charged residues that fit at the negative end of the Kyte-Doolittle scale. The Y codon at the 3' end of the D gene was also eliminated in all sequences of this set. Collectively, these conserved junctional adjustments suggest strong selection for HCDR3 structure. Three rearranged L chain sequences were available for this set and both contained the V.kappa.A27 gene associated with J.kappa.1, J.kappa.4, or J.kappa.5. (SEQ ID NOS. 34, 35, 75, 76, 77, 78, 79-88, and 240-245).

FIG. 5 shows amino acid and nucleotide sequences of the CDR3 and its junctions of Set VIII. The VH-D junctions are dominated by non-templated Gs. The D-JH junction exhibits evidence of trimming and fill-in, with an alteration to M where the final D encoded residue would be found. This is not a known site of polymorphism, although that explanation cannot be excluded. Only one L chain sequence was available for this set (GO13), and this consisted of the V.kappa.L6 and J.kappa.3 genes. There was significant overlap between the germline segments at the VL-JL junction. (SEQ ID NOS. 23, 34, 35, and 254-262).

FIG. 6 shows amino acid and nucleotide sequences of the CDR3 and its junctions of Set V. In these sequences, the 5' end of the germline D gene overlaps the 3' end of the germline IgVH segment to form the VH-D junction. The presence of several nucleotides that do not match either germline sequence in the overlap region suggests that trimming and addition occurred, resulting in a preferred insertion of a residue with a small (A, S, and V) or no (G) side chain. The amino acids at the D-JH junction are not well conserved. However, the consistent relative positioning of the VH, D, and JH segments is intriguing because the region of overlap between the VH and D does not contain significant homology as might be predicted for preferential recombination. This suggests selection for HCDR3 configuration and D-encoded residues rather than specific junctional residues. Two rearranged L chain sequences were available from this set (RF22 and GN12) and both were comprised of V.lamda.1.16 (1c) and J.lamda.1 segments. The level of mutation of both the H and L chains in the members of sets IV, V, and VIII was always <2%, which is consistent with published reports of the frequent lack or scarcity of mutations in the VH1-69 in B-CLL (Kipps et al., 1989; Schroeder et al., 1994; Fais et al., 1998). (SEQ ID NOS. 34, 35, 89-99, and 265-274).

FIG. 7 shows amino acid and nucleotide sequences of the CDR3 and its junctions of Set II. The H chain junctions of the sequences in this set of five cases are quite constrained. The position of the D (D5-5) relative to both VH (VH 4-34) and JH (JH6) segments is identical for each member, leading to equal HCDR3 lengths. The VH-D and D-JH junctions both contain evidence of trimming and addition. These processes produced an aromatic residue (W, Y, F) at the VH-D junction (position 5) followed by a hydrophobic residue (G, P, or A at position 6) and a pair of codons encoding basic residues (K or R) at the D-JH junction (positions 12 and 13). At position 9 in the D segment, four out of the five HCDR3 sequences exhibit a P rather than an A found in the canonical D5-5 segment deposited in the public databases. Although this is most likely a polymorphism of the D5-5 segment rather than a common mutation, the last of the five sequences in this set (CLL ID47) also deviates from the canonical D5-5 sequence at this codon, substituting a D. These highly conserved alterations of the VH-D-JH junctions suggest selection for a very particular HCDR3 structure. The rearranged L chains of this set are also very similar. All three available VLJL sequences use V.kappa.A17 and either J.kappa.1 or J.kappa.2. The junctions are highly similar with only a single difference that results from an abbreviated recombination that eliminates the junctional P from CLL240. These cases are of the IgG isotype. Like most IgG.sup.+ B-CLL cases that express a switched isotype (Fais et al., 1998; Hashimoto et al., 1992; Ghiotto et al., 2004), these cases exceed the 2% difference from germline, albeit slightly, and are thus classified as mutated. (SEQ ID NOS. 19-33, and 279-282).

FIG. 8 shows amino acid and nucleotide sequences of the CDR3 and its junctions of set VI. The VH1-02 germline sequence is shown. There are no sequence differences between VH1-02 and VH1-03, 1-18, 1-46, or 5-51 for the displayed region. The J.kappa.1 gene is shown, and homology between CLL011 and CLL-412 and J.kappa.2 at positions where the germline sequence of J.kappa.2 and J.kappa.1 are different is indicated with an asterisk. This set is composed of five subsets, totally 22 patients that share HCDR3 and VLJL characteristics but incorporate different IgVH genes (1-02, 1-03, 1-18, 1-46, and 5-51). Each of these genes belongs to the same VH clan (Kirkham et al., 1992). The HCDR3 of these subsets all share a precise VHD overlap. Curiously, the D6-19 segment was used in a nonproductive reading frame. However, this stop codon was in the region of overlap with the terminal IgVH sequence and was trimmed, thereby allowing productive rearrangements with the JH4 segment. The D-JH junctions contain evidence for trimming and addition. The first nongermline templated codon after the D segment is enriched in redundant L codons, but the remaining junctional codons are not tightly conserved. All the rearranged L chains available for this set use the V.kappa.O12/2 gene with J.kappa. use restricted to J.kappa.1 and J.kappa.2. Of these 10 sequences, 9 are essentially identical to that of the germline in the LCDR3 and junctional regions. Thus, this set is unified not only by its common HCDR3 structure and motifs but also by the use of a virtually identical VLJL partner with a very restricted LCDR3 composition. (SEQ ID NOS. 34, 35, 38, 39, 40-49, 52-53, 57-64, 67-74, 116-128, 197, 299 and 300).

DETAILED DESCRIPTION OF THE INVENTION

The present invention is based on the discovery that a significant proportion of B-CLL patients having genetic and protein markers consistent with an aggressive form of the disease or a manifestly aggressive form of the disease regardless of said markers, have B-CLL cells with B cell receptors encoded by antibody gene family members that other B-CLL patients also have. The inventors have identified at least 10 sets of patients (see Table 1 in the Example), where the patients within each set have the same B-CLL B cell receptor antibody genes. This accounts for approximately 10% of B-CLL patients, and about 20% of those patients that have genetic and protein markers consistent with an aggressive form of the disease. See the Example for details relating to the discovery of these sets.

As is known, aggressive forms of B-CLL are correlated with B cells that have relatively few IgV gene mutations and have intercellular expression of ZAP-70, and cell surface expression of CD38 and CD23. These markers are evaluated at first diagnosis to predict which patients will have an aggressive form of the disease, in order to determine a course of treatment. Because the B-CLL cells from patients belonging to identified "sets" with common B cell receptor genes have low or absent IgV mutations (see Table 1 in Example), it is predicted that patients having B-CLL cells from each of these sets will have an aggressive form of the disease.

The Figures provide relevant sequences of the B cell receptor antibodies and antibody genes of B-CLL cells of several patients in the sets. Notable is the relatively small amount of variation within each set in the number of nucleotides added during the VH-D-JH and VL-JL recombinations.

While two of these sets (Sets I and III) have been previously identified, it was believed that those two sets were anomalous and were not expected to account for more than a small fraction of B-CLL cases. Thus, the discovery, disclosed herein, of multiple other sets that account for a significant proportion of patients with B-CLL, in particular the apparently aggressive form of the disease, makes practical the use of various methods and compositions for diagnosis and treatment of B-CLL, based on the sets identified.

Thus, in some embodiments, the present invention is directed to isolated and purified preparations of a combination of a light chain antibody gene and a heavy chain antibody gene. The family members of the light chain antibody gene and the heavy chain antibody gene of these preparations make up any one of the following sets: VH4-39/D6-13/JH5/VLκO12/2/JLκ1/κ2 (Set I), VH4-34/D5-5/JH6/VLκA17/JLκ1/κ2 (Set II), VH3-21/JH6/VLλ3h/JLλ3 (Set III), VH1-69/D3-16/JH3/VLκA27/JLκ1/κ4 (Set IV), VH1-69/D3-10/JH6/VLλ1c/JLλ1 (Set V), VH1-02/D6-19/JH4/VLκO12/2/JLκ1/κ2 (Set VIa); VH1-03/D6-19/JH4/VLκO12/2/JLκ1/κ2 (Set VIb); VH1-18/D6-19/JH4/VLκO12/2/JLκ1 (Set VIc); VH1-46/D6-19/JH4 (Set VId); VH5-51/D6-19/JH4/VLκO12/2/JLκ2 (Set VIe), VH1-69/D3-3/JH4/VLκA19/JLκ4 (Set VII), and $V_H$1-69/D2-2/$J_H$6/$V_L$κL6/2/$J_L$κ3 (Set VIII). In some preferred embodiments, the family members of the light chain antibody gene and the heavy chain antibody gene are selected from the group consisting of Set II, Set IV, Set V, Set VIa, Set VIb, Set VIc, Set VId, Set VIe, Set VII, and Set VIII; in other preferred embodiments, the family members of the light chain antibody gene and the heavy chain antibody gene are selected from the group consisting of Set II, Set IV, Set V, Set VIa, Set VIb, Set VIc, Set VId, Set VIe, and Set VII. In additional preferred embodiments, the family members of the light chain antibody gene and the heavy chain antibody gene are selected from the group consisting of Set II, Set IV, Set V, Set VIa, Set VIb, Set VIc, Set VId, Set VIe, and Set VIII. In still other preferred embodiments, the family members of the light chain antibody gene and the heavy chain antibody gene are selected from the group consisting of Set I, Set II, Set III, Set IV, Set V, Set VIa, Set VIb, Set VIc, Set VId, Set VIe, and Set VII.

These preparations, comprising the antibody genes of each of the 12 identified sets, are useful for preparing reagents for diagnosis and treatment methods described below. Such useful reagents include compounds that specifically bind to the antigen binding site of the antibodies encoded by these genes, as further described below.

The antibody genes in these sets can be identified without undue experimentation by known methods, e.g., as described in the Example, using routine sequencing methods. The antibody genes are categorized herein as from a particular germline gene even if the antibody gene has several mutations.

The combination of antibody genes can be in any form, including single chain genes, as are known in the art. Preferably, the antibody genes are on a vector or vectors, such as a plasmid or viral vector, in order to facilitate their maintenance, as with a cloning vector, and to be able to produce the antibodies encoded by the genes, as with an expression vector. Cells in culture comprising a vector comprising antibody genes from Set I, Set II, Set III, Set IV, Set V, Set VIa, Set VIb, Set VIc, Set VId, Set VIe, Set VII, or Set VIII are also envisioned. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII.

In other embodiments, the invention is directed to isolated and purified antibodies encoded by antibody genes from one of Set I, Set II, Set III, Set IV, Set V, Set VIa, Set VIb, Set VIc, Set VId, Set VIe, Set VII, or Set VIII. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII. As previously discussed, these antibodies, which are expressed as the B cell receptor on the B-CLL cells from individuals in the identified sets, can be used to identify reagents that bind to the antibody's antigen binding site. These antibodies can be produced by any known method. Non-limiting examples include antibodies from a hybridoma made from the CLL cells and antibodies from cloned antibody genes. As used herein, the antibodies can be in any form that includes at least one antigen binding region. The term "antibody" thus includes an Fab, Fab2, or Fv fragment. The present invention also includes hybridomas that produce the above antibodies.

As is known in the art, a consensus sequence for each set can be identified that provides the amino acid sequence that is most similar to the sequence of the antibodies of all members of the set. This consensus sequence can be used to identify an antibody binding site that is most similar to all the members of the set, in order to most efficiently produce a binding partner (e.g., an anti-idiotype antibody) that binds to all members of the set. Thus, the invention is also directed to these amino acid consensus sequences and to nucleotide sequences encoding the consensus sequences.

The invention is also directed to anti-idiotype antibodies that bind to the antigen-binding region of an antibody encoded the antibody genes of Set I, Set II, Set III, Set IV, Set V, Set VIa, Set VIb, Set VIc, Set VId, Set VIe, Set VII, or Set VIII. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII. Since these anti-idiotype antibodies bind to the antibody binding site of the antibodies that are the B cell receptor of a B-CLL cells from a significant portion of B-CLL patients with the aggressive form of the disease, the anti-idiotype antibodies can be used in various diagnostic and treatment methods for B-CLL.

The anti-idiotype antibodies of these embodiments can be made by standard methods, e.g., screening a phage display library, or producing a hybridoma making monoclonal antibodies against the antigen binding site of the antibodies encoded by the various B-CLL gene sets described above. As such, these anti-idiotype antibodies can be from any vertebrate species but are preferably mouse antibodies, human antibodies, or humanized antibodies. Such antibodies can be made by known methods without undue experimentation. The present invention also includes hybridomas that produce the above anti-idiotype antibodies.

In related embodiments, the invention is directed to bispecific antibodies comprising the binding site of any of the above-described anti-idiotype antibodies and a binding site that binds to another B cell antigen. The B cell antigen can be any antigen on the B cell, such as a signal-transducing antigen (either surface or intracellular), or a surface antigen. It is expected that, in many cases, the bi-specific antibodies having a binding site to a B cell surface antigen would bind to the B cell more tightly than an antibody with two anti-idiotype binding domains, since anti-idiotype antibodies can be of low avidity. The bi-specific antibodies having a binding site to a signal-transducing antigen would be expected to expedite the signaling pathway, such as a terminal differentiation pathway or an apoptotic pathway, thus expediting the elimination of a B cell contributing to the B-CLL disease.

The above anti-idiotype antibodies can also be combined in a mixture that provides the antibodies directed to the binding sites from more than one set. This mixture can include as many anti-idiotype antibodies as desired, including those any combination, or all of the sets. The latter mixture would be effective in diagnosis or treatment methods for all of the sets, rather than just one set.

When used for treatment methods, the above-described anti-idiotype antibodies or mixtures thereof would be in a pharmaceutically acceptable excipient.

The above-described anti-idiotype antibody compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

In preferred embodiments, the anti-idiotype antibody compositions of the present invention can easily be administered parenterally such as for example, by intramuscular, intrathecal, subcutaneous, intraperitoneal, or, in the most preferred embodiments, intravenous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the anti-idiotype antibody composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the anti-idiotype antibody composition may also take place using a nasal tampon or nasal sponge.

In other embodiments, the invention is directed to peptide antigens that bind to the antigen-binding region of an antibody encoded by antibody genes from Set I, Set II, Set III, Set IV, Set V, Set VIa, Set VIb, Set VIc, Set VId, Set VIe, Set VII, or Set VIII. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII. Such peptide antigens can be made by well-known methods, e.g., phage display library or high-density peptide library, without undue experimentation.

As used herein, the term "peptide antigen" includes peptide mimetics, also known as peptidomimetics, which retain the same binding abilities as the analogous amino acid peptide. Peptide mimetics are peptides comprised of amino acid analogs, such as D-amino acids, that are more resistant to protease degradation than their L-amino acid peptide counterparts. Various peptide mimetics are known in the art, and any peptide mimetic can be produced without undue experimentation.

As is analogous with the anti-idiotype antibodies, these peptide antigens can be prepared as a mixture, in order to provide a diagnostic or therapeutic reagent useful for several, or all of the B-CLL sets. Also as with the anti-idiotype antibodies, the peptide antigens can also be usefully provided in a pharmaceutically acceptable excipient, for therapeutic applications, preferably for parenteral administration.

In further embodiments, the invention is directed to aptamers that bind to the antigen-binding region of an antibody encoded by antibody genes from Set I, Set II, Set III, Set IV, Set V, Set VIa, Set VIb, Set VIc, Set VId, Set VIe, Set VII, or Set VIII. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII. As is known, aptamers are single stranded oligonucleotides or oligonucleotide analogs that bind to a particular target molecule, in this case an antibody binding site. Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known. Thus, these aptamers are analogous to the anti-idiotype antibodies and the peptide antigens previously discussed. As such, they can also be provided as a mixture of two or more, in order to have a reagent that can be utilized with more than one set of patients. They can also be provided in a pharmaceutically acceptable excipient, for therapeutic purposes, preferably for parenteral administration.

In some embodiments, the anti-idiotype antibody, peptide antigen, aptamer, or mixtures of these as previously described can usefully be functionalized or derivatized. One useful derivitization includes a cellular toxin. Such reagents are useful in a "magic bullet" approach to B-CLL therapy, where the toxin would be expected to kill only the B-CLL cell that the anti-idiotype antibody, peptide antigen, or aptamer bound. Several cellular toxins known in the art for these embodiments can be used for this approach, including radioactive moieties, ricin, and chemotherapeutic agents.

In other embodiments, the anti-idiotype antibody, peptide antigen, aptamer, or mixtures of these as previously described can usefully be further functionalized to comprise a detectable moiety, such as a fluorophore, or an enzyme that can be treated with a substrate to produce a colored reaction product. Non-limiting examples of the latter enzyme is horseradish peroxidase and alkaline phosphatase. Such labeled anti-idiotype antibody, peptide antigen, aptamer, or mixtures can be used for diagnostic purposes, for example in labeling the B-CLL cells for fluorescence activated cell sorter analysis or for histological observation of the cells. These methods are more fully described below.

In additional embodiments, the invention is directed to multimeric molecules comprising at least a first and a second binding site, the first binding site binding to the antigen-binding region of an antibody encoded by antibody genes from Set I, Set II, Set III, Set IV, Set V, Set VIa, Set VIb, Set VIc, Set VId, Set VIe, Set VII, or Set VIII, and the second binding site binding to either (a) the same antigen-binding region of an antibody as the first binding site or (b) another B-cell antigen. Preferably, the antibody genes are selected from the group consisting of Set II, Set IV, Set V, Set VIa, Set VIb, Set VIc, Set VId, Set VIe, Set VII, and Set VIII, or Set II, Set IV, Set V, Set VIa, Set VIb, Set VIc, Set VId, Set VIe, and Set VII, or Set II, Set IV, Set V, Set VIa, Set VIb, Set VIc, Set VId, Set VIe, and Set VIII, or Set I, Set II, Set III, Set IV, Set V, Set VIa, Set VIb, Set VIc, Set VId, Set VIe, and Set VII. By providing multiple binding sites to a particular set, these multimeric compositions would be expected to bind more effectively than the single binding site peptide antigens or aptamers, or the double binding site anti-idiotype antibodies, as described above. In preferred embodiments, the multimeric molecules of these embodiments comprise more than five binding sites. These multimeric molecules can be made by the skilled artisan without undue experimentation.

In some embodiments, all of the binding sites of the multimeric molecule bind to the antigen-binding region of an antibody encoded by antibody genes from Set I, Set II, Set III, Set IV, Set V, Set VIa, Set VIb, Set VIc, Set VId, Set VIe, Set VII, or Set VIII. These binding sites can be directed to one epitope, to more than one epitope of the antigen-binding region, or to antigen-binding regions of more than one set.

In these multimeric molecules, the binding sites can be all antibody binding sites, all peptide binding sites, all aptamer binding sites, or combinations thereof.

More generally, the invention is further directed to an isolated and purified preparation of a combination of a light chain antibody gene and a heavy chain antibody gene, where the gene family members of the light chain antibody gene and the heavy chain antibody gene are present in B cells of two or more patients, where the antibody chains of the B cells also share the same isotype, JH, D and JL regions, and where the B cells are lymphoproliferative in the patient, or where the patient has an autoimmune disease involving the B cells.

The discovery that B-CLL patients can be classified into sets having common antibody chains raises the possibility that other lymphoproliferative or autoimmune diseases involving B cells can also be classified into sets, where each set of patients share B cells that are involved in the disease with the same antibody genes. The instant disclosure provides evidence for this, since a patient in Set I has an immunocytoma, a patient in set II has a small cell lymphocytic lymphoma (SLL), and a patient in set VIa has a marginal zone lymphoma (SMZL) (FIG. 1). It is also highly probable that other B-CLL sets exist.

Preferred lymphoproliferative disorders within these embodiments include Hodgkin's disease, non-Hodgkin's lymphoma, Burkitt's lymphoma, myeloma, a monoclonal gammopathy with antibody-mediated neurologic impairment, a monoclonal gammopathy of unknown significance, and a monoclonal lymphocytosis of undetermined significance. Preferred autoimmune diseases within these embodiments include systemic lupus erythematosus, myasthenia gravis, Grave's disease, type I diabetes mellitus, autoimmune peripheral neuropathy, and autoimmune hemolytic anemia.

As previously discussed, the above compositions are useful for various diagnostic and therapeutic methods that are envisioned as part of the invention.

Thus, in some embodiments, the invention is directed to methods of (a) determining whether a patient with B cell chronic lymphocytic leukemia (B-CLL) has a form of B-CLL susceptible to treatment directed to eliminating idiotype-specific B cell receptor-bearing B-CLL cells, or (b) following the progression of treatment of B-CLL in a patient having a form of B-CLL susceptible to treatment directed to eliminating idiotype-specific B cell receptor-bearing B-CLL cells. In these embodiments, the methods comprise determining whether the B cell receptors on the B-CLL cells have an idiotype encoded by antibody genes from Set I, Set II, Set III, Set IV, Set V, Set VIa, Set VIb, Set VIc, Set VId, Set VIe, Set VII, or Set VIII. A determination that the B cell receptors have the specified idiotype at once establishes that the patient apparently has an aggressive form of B-CLL, and that the B-CLL can be treated using the anti-idiotype, peptide, aptamer, mixtures, or multimeric molecules described above, particularly those conjugated to a cellular toxin. Additionally, by continual monitoring of the idiotype of the B cells from the patient, one can follow the progress of treatment, since an effective treatment would exhibit a decreasing amount of B cells having an idiotype from the B-CLL set. No B cells having an idiotype from the B-CLL set essentially means that the patient is in remission or cured of the B-CLL.

It can be seen, then, that it is useful to monitor progression of the treatment by quantifying the B cells having an idiotype from the B-CLL set, since a decreasing quantity of the B cells indicates an effective treatment, while an increasing quantity of the B cells indicates an ineffective treatment.

In these methods the determination step can be by any means known in the art. Nonlimiting examples include (a) amplification of idiotype-determining regions of the antibody genes or mRNA, e.g., by polymerase chain reaction, and evaluating whether the amplified regions are amplified from the B-CLL set in question; (b) sequencing the amplified regions; (c) evaluating whether the amplified regions hybridize with equivalent regions from the B-CLL set in question; (d) evaluating whether the patient has circulating antibodies with an idiotype encoded by the antibody genes from the B-CLL set in question; (e) evaluating whether the patient has antibodies that bind to a binding agent (e.g., an anti-idiotype antibody, a peptide antigen, or an aptamer, as described above, preferably comprising a detectable moiety) specific for the idiotype encoded by the antibody genes from the set in question; or (f) mixing a labeled anti-idiotype antibody, peptide antigen, or aptamer with lymphocytes of the patient and determining whether lymphocytes that bind to the composition are present, e.g., using a Coulter counter or a cell sorter.

The above methods can be used with a B-CLL patient at any stage of the disease, including in a pre-leukemic, early leukemic, frank leukemic state. Furthermore, the B-CLL cells can be obtained from the blood, the bone marrow, the spleen, and/or the lymph nodes, depending on the results of initial diagnosis and the stage of the disease.

The present invention is also directed to methods of treating a patient having B-CLL caused by B cells comprising antibody genes from Set I, Set II, Set III, Set IV, Set V, Set VIa, Set VIb, Set VIc, Set VId, Set VIe, Set VII, or Set VIII. The methods comprise administering to the patient the above described anti-idiotype antibody, peptide antigen, aptamer, or mixture as previously described, in a pharmaceutically acceptable excipient.

Although the anti-idiotype antibody, peptide antigen, aptamer, or mixture by themselves could be effective in eliminating the B cells, because they could set off an apoptotic cascade in the cells, it is preferred that the anti-idiotype antibody, peptide antigen, aptamer, or mixture also comprise a cellular toxin, as described above, that can directly kill the cell.

Additionally, the invention is directed to methods of identifying other B-CLL sets. The methods comprise identifying the VH, D, JH, VL, and JL classes of antibody genes present on B-CLL cells, where the same classes are all present in more than one B-CLL patient. It is understood that databases and computerized comparison methods could be employed in this identification process.

Once additional sets are identified, a compound that binds to the antigenic site of an antibody encoded by the antibody genes can be identified by methods previously described, where the compound is useful for therapeutic and diagnostic purposes. Since the results provided in the Example establish that a significant proportion of B-CLL patients are in a set that shares the same B-CLL antibody genes with other patients, it is highly likely that other sets will be found.

It would be understood by the skilled artisan that the therapeutic agent in these methods is preferably an anti-idiotype antibody, a peptide antigen, or an aptamer that binds to the antigen binding site of the antibody encoded by the antibody genes that are typical of a 'set'.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1. Multiple Distinct Sets of Stereotyped Antigen Receptors Indicate a Role for Antigen in Promoting Chronic Lymphocytic Leukemia Example Summary.

Previous studies suggest that the diversity of the expressed variable (V) region repertoire of the Ig H chain of B-CLL cells is restricted. Although limited examples of marked constraint in the primary structure of the H and L chain V regions exist, the possibility that this level of restriction is a general principle in this disease has not previously been known. This report describes eight sets of patients, mostly with unmutated or minimally mutated IgV genes, with strikingly similar BCR arising from the use of common H and L V region gene segments that share CDR3 structural features such as length, amino acid composition, and unique amino acid residues at recombination junctions. Thus, a much more striking degree of structural restriction of the entire BCR and a much higher frequency of receptor sharing exists among patients than previously appreciated. The data imply that either a significant fraction of B-CLL cells were selected by a limited set of antigenic epitopes at some point in their development and/or that they derive from a distinct B cell subpopulation with a limited Ig V region diversity. These shared, stereotyped Ig molecules may be valuable probes for antigen identification and important targets for cross-reactive idiotypic therapy. Sets II, IV, V, VI and VIII are described in Messmer et al., 2004, where they are named Sets IV, I, III, V and II, respectively.

Introduction.

The B-lymphocyte clone expanded in chronic lymphocytic leukemia (B-CLL) expresses low levels of surface membrane Ig, the B cell antigen receptor (BCR). The genetics of this Ig have clinical relevance, as patients with a clone whose Ig variable (V) region has no or few mutations have a significantly worse outcome than those with significant numbers of Ig V mutations (Damle et al., 1999; Hamblin et al., 1999). The biology underlying this association is unclear.

Several lines of evidence support a role for the BCR in the evolution of B-CLL (reviewed in Chiorazzi and Ferrarini, 2003). The distribution of individual $IgV_H$ in B-CLL clones differs from that found in normal cells (Fais et al., 1998), with an increased frequency of $V_H1$-69, $V_H4$-34, and $V_H3$-07 (Fais et al., 1998; Schroeder and Dighiero, 1994; Johnson et al., 1997). In addition, the distribution of mutations among B-CLL cases using these specific $V_H$ genes is selectively biased (Fais et al., 1998; Schroeder and Dighiero, 1994; Kipps et al., 1989).

Recently two subgroups of B-CLL cases with remarkable similarity of the entire BCR (V regions of the H and L chain) were identified (Tobin et al., 2003; Ghiotto et al., 2004). Although these findings are provocative, they have been considered rare and potentially anomalous, since, in one instance the clones expressed IgG (Ghiotto et al., 2004) and in the other geography and ethnicity may be relevant (Tobin et al., 2002). This report describes another eight groups of B-CLL patients that express BCRs of strikingly similar primary structure defined by highly similar Ig V regions in the H and L chains and, in particular, distinct H and L CDR3 configurations. Thus, a significant fraction of B-CLL clones derive from B-lymphocytes with constrained antigen binding sites that could recognize individual, discrete antigen(s) or classes of structurally similar epitopes.

Materials and Methods

IgV Gene Sequencing.

$V_HDJ_H$ and $V_LJ_L$ sequences were determined by previously described methods (Fais et al., 1998; Ghiotto et al., 2004).

Database Searches.

B-CLL Ig H chain V amino acid sequences from our collection (n=255) and the public databases (n=197) were subjected to BLAST searches of both nucleotide and protein databases to identify similar sequences. The criteria used to define "Sets" of similar rearranged $V_HDJ_H$ were: A) use of the same $V_H$, D, and $J_H$ germline genes, B) use of the same D segment reading frame and position relative to the $V_H$, plus or minus one codon, and C) an amino acid similarity within the HCDR3 of ≥60% identity. In addition, all B-CLL Ig H protein sequences were aligned and clustered using the ClustalW alignment algorithm. Sequences clustering tightly were visually inspected for similarity. All of these searches used the complete $V_HDJ_H$ and as such were weighted toward sequences that used the same $V_H$ gene. To identify sequences with similar HCDR3 but different $V_H$ genes, CDR3 motifs from the various sets were used to search the public databases with the ProteinInfo search engine (http://prowl.rockefeller.edu/). The criteria for the members of Set V were altered to permit the use of different $IgV_H$ genes that were members of the same $IgV_H$ clan, while retaining the criteria for the rearranged $V_LJ_L$. Use of the same specific $IgV_L$ gene and ≥85% LCDR3 identity was required for the inclusion of a companion rearranged $V_LJ_L$ in a Set.

538 $V_H$ sequences from CD5$^+$ and CD5$^-$ peripheral B-lymphocytes (Tobin et al., 2002; Geiger et al., 2000) were downloaded from the public database. These 538 sequences were independently compared to the translated databases using tblastn on the BlastMachine at the AMDeC Bioinformatics Core Facility at the Columbia Genome Center, Columbia University.

Detailed nucleotide and amino acid sequence alignments of the junctional regions and complete protein sequence alignments of the sequences described here are provided in the Figures.

Results and Discussion

Identification of Subgroups of B-CLL Patients with Highly Restricted $V_HDJ_H$ Segments and Shared HCDR3 Configurations.

Each B-CLL-derived $V_HDJ_H$ sequence in our database was compared with every B-CLL sequence in our collection (n=255) as well as with those in the public Ig V gene databases (n=197) using nucleotide and protein sequence BLAST. In addition, all available B-CLL H chain V region sequences were phylogenetically grouped using the ClustalW method; sequences that clustered together were further analyzed for HCDR3 sequence similarity. These screening methods identified Sets of sequences (Table 1) consisting of the same $IgV_H$ with highly similar HCDR3 resulting from identical D (when identifiable) and $J_H$ segment use, D segment reading frame, similar D segment position relative to $IgV_H$, and HCDR3 length, and significant (≥60%) amino acid sequence identity.

TABLE I

Sets of B-CLL cases that share Ig V region genes and have a high degree of similarity in H CDR3.

| Set | Int. B-CLL[a] | Public B-CLL | Pub. other | Isotype | $V_H$ | $V_H$ Mutation % max | min | median | D | $J_H$ | $V_L$ | $J_L$ |
|---|---|---|---|---|---|---|---|---|---|---|---|---|
| I | 5 | 0 | 1[b] | IgG | 4-39 | 1.0 | 0.0 | 0.5 | 6-13 | 5 | κO12/2 (4/5) | κ1/κ2 |
| II | 3 | 2 | 0 | IgG | 4-34 | 3.1 | 2.0 | 2.7 | 5-5 | 6 | κA17 (3/3) | κ1/κ2 |
| III | 3 | 2 | 2[c] | IgM | 3-21 | 2.4 | 0.0 | 1.4 | ND | 6 | λ3h (4/4) | λ3 |
| IV | 2 | 2 | 1[d] | IgM | 1-69 | 0.6 | 0.0 | 0.0 | 3-16 | 3 | κA27 (2/2) | κ1/κ4 |
| V | 0 | 4 | 0 | IgM | 1-69 | 0.3 | 0.0 | 0.3 | 3-10 | 6 | λ1-16 (1/1) | λ1 |
| VIa | 4 | 2 | 1[e] | IgM | 1-02 | 0.3 | 0.0 | 0.0 | 6-19 | 4 | κ O12/2 (4/4) | κ1/κ2 |
| VIb | 2 | 4 | 0 | IgM | 1-03 | 2.0 | 0.3 | 0.8 | 6-19 | 4 | κ O12/2 (3/3) | κ1/κ2 |
| VIc | 1 | 0 | 0 | IgM | 1-18 | 1.2 | 1.2 | 1.2 | 6-19 | 4 | κ O12/2 (1/1) | κ1 |
| VId | 0 | 2 | 0 | IgM | 1-46 | 0.0 | 0.0 | 0.0 | 6-19 | 4 | 0/0 | |
| VIe | 1 | 6 | 0 | IgM | 5-51 | 2.7 | 0.0 | 0.2 | 6-19 | 4 | κ O12/2 (1/2) | κ2 |
| VII | 2 | 0 | 0 | IgM | 1-69 | 0.0 | 0.0 | 0.0 | 3-3 | 4 | κ A19 (1/1) | κ4 |
| VIII | 3 | 0 | 0 | IgM | 1-69 | | | 0.0 | 2-2 | 6 | κL6 | κ3 |

[a]Internal B-CLL
[b]immunocytoma, accession Y09249
[c]small lymphocytic leukemia, accession AF299104, and elderly normal, accession AF174100
[d]anti-cardiolipin antibody, accession AF460965
[e]small marginal zone lymphoma, accession AJ487492

Three subsets of Set VI (VIa, VIb, and VIe) contained sequences that utilized different $IgV_H$ genes but used the same D and $J_H$ segments, the same Vκ, and had highly similar HCDR3 configurations. Therefore, we used the HCDR3 motif common to these three subsets to search public databases for additional sequences with the same HCDR3 configuration potentially associated with a different $IgV_H$ segment. This search was not restricted to B-CLL sequences. The approach confirmed the previously identified subsets and identified two additional subsets of Set VI (VIc and VId).

The public database searches identified 21 $V_HDJ_H$ sequences, belonging to one of the eight individual Sets, bringing the total number of sequences among these Sets to 45. Interestingly, only two of the 21 sequences culled from the public databases were not derived from B-CLL cells. These two were from an anti-cardiolipin antibody producing B cell (Set IV) and from a splenic marginal zone lymphoma (Set VIa). This distribution of similar sequences is particularly striking since, at the time of this search, the public databases contained only 197 Ig H chain V region sequences from B-CLL patients (excluding those from our laboratories) out of a total of over 8,500 H chain V region sequences (search of Entrez with terms "human immunoglobulin heavy chain variable" produced 8,874 hits in the nucleotide database and over 6,183 hits in the protein database on Dec. 12, 2003).

Pairing Restricted $V_LJ_L$ Rearrangements with $V_HDJ_H$ Segments in Sets.

Figure 2:
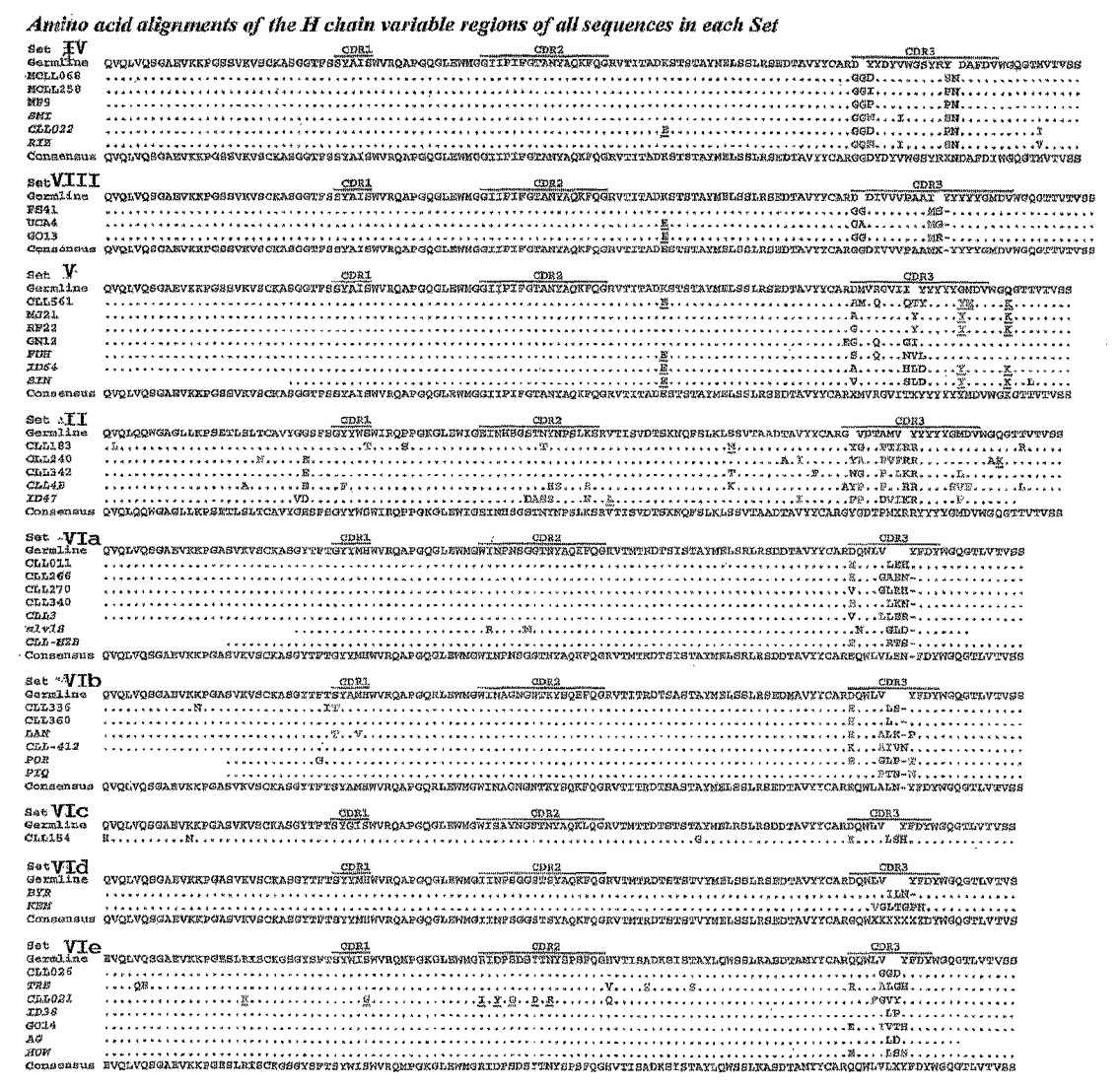

$V_LJ_L$ sequences corresponding to the shared $V_HDJ_H$ of the 5 Sets were available for most of our B-CLL cases and for a few of those identified in the public databases. Remarkably, the available $IgV_L$ were highly conserved within Sets and the corresponding $J_L$ were very restricted (Table 1 and FIG. 2). Six of the eight Sets with available L chains expressed the κ isotype.

IgV gene mutation status and isotype restrictions of individual Sets. Most of the $IgV_H$ sequences in each Set differed by <2.0% from the most similar germline gene, with the exception of Set II in which the median level of mutation was 3.0%. Notably, the deduced protein structures in those sequences that were considered "mutated" using the typical 2% threshold differed from the germline by relatively low levels. Only one sequence, from Set II (CLL ID47, FIG. 2), differed by more than 5% from its germline counterpart. The corresponding $IgV_L$ in each Set exhibited low levels of mutation; in some cases $V_L$ displayed <2.0% difference while $V_H$ had ≥2% difference from the germline sequence (Table 1 and FIG. 2).

The H chain isotype was the same among members of a Set. All Sets expressed IgM, except for Set IV that consisted of $IgG^+$ cases, similar to a patient group reported previously (Ghiotto et al., 2004).

H and L CDR3 Characteristics of the Individual Sets.

Figure 8:
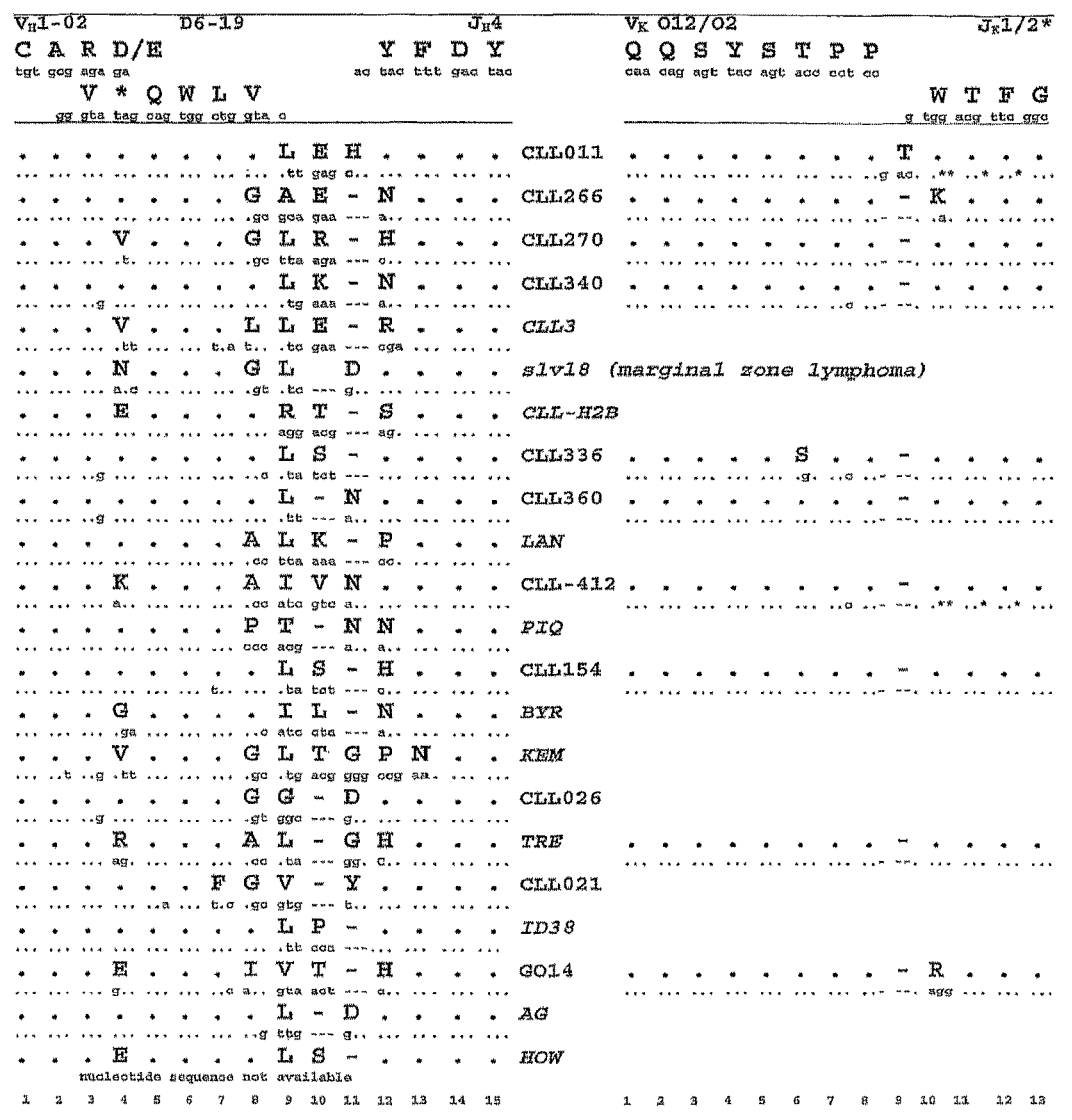

We identified trends in the chemical, structural, or functional nature of the residues that comprise the H and L CDR3s, and in particular their $V_H$-D and D-$J_H$ junctions. For example, the D segments in the HCDR3s of these Sets were read in the hydrophobic and stop reading frames more often than in normal (Zemlin et al., 2003) and B-CLL (Fais et al., 1999) cells. For all cases in Set VI, the D6-19 segment is read in a non-productive reading frame. However, the germline stop codon, located in the region of overlap with the terminal $IgV_H$ sequence, was trimmed, allowing productive rearrangements with the $J_H4$ segment (FIG. 8).

Figure 6:
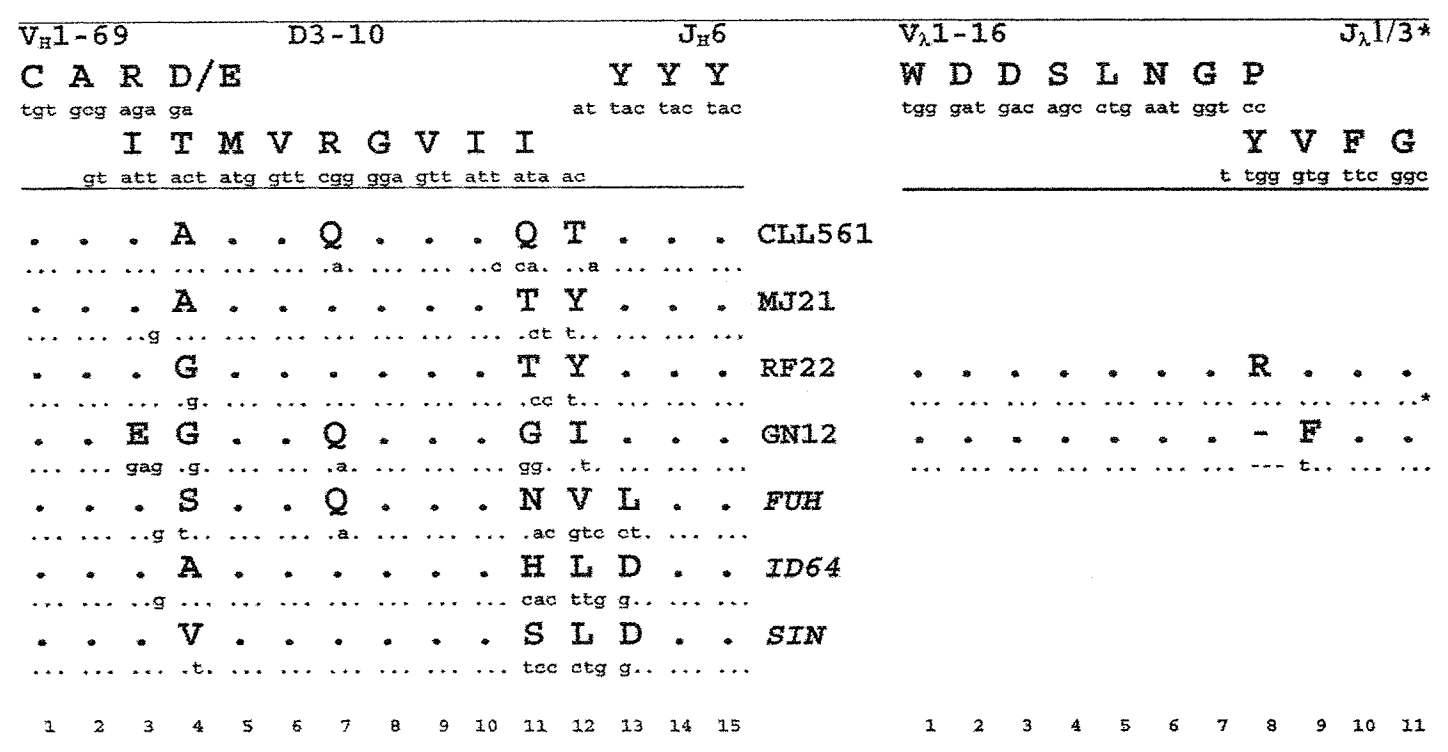
Figure 7:
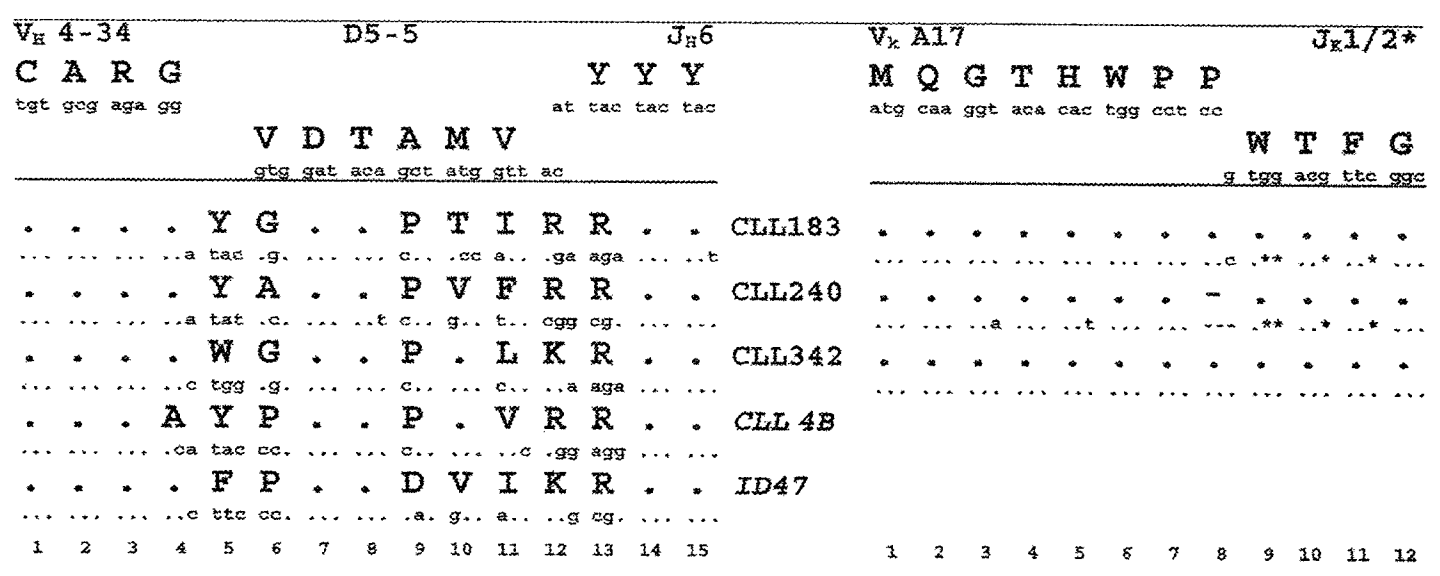

Also of note was the repeated occurrence of certain non-germline encoded amino acids within D segments in some of the Sets. For example in all members of Set VIII, a change to M is found at the 3'end of the D segment (FIG. 5), a position that is not known to be polymorphic. Three of 7 sequences in Set V had an R to Q change within the D3-10 segment that is also not listed as polymorphic (FIG. 6). In 4 of 5 cases in Set II, P replaced A in the portion of HCDR3 encoded by the canonical D5-5 segment. While this is most likely a polymorphism of the D segment rather than a common mutation, the last of the 5 sequences in this set (CLL ID47) also deviates from the canonical D5-5 sequence at this codon, substituting a D (FIG. 7). Thus even if these amino acid changes represent polymorphisms, their relative consistency within each Set suggests a selection for these residues.

Members of several Sets have common junctional residues that were not templated by any known germline gene segments and therefore presumably arose from trimming and/or addition during recombinational assembly. The sequences in Set IV all contain a pair of Gs at the $V_H$-D junction and an N at the D-$J_H$ junction (FIG. 4). A very similar $V_H$-D junctional finding exists in Set VIII (FIG. 5). All sequences in Set II contain an aromatic residue at the $V_H$-D and a pair of basic residues (R or K) at the D-$J_H$ junction (FIG. 7).

Other trends in the composition of the H and L CDR3s are found in the other Sets. These and the fine details of the nucleotide and amino acid sequences of the $V_HDJ_H$ and $V_LJ_L$ junctions for each Set are shown and discussed in the Supplemental data (see FIGS. 4-8).

Structural Similarities of the BCR Among Members of the Sets.

Figure 3:
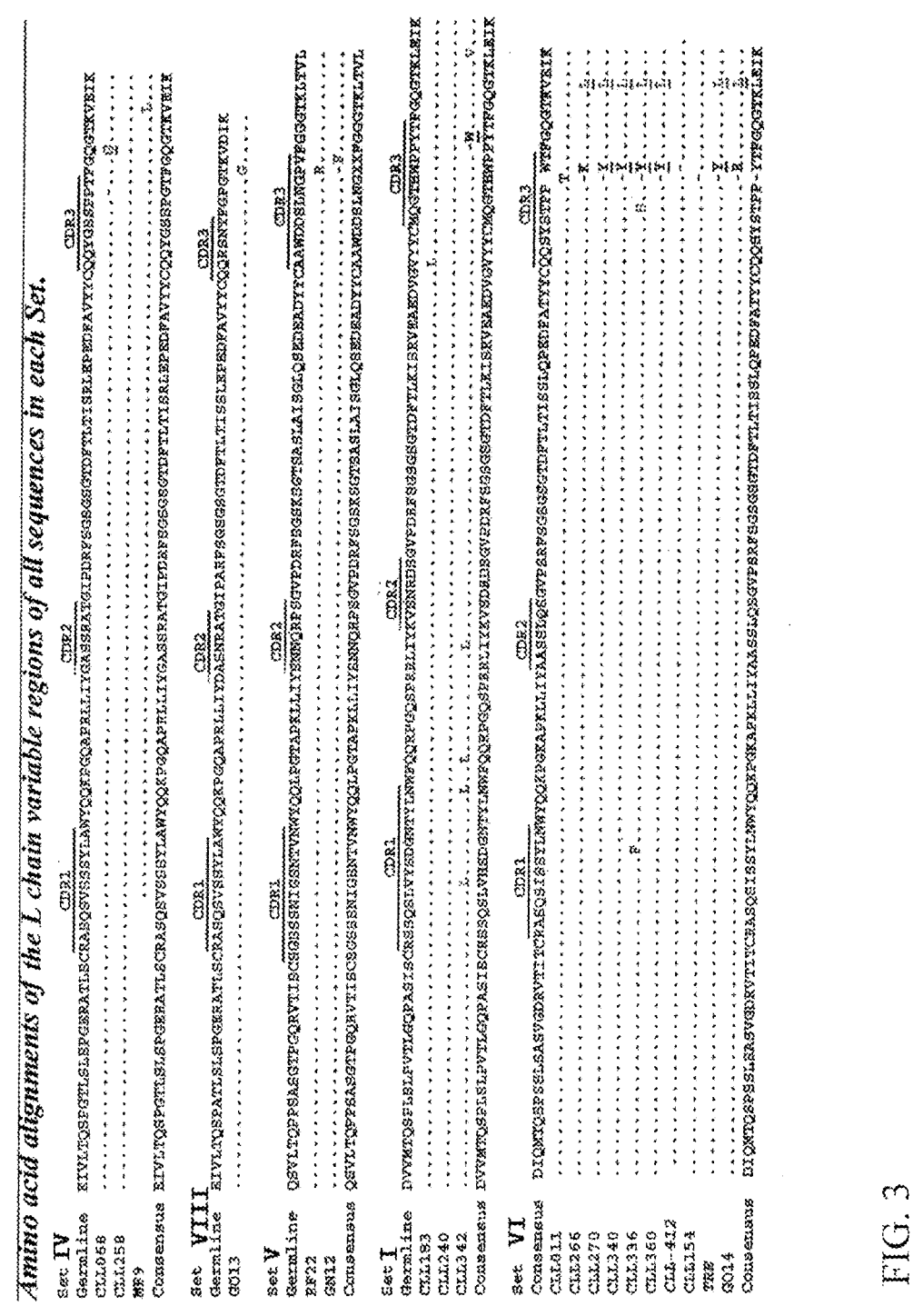

The deduced $V_HDJ_H$ and $V_LJ_L$ protein sequences for each member of the stereotyped Sets are presented in FIGS. 2 and 3. Because most members of the Sets use the same $IgV_H$, primarily in an unmutated form, associated with the same D and $J_H$ segments and since these rearrangements are virtually always paired with an identical $IgV_L$ that is restricted in its linked $J_L$, the primary structural features of the entire BCR of each Set are likely remarkably similar. Furthermore, the amino acid sequences of HCDR1, HCDR2, LCDR1, and LCDR2 of members of the individual Sets are extremely similar, if not identical (e.g., Sets IV, V, VIII, and the Set VI subsets). In Set II, some amino acid differences exist in these regions due to somatic mutation.

These data indicate a much more marked constraint on the primary structure of the BCR in B-CLL than previously appreciated. They also indicate that this principle occurs in a sizeable number of patients. Collectively, ~12% (31 of 255: 22 from this study, 5 from our previous study (Ghiotto et al., 2004), and 4 that match another described set (Tobin et al., 2002; 2003)) of all of sequences in our internal laboratory B-CLL database and ~20% (27 of 131) of those with unmutated IgV belong to one of the eight stereotyped Sets described here or one of the two patient groups mentioned above (Tobin et al., 2002; 2003; Ghiotto et al., 2004). Approximately the same overall frequency (~12%) was encountered among the sequences from the public databases (21 of 197), although the proportion of the public B-CLL sequences that are unmutated was not determined Most of the rearrangements in these Sets lack or have few somatic mutations, and even those whose $V_H$ surpass the 2% threshold commonly used as the criterion to define significant IgV gene mutations (Fais et al., 1998; Schroeder and Dighiero et al., 1994) are only slightly above that level. This suggests that restricted BCR structure is primarily a feature of those patients with the worse clinical course and outcome (Damle et al., 1999; Hamblin et al., 1999). It appears that 1 of 5 B-CLL cases with unmutated BCRs fit into one of these defined Sets. Additional Sets will likely be uncovered as more Ig V region sequences are defined in B-CLL, and all unmutated cases may be similar to one of a discrete number of archetypal Sets. Although Sets IV, V, VII, and VIII use unmutated 1-69, they differ from previously described 1-69-expressing B-CLL cases that have restrictions in specific D and $J_H$ segments associations (Fais et al., 1998; Johnson et al., 1997). These differences include $J_H$ ($J_H3$ vs. $J_H6$ in Set I), D (D2 vs. D3 family and VκL6 with an extremely short LCDR3 in Set VIII), and L chain (λ vs. κ in Set V) gene use.

Initial studies that considered only $IgV_H$ or $V_HDJ_H$ (Fais et al., 1998; Schroeder and Dighiero, 1994; Johnson et al., 1997; Chiorazzi and Ferrarini, 2001) pointed toward limited structural diversity in the antigen-binding sites of B-CLL. However, our results are much more striking because of the remarkable similarity of the sequences within a Set and the virtual mathematic impossibility that this similarity arose by chance. If gene segment use in B-CLL was random, the probability of finding the same combination of $V_HDJ_H$ and $V_LJ_L$ segments in independent leukemic (or normal) B cells would be $>1\times10^{-6}$. Therefore, one would not expect to identify two B-CLL patients with BCRs comprised of the same $V_HDJ_H/V_LJ_L$ until $>1$ million cases were analyzed. This calculation is conservative since it does not account for diversity at the $V_H$-D, D-$J_H$, and $V_L$-$J_L$ junctions that can be quite extensive (potentially exceeding $1\times10^{-9}$ and reaching $1\times10^{-12}$), although receptor editing and revision could limit these possibilities somewhat. Nevertheless, the level and frequency of BCR structural restriction in clusters of patients reported here is extraordinary and appears to be higher than any other B or T cell lymphoproliferative disorder reported to date.

Finding similar Ig H chain V region sequences by homology searches of the public databases is not, in itself, completely surprising because some $IgV_H$ are expressed in a biased fashion and ~6,600 different $V_H$-D-$J_H$ combinations can occur. Because the databases contain more than that number of Ig H chain V region sequences, identifying the same recombined gene segments is not improbable. When we analyzed 538 $CD5^+$ and $CD5^-$ B cell-derived H chain V region sequences, we identified many pairs of similar sequences and some groups of similar sequences. However these groups derived from B cells of diverse sources, as would be expected if the similarities were the product of random chance. In contrast, the similarity to a given B-CLL-derived sequence detected in our database comparisons arose almost exclusively from other B-CLL sequences (19/21) or other lymphoproliferative disorders (1/21), even though the entire database was searched. Only one identified sequence was from a non-B-CLL clone and that coded an autoantibody (Table I and FIG. 2). Although the proper normal B cell repertoire against which B-CLL clones should be compared remains an open question (Chiorazzi and Ferrarini, 2003), these results demonstrate that sequence sets of restricted cellular origin are not a generalized phenomenon in the public database.

Therefore, the development of B-CLL must involve B cell clones with restricted IgV and/or BCR structure. While it seems unlikely that the expression of particular BCR gene combinations could be the sole promoting factor for leukemogenesis, a strong inherent bias in gene segment association and $V_HDJ_H/V_LJ_L$ pairing in the B cell population that gives rise to B-CLL cannot be formally excluded, especially since the cell of origin for B-CLL is still uncertain (Chiorazzi and Ferrarini, 2003). Although evidence exists in mice for biases in the recombination of particular Ig V gene segments prior to antigen experience (Seidl et al., 1997), the extent of restriction imposed by recombination biases at both the H and L chain V gene loci in those instances, especially at the V-(D)-J junctions, are not as severe as in the Sets described here. To our knowledge, there is no known subpopulation of human B cells in which the frequency of similar rearrangements, independent of antigen selection, is as great as among these B-CLL cases.

Therefore, antigen selection probably has a strong restrictive influence on the transformation of a normal B-lymphocyte to a B-CLL cell. A simple model would postulate that the transforming event is coupled with antigen specificity, i.e., an individual B-lymphocyte from a highly diverse population could bind and internalize a transforming agent (e.g., virus) via its BCR. Although this seems unlikely, such a mechanism has been implied for B-CLL (Mann et al., 1987).

Alternatively, antigen could be a promoting factor for transformation, selecting specific clones for expansion from an initially diverse population of B-lymphocytes and fostering their development to and in the transformed state (Chiorazzi and Ferrarini, 2003). This would be the case if the B-CLL-susceptible cell population were pre-selected for antigen-reactivity, and therefore BCR structure, by exposure to distinct antigens or classes of antigens during their development. These clones could differ among patients, especially if the selecting antigens were foreign or autologous and possibly polymorphic. From within these clonal expansions, one member could develop an initial transforming lesion that would promulgate the leukemogenic cascade independent of antigen.

Finally, the initial transforming events could occur at random within a diverse B cell population or a previously antigen-selected population, and the subsequent nurturing of the transformed clone to clinical B-CLL could require ongoing BCR engagement by antigen (Chiorazzi and Ferrarini, 2003). Recently, clonal expansions of B cells with phenotypic characteristics of B-CLL were found in normal elderly individuals (Rawstron et al., 2002; Ghia et al., 2004. The clinical relevance of these clones is not established. However, they may represent clones that have some of the genetic lesions of B-CLL but lack BCR specificities that would result in sufficient ongoing stimulus to mature them into clinical B-CLL.

The remarkable protein similarity of the entire BCR among members of each Set (FIGS. 2 and 3) suggests that they could recognize the same or similar antigens. While the nature of the antigen(s) cannot be directly deduced from the Ig sequences presented here, there are several reasons to suspect that they are autoantigens or carbohydrates possibly derived from bacterial or viral coats, or a combination of the two.

$V_H1$-69 (Sets I, II, and III) and $V_H3$-21 (previously described Set in Tobin et al., 2002; 2003) are enriched among rheumatoid factors (Silverman et al., 1988; He et al., 1995). $V_H4$-34 (Set II) is used in every case of monoclonal cold agglutinin disease (Pascual et al., 1992) and in autoimmune conditions. Indeed the inherent autoreactivity of this $V_H$ segment elicits a major inhibitory process by the immune system that keeps 4-34$^+$ B cells from diversifying into high affinity, isotype-switched B cells (Pugh-Bernard et al., 2001). The anti-cardiolipin antibody identified as a member of Set IV implies that the other members of that Set may be specific for cardiolipin or DNA, since some antibodies to the former react with the latter (Kumar et al., 2003). In addition, restricted $V_HDJ_H$ and/or $V_LJ_L$ gene segments are features of B cells that produce anti-carbohydrate mAb in human (Scott et al., 1989) and mouse (Potter, 1977).

Characteristic junctional residues are also a feature of anti-carbohydrate mAb and autoantibodies and basic junctional residues, as seen in Sets II, IV, and VIe (FIG. 2), often indicate reactivity with acidic targets such as DNA (Radic and Weigert, 1994). The synthesis of autoreactive Ig/BCR molecules by many B-CLL clones (Sthoeger et al., 1989; Borche et al., 1990) supports a link between the unique BCR structural features of these Sets and autoantibodies.

The non-B-CLL Ig sequences that matched these B-CLL stereotypes may give insight into the identity of the B-CLL progenitor cell(s). One of those two derived from a splenic marginal zone lymphoma (SMZL; Set VIa, FIG. 2) and the other from an autoantibody-producing B cell (Set IV, FIG. 2). Interestingly, normal MZ B cells produce mAb that can recognize thymus-independent type II antigens and autoantigens (Bendelac et al., 2001). In addition, the Ig V region repertoire of murine MZ B cells is very restricted in gene segment use and structure that requires intact BCR signal transduction to develop (Martin and Kearnet, 2000). MZ B cells appear to be progenitors for gastric MALT lymphoma (Isaacson, 1999) and have been proposed as precursors of B-CLL cells (Chiorazzi and Ferrarini, 2003). If one infers common antigenic reactivity based on the similar sequences within a Set, a significant fraction of B-CLL cases, and in particular those with unmutated IgV genes, produce mAb that recognize one of a limited, discrete array of antigens or epitopes. With such an interpretation, some B-CLL cases may resemble gastric MALT lymphoma regarding the role of antigenic drive (in that instance, *H. pylori*) in the promotion of malignancy. The stereotyped Ig molecules reported here might be valuable probes to identify antigens that drive the leukemogenic process in B-CLL.

Finally, these Sets of stereotyped Ig molecules may serve as therapeutic targets on B-CLL cells. A conceptual drawback to targeting the BCR as a tumor-specific antigen has been the apparent need to create an individualized reagent for each patient. However, since our data indicate that there is potentially extensive overlap in BCR structure and specificities among groups of B-CLL cases, this approach may be far less daunting. Indeed, since ~20% of the cases with unmutated $IgV_H$ genes fall into one of these Sets, such targeting might be most effective in those cases that have the worst prognosis, are least responsive to therapy, and have the most aggressive clinical courses (Damle et al., 1999; Hamblin et al., 1999).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An isolated human or humanized anti-idiotype antibody that specifically binds to the antigen-binding region of an antibody selected from the group consisting of (i) an antibody with an H chain comprising SEQ ID NO:167 and an L chain comprising SEQ ID NO:221, (ii) an antibody with an H chain comprising SEQ ID NO:181 and an L chain comprising SEQ ID NO:229, (iii) an antibody with an H chain comprising SEQ ID NO:197 and an L chain comprising SEQ ID NO:239, (iv) an antibody with an H chain comprising SEQ ID NO:208 and an L chain comprising SEQ ID NO:239, (v) an antibody with an H chain comprising SEQ ID NO:207 and an L chain comprising SEQ ID NO:239, (vi) an antibody with an H chain comprising SEQ ID NO:211 and an L chain comprising SEQ ID NO:239 (vii) an antibody with an H chain comprising SEQ ID NO:220 and an L chain comprising SEQ ID NO:239, and (viii) an antibody with an H chain comprising SEQ ID NO:172 and an L chain comprising SEQ ID NO:225.

2. The anti-idiotype antibody of claim 1, which is a human antibody.

3. The anti-idiotype antibody of claim 1, which is a humanized antibody.

4. A mixture of two or more of the anti-idiotype antibodies of claim 1.

5. A pharmaceutical composition comprising at least one of the anti-idiotype antibodies of claim 1, in a pharmaceutically acceptable excipient.

6. The anti-idiotype antibody of claim 1, further comprising a cellular toxin.

7. The anti-idiotype antibody of claim 6, wherein the cellular toxin is a chemotherapeutic agent.

8. The anti-idiotype antibody of claim 1, further comprising a detectable moiety.

9. A hybridoma producing the antibody of claim 1.

10. A method of treating a patient having B-CLL B cells comprising antibody genes from VH1-69/D3-16/JH3/VLκA27/JLκ1/κ4 (Set IV), VH1-69/D3-10/JH6/VLλ1c/JLλ1 (Set V), VH1-02/D6-19/JH4/VLκO12/2/JLκ1/κ2 (Set VIa), VH1-03/D6-19/JH4/VLκO12/2/JLκ1/κ2 (Set VIb), VH1-18/D6-19/JH4/VLκO12/2/JLκ1 (Set VIc), VH1-46/D6-19/JH4 (Set VId), VH5-51/D6-19/JH4/VLκO12/2/JLκ2 (Set VIe), or VH1-69/D2-2/JH6/VLκL6/2/JLκ3 (Set VIII), the method comprising administering to the patient the anti-idiotype antibody of claim 1 in an amount effective to treat B-CLL.

11. The method of claim 10, wherein the anti-idiotype antibody further comprises a cellular toxin.

* * * * *

SEQUENCE LISTING

```
<160> NUMBER OF SEQ ID NOS: 300

<210> SEQ ID NO 1
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X = His or Gln

<400> SEQUENCE: 1

Cys Ala Arg Xaa
1

<210> SEQ ID NO 2
<211> LENGTH: 11
<212> TYPE: DNA
<213> ORGANISM: Homo sapiens

<400> SEQUENCE: 2
tgtgcgagac a                                                          11

<210> SEQ ID NO 3
<211> LENGTH: 7
<212> TYPE: PRT
<213> ORGANISM: Homo sapiens

<400> SEQUENCE: 3

Gly Tyr Ser Ser Ser Trp Tyr
1               5

<210> SEQ ID NO 4
<211> LENGTH: 21
<212> TYPE: DNA
<213> ORGANISM: Homo sapiens

<400> SEQUENCE: 4
gggtatagca gcagctggta c                                               21
```

```
<210> SEQ ID NO 5
<211> LENGTH: 4
<212> TYPE: PRT
<213> ORGANISM: Homo sapiens

<400> SEQUENCE: 5

Asn Trp Phe Asp
1

<210> SEQ ID NO 6
<211> LENGTH: 12
<212> TYPE: DNA
<213> ORGANISM: Homo sapiens

<400> SEQUENCE: 6
aactggttcg ac                                                             12

<210> SEQ ID NO 7
<211> LENGTH: 18
<212> TYPE: PRT
<213> ORGANISM: Homo sapiens

<400> SEQUENCE: 7

Cys Ala Ser Ser Arg Gly Tyr Ser Ser Ser Trp Trp Ser Ser Asn Trp
1               5                   10                  15

Phe Asp

<210> SEQ ID NO 8
<211> LENGTH: 54
<212> TYPE: DNA
<213> ORGANISM: Homo sapiens

<400> SEQUENCE: 8
tgtgcgagct ccagagggta tagcagcagc tggtggtcat ctaactggtt cgac              54

<210> SEQ ID NO 9
<211> LENGTH: 19
<212> TYPE: PRT
<213> ORGANISM: Homo sapiens

<400> SEQUENCE: 9

Cys Ala Arg His Leu Gly Tyr Ser Ser Ser Trp Tyr Gly Ala Ala Asn
1               5                   10                  15

Trp Phe Asp

<210> SEQ ID NO 10
<211> LENGTH: 57
<212> TYPE: DNA
<213> ORGANISM: Homo sapiens

<400> SEQUENCE: 10
tgtgcgagac atctgggata tagcagcagc tggtatgggg cagccaactg gttcgac           57

<210> SEQ ID NO 11
<211> LENGTH: 18
<212> TYPE: PRT
<213> ORGANISM: Homo sapiens

<400> SEQUENCE: 11

Cys Ala Arg Arg Phe Gly Tyr Ser Ser Ser Trp Tyr Gly Leu Asp Trp
1               5                   10                  15
```

Phe Asp

<210> SEQ ID NO 12
<211> LENGTH: 54
<212> TYPE: DNA
<213> ORGANISM: Homo sapiens

<400> SEQUENCE: 12
tgtgcgagac ggttcgggta tagcagcagc tggtacggtt tagactggtt cgac      54

<210> SEQ ID NO 13
<211> LENGTH: 19
<212> TYPE: PRT
<213> ORGANISM: Homo sapiens

<400> SEQUENCE: 13

Cys Ala Arg Ser Thr Gly Ala Ser Ser Ser Trp Tyr Ser Trp Arg Asn
1               5                   10                  15

Trp Phe Asp

<210> SEQ ID NO 14
<211> LENGTH: 57
<212> TYPE: DNA
<213> ORGANISM: Homo sapiens

<400> SEQUENCE: 14
tgtgcgaggt cgaccgggta tagcagcagc tggtactctt ggcgcaattg gttcgac      57

<210> SEQ ID NO 15
<211> LENGTH: 19
<212> TYPE: PRT
<213> ORGANISM: Homo sapiens

<400> SEQUENCE: 15

Cys Ala Arg Gln Ala Gly Tyr Ser Ser Ser Trp Tyr Gly Pro Ser Asn
1               5                   10                  15

Trp Phe Asp

<210> SEQ ID NO 16
<211> LENGTH: 57
<212> TYPE: DNA
<213> ORGANISM: Homo sapiens

<400> SEQUENCE: 16
tgtgcgagac aagctgggta tagcagcagc tggtacggcc cctccaactg gttcgac      57

<210> SEQ ID NO 17
<211> LENGTH: 18
<212> TYPE: PRT
<213> ORGANISM: Homo sapiens

<400> SEQUENCE: 17

Cys Ala Arg His Glu Gly Tyr Ser Ser Ser Trp Tyr Arg Ser Asp Trp
1               5                   10                  15

Phe Asp

<210> SEQ ID NO 18
<211> LENGTH: 54
<212> TYPE: DNA
<213> ORGANISM: Homo sapiens

<400> SEQUENCE: 18

```
tgtgcgagac atgaggggta tagcagcagc tggtacagga gcgactggtt cgac        54
```

<210> SEQ ID NO 19
<211> LENGTH: 4
<212> TYPE: PRT
<213> ORGANISM: Homo sapiens

<400> SEQUENCE: 19

Cys Ala Arg Gly
1

<210> SEQ ID NO 20
<211> LENGTH: 11
<212> TYPE: DNA
<213> ORGANISM: Homo sapiens

<400> SEQUENCE: 20

```
tgtgcgagag g                                                       11
```

<210> SEQ ID NO 21
<211> LENGTH: 6
<212> TYPE: PRT
<213> ORGANISM: Homo sapiens

<400> SEQUENCE: 21

Val Asp Thr Ala Met Val
1               5

<210> SEQ ID NO 22
<211> LENGTH: 20
<212> TYPE: DNA
<213> ORGANISM: Homo sapiens

<400> SEQUENCE: 22

```
gtggatacag ctatggttac                                              20
```

<210> SEQ ID NO 23
<211> LENGTH: 11
<212> TYPE: DNA
<213> ORGANISM: Homo sapiens

<400> SEQUENCE: 23

```
attactacta c                                                       11
```

<210> SEQ ID NO 24
<211> LENGTH: 15
<212> TYPE: PRT
<213> ORGANISM: Homo sapiens

<400> SEQUENCE: 24

Cys Ala Arg Gly Tyr Gly Asp Thr Pro Thr Ile Arg Arg Tyr Tyr
1               5                   10                  15

<210> SEQ ID NO 25
<211> LENGTH: 45
<212> TYPE: DNA
<213> ORGANISM: Homo sapiens

<400> SEQUENCE: 25

```
tgtgcgagag gatacgggga tacacctacc attagaagat actat                  45
```

<210> SEQ ID NO 26
<211> LENGTH: 15
<212> TYPE: PRT

```
<213> ORGANISM: Homo sapiens

<400> SEQUENCE: 26

Cys Ala Arg Gly Tyr Ala Asp Thr Pro Val Phe Arg Arg Tyr Tyr
1               5                   10                  15

<210> SEQ ID NO 27
<211> LENGTH: 45
<212> TYPE: DNA
<213> ORGANISM: Homo sapiens

<400> SEQUENCE: 27
tgtgcgagag gatatgcgga tactcctgtg tttcggcgct actac            45

<210> SEQ ID NO 28
<211> LENGTH: 15
<212> TYPE: PRT
<213> ORGANISM: Homo sapiens

<400> SEQUENCE: 28

Cys Ala Arg Gly Trp Gly Asp Thr Pro Met Leu Lys Arg Tyr Tyr
1               5                   10                  15

<210> SEQ ID NO 29
<211> LENGTH: 45
<212> TYPE: DNA
<213> ORGANISM: Homo sapiens

<400> SEQUENCE: 29
tgtgcgagag gctgggggga tacacctatg cttaaaagat actac            45

<210> SEQ ID NO 30
<211> LENGTH: 15
<212> TYPE: PRT
<213> ORGANISM: Homo sapiens

<400> SEQUENCE: 30

Cys Ala Arg Ala Tyr Pro Asp Thr Pro Met Val Arg Tyr Tyr
1               5                   10                  15

<210> SEQ ID NO 31
<211> LENGTH: 49
<212> TYPE: DNA
<213> ORGANISM: Homo sapiens

<400> SEQUENCE: 31
tgtgcgagag catacccgga tacacctatg gtcaggaggt actaccarg        49

<210> SEQ ID NO 32
<211> LENGTH: 15
<212> TYPE: PRT
<213> ORGANISM: Homo sapiens

<400> SEQUENCE: 32

Cys Ala Arg Gly Phe Pro Asp Thr Asp Val Ile Lys Arg Tyr Tyr
1               5                   10                  15

<210> SEQ ID NO 33
<211> LENGTH: 45
<212> TYPE: DNA
<213> ORGANISM: Homo sapiens

<400> SEQUENCE: 33
tgtgcgagag gcttcccgga tacagatgtg attaagcgct actac            45
```

<210> SEQ ID NO 34
<211> LENGTH: 4
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: X = Asp or Glu

<400> SEQUENCE: 34

Cys Ala Arg Xaa
1

<210> SEQ ID NO 35
<211> LENGTH: 11
<212> TYPE: DNA
<213> ORGANISM: Homo sapiens

<400> SEQUENCE: 35
tgtgcgagag a                                                          11

<210> SEQ ID NO 36
<211> LENGTH: 5
<212> TYPE: PRT
<213> ORGANISM: Homo sapiens

<400> SEQUENCE: 36

Val Gln Trp Leu Val
1               5

<210> SEQ ID NO 37
<211> LENGTH: 21
<212> TYPE: DNA
<213> ORGANISM: Homo sapiens

<400> SEQUENCE: 37
gggtatagca gtggctggta c                                               21

<210> SEQ ID NO 38
<211> LENGTH: 4
<212> TYPE: PRT
<213> ORGANISM: Homo sapiens

<400> SEQUENCE: 38

Tyr Phe Asp Tyr
1

<210> SEQ ID NO 39
<211> LENGTH: 14
<212> TYPE: DNA
<213> ORGANISM: Homo sapiens

<400> SEQUENCE: 39
actactttga ctac                                                       14

<210> SEQ ID NO 40
<211> LENGTH: 15
<212> TYPE: PRT
<213> ORGANISM: Homo sapiens

<400> SEQUENCE: 40

Cys Ala Arg Glu Gln Trp Leu Val Leu Glu His Tyr Phe Asp Tyr
1               5                   10                  15

<210> SEQ ID NO 41
<211> LENGTH: 45
<212> TYPE: DNA
<213> ORGANISM: Homo sapiens

<400> SEQUENCE: 41
tgtgcgaggg agcagtggct ggtacttgag cactactttg actac                45

<210> SEQ ID NO 42
<211> LENGTH: 14
<212> TYPE: PRT
<213> ORGANISM: Homo sapiens

<400> SEQUENCE: 42

Cys Ala Arg Val Gln Trp Leu Gly Leu Arg His Phe Asp Tyr
1               5                   10

<210> SEQ ID NO 43
<211> LENGTH: 42
<212> TYPE: DNA
<213> ORGANISM: Homo sapiens

<400> SEQUENCE: 43
tgtgcgagag tgcagtggct gggcttaaga cactttgact ac                   42

<210> SEQ ID NO 44
<211> LENGTH: 14
<212> TYPE: PRT
<213> ORGANISM: Homo sapiens

<400> SEQUENCE: 44

Cys Ala Arg Glu Gln Trp Leu Gly Ala Glu Asn Phe Asp Tyr
1               5                   10

<210> SEQ ID NO 45
<211> LENGTH: 42
<212> TYPE: DNA
<213> ORGANISM: Homo sapiens

<400> SEQUENCE: 45
tgtgcgagag agcagtggct gggcgcagaa aactttgact ac                   42

<210> SEQ ID NO 46
<211> LENGTH: 14
<212> TYPE: PRT
<213> ORGANISM: Homo sapiens

<400> SEQUENCE: 46

Cys Ala Arg Glu Gln Trp Leu Val Leu Lys Asn Phe Asp Tyr
1               5                   10

<210> SEQ ID NO 47
<211> LENGTH: 42
<212> TYPE: DNA
<213> ORGANISM: Homo sapiens

<400> SEQUENCE: 47
tgtgcgaggg agcagtggct ggtactgaaa aactttgact ac                   42

<210> SEQ ID NO 48
<211> LENGTH: 14
<212> TYPE: PRT
<213> ORGANISM: Homo sapiens

```
<400> SEQUENCE: 48

Cys Ala Arg Val Gln Trp Leu Leu Leu Glu Arg Phe Asp Tyr
1               5                   10

<210> SEQ ID NO 49
<211> LENGTH: 42
<212> TYPE: DNA
<213> ORGANISM: Homo sapiens

<400> SEQUENCE: 49
tgtgcgagag ttcagtggtt attactcgaa cgatttgact ac                        42

<210> SEQ ID NO 50
<211> LENGTH: 14
<212> TYPE: PRT
<213> ORGANISM: Homo sapiens

<400> SEQUENCE: 50

Cys Ala Arg Asn Gln Trp Leu Gly Leu Asp Tyr Phe Asp Tyr
1               5                   10

<210> SEQ ID NO 51
<211> LENGTH: 42
<212> TYPE: DNA
<213> ORGANISM: Homo sapiens

<400> SEQUENCE: 51
tgtgcgagaa accagtggct gggtctcgac tactttgact ac                        42

<210> SEQ ID NO 52
<211> LENGTH: 14
<212> TYPE: PRT
<213> ORGANISM: Homo sapiens

<400> SEQUENCE: 52

Cys Ala Arg Glu Gln Trp Leu Val Arg Thr Ser Phe Asp Tyr
1               5                   10

<210> SEQ ID NO 53
<211> LENGTH: 42
<212> TYPE: DNA
<213> ORGANISM: Homo sapiens

<400> SEQUENCE: 53
tgtgcgagag agcagtggct ggtaaggacg agctttgact ac                        42

<210> SEQ ID NO 54
<211> LENGTH: 11
<212> TYPE: DNA
<213> ORGANISM: Homo sapiens

<400> SEQUENCE: 54
actttgacta c                                                          11

<210> SEQ ID NO 55
<211> LENGTH: 5
<212> TYPE: PRT
<213> ORGANISM: Homo sapiens

<400> SEQUENCE: 55

Val Gln Trp Leu Val
1               5
```

<210> SEQ ID NO 56
<211> LENGTH: 21
<212> TYPE: DNA
<213> ORGANISM: Homo sapiens

<400> SEQUENCE: 56
gggtatagca gtggctggta c                                              21

<210> SEQ ID NO 57
<211> LENGTH: 14
<212> TYPE: PRT
<213> ORGANISM: Homo sapiens

<400> SEQUENCE: 57

Cys Ala Arg Glu Gln Trp Leu Val Leu Ser Tyr Phe Asp Tyr
1               5                   10

<210> SEQ ID NO 58
<211> LENGTH: 42
<212> TYPE: DNA
<213> ORGANISM: Homo sapiens

<400> SEQUENCE: 58
tgtgcgaggg agcagtggct ggtcctatct tactttgact ac                       42

<210> SEQ ID NO 59
<211> LENGTH: 14
<212> TYPE: PRT
<213> ORGANISM: Homo sapiens

<400> SEQUENCE: 59

Cys Ala Arg Glu Gln Trp Leu Val Leu Asn Tyr Phe Asp Tyr
1               5                   10

<210> SEQ ID NO 60
<211> LENGTH: 42
<212> TYPE: DNA
<213> ORGANISM: Homo sapiens

<400> SEQUENCE: 60
tgtgcgaggg agcagtggct ggtacttaac tactttgact ac                       42

<210> SEQ ID NO 61
<211> LENGTH: 14
<212> TYPE: PRT
<213> ORGANISM: Homo sapiens

<400> SEQUENCE: 61

Cys Ala Arg Glu Gln Trp Leu Ala Leu Lys Pro Phe Asp Tyr
1               5                   10

<210> SEQ ID NO 62
<211> LENGTH: 42
<212> TYPE: DNA
<213> ORGANISM: Homo sapiens

<400> SEQUENCE: 62
tgtgcgagag agcagtggct ggccttaaaa ccctttgact ac                       42

<210> SEQ ID NO 63
<211> LENGTH: 15
<212> TYPE: PRT
<213> ORGANISM: Homo sapiens

<400> SEQUENCE: 63

Cys Ala Arg Lys Gln Trp Leu Ala Ile Val Asn Tyr Phe Asp Tyr
1               5                   10                  15

<210> SEQ ID NO 64
<211> LENGTH: 45
<212> TYPE: DNA
<213> ORGANISM: Homo sapiens

<400> SEQUENCE: 64
tgtgcgagaa agcagtggct ggccatcgtc aactactttg actac            45

<210> SEQ ID NO 65
<211> LENGTH: 14
<212> TYPE: PRT
<213> ORGANISM: Homo sapiens

<400> SEQUENCE: 65

Cys Ala Arg Glu Gln Trp Leu Gly Leu Pro Thr Phe Asp Tyr
1               5                   10

<210> SEQ ID NO 66
<211> LENGTH: 42
<212> TYPE: DNA
<213> ORGANISM: Homo sapiens

<400> SEQUENCE: 66
tgtgcgagag agcagtggct gggtctacct acctttgact ac               42

<210> SEQ ID NO 67
<211> LENGTH: 15
<212> TYPE: PRT
<213> ORGANISM: Homo sapiens

<400> SEQUENCE: 67

Cys Ala Arg Val Gln Trp Leu Gly Leu Thr Gly Pro Asn Asp Tyr
1               5                   10                  15

<210> SEQ ID NO 68
<211> LENGTH: 45
<212> TYPE: DNA
<213> ORGANISM: Homo sapiens

<400> SEQUENCE: 68
tgtgctaggg ttcagtggct gggcctgacg gggccgaatg actac            45

<210> SEQ ID NO 69
<211> LENGTH: 14
<212> TYPE: PRT
<213> ORGANISM: Homo sapiens

<400> SEQUENCE: 69

Cys Ala Arg Gly Gln Trp Leu Val Ile Leu Asn Phe Asp Tyr
1               5                   10

<210> SEQ ID NO 70
<211> LENGTH: 42
<212> TYPE: DNA
<213> ORGANISM: Homo sapiens

<400> SEQUENCE: 70
tgtgcgaggg gacagtggct ggtcatccta aactttgact ac               42

<210> SEQ ID NO 71

<211> LENGTH: 14
<212> TYPE: PRT
<213> ORGANISM: Homo sapiens

<400> SEQUENCE: 71

Cys Ala Arg Asp Gln Trp Leu Pro Thr Asn Asn Phe Asp Tyr
1               5                   10

<210> SEQ ID NO 72
<211> LENGTH: 42
<212> TYPE: DNA
<213> ORGANISM: Homo sapiens

<400> SEQUENCE: 72
tgtgcgagag atcagtggct gcccacgaac aactttgact ac        42

<210> SEQ ID NO 73
<211> LENGTH: 14
<212> TYPE: PRT
<213> ORGANISM: Homo sapiens

<400> SEQUENCE: 73

Cys Ala Arg Glu Gln Trp Leu Val Leu Ser His Phe Asp Tyr
1               5                   10

<210> SEQ ID NO 74
<211> LENGTH: 42
<212> TYPE: DNA
<213> ORGANISM: Homo sapiens

<400> SEQUENCE: 74
tgtgcgaggg agcagtggtt ggtactatct cactttgact ac        42

<210> SEQ ID NO 75
<211> LENGTH: 11
<212> TYPE: PRT
<213> ORGANISM: Homo sapiens

<400> SEQUENCE: 75

Tyr Tyr Asp Tyr Val Trp Gly Ser Tyr Arg Tyr
1               5                   10

<210> SEQ ID NO 76
<211> LENGTH: 37
<212> TYPE: DNA
<213> ORGANISM: Homo sapiens

<400> SEQUENCE: 76
gtattatgat tacgtttggg ggagttatcg ttatacc        37

<210> SEQ ID NO 77
<211> LENGTH: 5
<212> TYPE: PRT
<213> ORGANISM: Homo sapiens

<400> SEQUENCE: 77

Asp Ala Phe Asp Ile
1               5

<210> SEQ ID NO 78
<211> LENGTH: 16
<212> TYPE: DNA
<213> ORGANISM: Homo sapiens

<400> SEQUENCE: 78

```
tgatgctttt gatgtc                                                    16

<210> SEQ ID NO 79
<211> LENGTH: 22
<212> TYPE: PRT
<213> ORGANISM: Homo sapiens

<400> SEQUENCE: 79

Cys Ala Arg Gly Gly Asp Tyr Asp Tyr Val Trp Gly Ser Tyr Arg Ser
1               5                   10                  15

Asn Asp Ala Phe Asp Ile
            20

<210> SEQ ID NO 80
<211> LENGTH: 66
<212> TYPE: DNA
<213> ORGANISM: Homo sapiens

<400> SEQUENCE: 80
tgtgcgagag gaggcgatta tgattacgtt tgggggagtt atcgttctaa tgatgctttt   60
gatatc                                                              66

<210> SEQ ID NO 81
<211> LENGTH: 22
<212> TYPE: PRT
<213> ORGANISM: Homo sapiens

<400> SEQUENCE: 81

Cys Ala Arg Gly Gly Ile Tyr Asp Tyr Val Trp Gly Ser Tyr Arg Pro
1               5                   10                  15

Asn Asp Ala Phe Asp Ile
            20

<210> SEQ ID NO 82
<211> LENGTH: 66
<212> TYPE: DNA
<213> ORGANISM: Homo sapiens

<400> SEQUENCE: 82
tgtgcgagag ggggtattta tgattacgtt tgggggagtt atcgtccgaa tgatgctttt   60
gatatc                                                              66

<210> SEQ ID NO 83
<211> LENGTH: 22
<212> TYPE: PRT
<213> ORGANISM: Homo sapiens

<400> SEQUENCE: 83

Cys Ala Arg Gly Gly Asn Tyr Asp Tyr Ile Trp Gly Ser Tyr Arg Ser
1               5                   10                  15

Asn Asp Ala Phe Asp Ile
            20

<210> SEQ ID NO 84
<211> LENGTH: 66
<212> TYPE: DNA
<213> ORGANISM: Homo sapiens

<400> SEQUENCE: 84
tgtgcgagag gaggcaatta tgattacatt tggggagtt atcgttccaa tgatgctttt    60
```

```
gatatc                                                             66
```

<210> SEQ ID NO 85
<211> LENGTH: 22
<212> TYPE: PRT
<213> ORGANISM: Homo sapiens

<400> SEQUENCE: 85

Cys Ala Arg Gly Gly Asp Tyr Asp Tyr Val Trp Gly Ser Tyr Arg Pro
1               5                   10                  15

Asn Asp Ala Phe Asp Ile
            20

<210> SEQ ID NO 86
<211> LENGTH: 66
<212> TYPE: DNA
<213> ORGANISM: Homo sapiens

<400> SEQUENCE: 86

```
tgtgcgagag gggggattat tgattacgtt tggggagtt atcgtccgaa tgatgctttt   60
gatatc                                                             66
```

<210> SEQ ID NO 87
<211> LENGTH: 22
<212> TYPE: PRT
<213> ORGANISM: Homo sapiens

<400> SEQUENCE: 87

Cys Ala Arg Gly Gly Asn Tyr Asp Tyr Ile Trp Gly Ser Tyr Arg Ser
1               5                   10                  15

Asn Asp Ala Phe Asp Ile
            20

<210> SEQ ID NO 88
<211> LENGTH: 66
<212> TYPE: DNA
<213> ORGANISM: Homo sapiens

<400> SEQUENCE: 88

```
tgtgcgagag gaggcaatta tgattacatt tggggagtt atcgttccaa tgatgctttt   60
gatatc                                                             66
```

<210> SEQ ID NO 89
<211> LENGTH: 9
<212> TYPE: PRT
<213> ORGANISM: Homo sapiens

<400> SEQUENCE: 89

Ile Thr Met Val Arg Gly Val Ile Ile
1               5

<210> SEQ ID NO 90
<211> LENGTH: 31
<212> TYPE: DNA
<213> ORGANISM: Homo sapiens

<400> SEQUENCE: 90

```
gtattactat ggttcgggga gttattataa c                                 31
```

<210> SEQ ID NO 91
<211> LENGTH: 11
<212> TYPE: DNA

<213> ORGANISM: Homo sapiens

<400> SEQUENCE: 91
attactacta c    11

<210> SEQ ID NO 92
<211> LENGTH: 15
<212> TYPE: PRT
<213> ORGANISM: Homo sapiens

<400> SEQUENCE: 92

Cys Ala Glu Gly Met Val Gln Gly Val Ile Gly Ile Tyr Tyr Tyr
1               5                   10                  15

<210> SEQ ID NO 93
<211> LENGTH: 45
<212> TYPE: DNA
<213> ORGANISM: Homo sapiens

<400> SEQUENCE: 93
tgtgcggagg gtatggttca gggagttatt ggaatttact actac    45

<210> SEQ ID NO 94
<211> LENGTH: 15
<212> TYPE: PRT
<213> ORGANISM: Homo sapiens

<400> SEQUENCE: 94

Cys Ala Arg Ser Met Val Gln Gly Val Ile Asn Val Leu Tyr Tyr
1               5                   10                  15

<210> SEQ ID NO 95
<211> LENGTH: 45
<212> TYPE: DNA
<213> ORGANISM: Homo sapiens

<400> SEQUENCE: 95
tgtgcgaggt ctatggttca gggagttatt aacgtcctct actac    45

<210> SEQ ID NO 96
<211> LENGTH: 15
<212> TYPE: PRT
<213> ORGANISM: Homo sapiens

<400> SEQUENCE: 96

Cys Ala Arg Ala Met Val Arg Gly Val Ile His Leu Asp Tyr Tyr
1               5                   10                  15

<210> SEQ ID NO 97
<211> LENGTH: 45
<212> TYPE: DNA
<213> ORGANISM: Homo sapiens

<400> SEQUENCE: 97
tgtgcgaggg ctatggttcg gggagttatt cacttggact actac    45

<210> SEQ ID NO 98
<211> LENGTH: 15
<212> TYPE: PRT
<213> ORGANISM: Homo sapiens

<400> SEQUENCE: 98

Cys Ala Arg Val Met Val Arg Gly Val Ile Ser Leu Asp Tyr Tyr
1               5                   10                  15

```
<210> SEQ ID NO 99
<211> LENGTH: 45
<212> TYPE: DNA
<213> ORGANISM: Homo sapiens

<400> SEQUENCE: 99
tgtgcgagag ttatggttcg gggagttatt tccctggact actac          45

<210> SEQ ID NO 100
<211> LENGTH: 11
<212> TYPE: PRT
<213> ORGANISM: Homo sapiens

<400> SEQUENCE: 100

Tyr Tyr Tyr Tyr Tyr Gly Met Asp Val Trp Gly
1               5                   10

<210> SEQ ID NO 101
<211> LENGTH: 35
<212> TYPE: DNA
<213> ORGANISM: Homo sapiens

<400> SEQUENCE: 101
attactacta ctactacggt atggacgtct ggggc                35

<210> SEQ ID NO 102
<211> LENGTH: 12
<212> TYPE: PRT
<213> ORGANISM: Homo sapiens

<400> SEQUENCE: 102

Cys Ala Arg Asp Ala Asn Gly Met Asp Val Trp Gly
1               5                   10

<210> SEQ ID NO 103
<211> LENGTH: 36
<212> TYPE: DNA
<213> ORGANISM: Homo sapiens

<400> SEQUENCE: 103
tgtgcgagag atgcgaatgg aatggacgtc tggggc                36

<210> SEQ ID NO 104
<211> LENGTH: 12
<212> TYPE: PRT
<213> ORGANISM: Homo sapiens

<400> SEQUENCE: 104

Cys Ala Arg Asp Arg Asn Gly Met Asp Val Trp Gly
1               5                   10

<210> SEQ ID NO 105
<211> LENGTH: 36
<212> TYPE: DNA
<213> ORGANISM: Homo sapiens

<400> SEQUENCE: 105
tgtgcgagag atcggaacgg tatggacgtc tggggc                36

<210> SEQ ID NO 106
<211> LENGTH: 12
<212> TYPE: PRT
<213> ORGANISM: Homo sapiens
```

<400> SEQUENCE: 106

Cys Ala Arg Asp Gln Asn Gly Met Asp Val Trp Gly
1               5                   10

<210> SEQ ID NO 107
<211> LENGTH: 36
<212> TYPE: DNA
<213> ORGANISM: Homo sapiens

<400> SEQUENCE: 107
tgtgcgagag atcaaaacgg tatggacgtc tggggc                36

<210> SEQ ID NO 108
<211> LENGTH: 12
<212> TYPE: PRT
<213> ORGANISM: Homo sapiens

<400> SEQUENCE: 108

Cys Ala Ser Asp Arg Asn Gly Met Asp Val Trp Gly
1               5                   10

<210> SEQ ID NO 109
<211> LENGTH: 36
<212> TYPE: DNA
<213> ORGANISM: Homo sapiens

<400> SEQUENCE: 109
tgtgcgagcg atcgaaacgg tatggacgtc tggggc                36

<210> SEQ ID NO 110
<211> LENGTH: 12
<212> TYPE: PRT
<213> ORGANISM: Homo sapiens

<400> SEQUENCE: 110

Cys Ala Arg Glu Pro Tyr Gly Met Asp Val Trp Gly
1               5                   10

<210> SEQ ID NO 111
<211> LENGTH: 36
<212> TYPE: DNA
<213> ORGANISM: Homo sapiens

<400> SEQUENCE: 111
tgtgcgagag agccatacgg tatggacgtc tggggc                36

<210> SEQ ID NO 112
<211> LENGTH: 12
<212> TYPE: PRT
<213> ORGANISM: Homo sapiens

<400> SEQUENCE: 112

Cys Ala Arg Asp Gly Ser Gly Met Asp Val Trp Gly
1               5                   10

<210> SEQ ID NO 113
<211> LENGTH: 36
<212> TYPE: DNA
<213> ORGANISM: Homo sapiens

<400> SEQUENCE: 113
tgtgcgagag atggctccgg tatggacgtc tggggc                36

```
<210> SEQ ID NO 114
<211> LENGTH: 12
<212> TYPE: PRT
<213> ORGANISM: Homo sapiens

<400> SEQUENCE: 114

Cys Ala Arg Asp Ala Asn Gly Met Asp Val Trp Gly
1               5                   10

<210> SEQ ID NO 115
<211> LENGTH: 36
<212> TYPE: DNA
<213> ORGANISM: Homo sapiens

<400> SEQUENCE: 115
tgtgcgagag atgctaacgg catggacgtc tggggc                                 36

<210> SEQ ID NO 116
<211> LENGTH: 14
<212> TYPE: PRT
<213> ORGANISM: Homo sapiens

<400> SEQUENCE: 116

Cys Ala Arg Gln Gln Trp Leu Gly Gly Asp Tyr Phe Asp Tyr
1               5                   10

<210> SEQ ID NO 117
<211> LENGTH: 42
<212> TYPE: DNA
<213> ORGANISM: Homo sapiens

<400> SEQUENCE: 117
tgtgcgaggc agcagtggct gggtggcgac tactttgact ac                          42

<210> SEQ ID NO 118
<211> LENGTH: 14
<212> TYPE: PRT
<213> ORGANISM: Homo sapiens

<400> SEQUENCE: 118

Cys Ala Arg Arg Gln Trp Leu Ala Leu Gly His Phe Asp Tyr
1               5                   10

<210> SEQ ID NO 119
<211> LENGTH: 42
<212> TYPE: DNA
<213> ORGANISM: Homo sapiens

<400> SEQUENCE: 119
tgtgcgagaa ggcagtggct ggccctaggc cactttgact ac                          42

<210> SEQ ID NO 120
<211> LENGTH: 14
<212> TYPE: PRT
<213> ORGANISM: Homo sapiens

<400> SEQUENCE: 120

Cys Ala Arg Gln Gln Trp Phe Gly Val Tyr Tyr Phe Asp Tyr
1               5                   10

<210> SEQ ID NO 121
<211> LENGTH: 42
<212> TYPE: DNA
<213> ORGANISM: Homo sapiens
```

```
<400> SEQUENCE: 121
tgtgcgagac agcaatggtt cggcgtgtac tactttgact ac          42

<210> SEQ ID NO 122
<211> LENGTH: 14
<212> TYPE: PRT
<213> ORGANISM: Homo sapiens

<400> SEQUENCE: 122

Cys Ala Arg Gln Gln Trp Leu Val Leu Pro Tyr Phe Asp Tyr
1               5                   10

<210> SEQ ID NO 123
<211> LENGTH: 42
<212> TYPE: DNA
<213> ORGANISM: Homo sapiens

<400> SEQUENCE: 123
tgtgcgagac agcagtggct ggtacttcca tactttgact ac          42

<210> SEQ ID NO 124
<211> LENGTH: 14
<212> TYPE: PRT
<213> ORGANISM: Homo sapiens

<400> SEQUENCE: 124

Cys Ala Arg Glu Gln Trp Leu Ile Val Thr His Phe Asp Tyr
1               5                   10

<210> SEQ ID NO 125
<211> LENGTH: 42
<212> TYPE: DNA
<213> ORGANISM: Homo sapiens

<400> SEQUENCE: 125
tgtgcgagag agcagtggct catagtaact cactttgact ac          42

<210> SEQ ID NO 126
<211> LENGTH: 14
<212> TYPE: PRT
<213> ORGANISM: Homo sapiens

<400> SEQUENCE: 126

Cys Ala Arg Gln Gln Trp Leu Val Leu Asp Tyr Phe Asp Tyr
1               5                   10

<210> SEQ ID NO 127
<211> LENGTH: 42
<212> TYPE: DNA
<213> ORGANISM: Homo sapiens

<400> SEQUENCE: 127
tgtgcgagac agcagtggct ggtgttggac tactttgact ac          42

<210> SEQ ID NO 128
<211> LENGTH: 14
<212> TYPE: PRT
<213> ORGANISM: Homo sapiens

<400> SEQUENCE: 128

Cys Ala Arg Glu Gln Trp Leu Val Leu Ser Asn Phe Asp Tyr
1               5                   10
```

```
<210> SEQ ID NO 129
<211> LENGTH: 14
<212> TYPE: PRT
<213> ORGANISM: Homo sapiens

<400> SEQUENCE: 129

Cys Ala Arg Glu Gln Trp Leu Val Leu Ser Tyr Phe Asp Tyr
1               5                   10

<210> SEQ ID NO 130
<211> LENGTH: 42
<212> TYPE: DNA
<213> ORGANISM: Homo sapiens

<400> SEQUENCE: 130
tgtgcgaggg agcagtggct ggtcctatct tactttgact ac                              42

<210> SEQ ID NO 131
<211> LENGTH: 14
<212> TYPE: PRT
<213> ORGANISM: Homo sapiens

<400> SEQUENCE: 131

Cys Ala Arg Glu Gln Trp Leu Val Leu Asn Tyr Phe Asp Tyr
1               5                   10

<210> SEQ ID NO 132
<211> LENGTH: 42
<212> TYPE: DNA
<213> ORGANISM: Homo sapiens

<400> SEQUENCE: 132
tgtgcgaggg agcagtggct ggtacttaac tactttgact ac                              42

<210> SEQ ID NO 133
<211> LENGTH: 14
<212> TYPE: PRT
<213> ORGANISM: Homo sapiens

<400> SEQUENCE: 133

Cys Ala Arg Glu Gln Trp Leu Ala Leu Lys Pro Phe Asp Tyr
1               5                   10

<210> SEQ ID NO 134
<211> LENGTH: 42
<212> TYPE: DNA
<213> ORGANISM: Homo sapiens

<400> SEQUENCE: 134
tgtgcgagag agcagtggct ggccttaaaa ccctttgact ac                              42

<210> SEQ ID NO 135
<211> LENGTH: 15
<212> TYPE: PRT
<213> ORGANISM: Homo sapiens

<400> SEQUENCE: 135

Cys Ala Arg Lys Gln Trp Leu Ala Ile Val Asn Tyr Phe Asp Tyr
1               5                   10                  15

<210> SEQ ID NO 136
<211> LENGTH: 45
<212> TYPE: DNA
<213> ORGANISM: Homo sapiens
```

<210> SEQ ID NO 136

<400> SEQUENCE: 136
tgtgcgagaa agcagtggct ggccatcgtc aactactttg actac            45

<210> SEQ ID NO 137
<211> LENGTH: 14
<212> TYPE: PRT
<213> ORGANISM: Homo sapiens

<400> SEQUENCE: 137

Cys Ala Arg Glu Gln Trp Leu Gly Leu Pro Thr Phe Asp Tyr
1               5                   10

<210> SEQ ID NO 138
<211> LENGTH: 42
<212> TYPE: DNA
<213> ORGANISM: Homo sapiens

<400> SEQUENCE: 138
tgtgcgagag agcagtggct gggtctacct acctttgact ac            42

<210> SEQ ID NO 139
<211> LENGTH: 15
<212> TYPE: PRT
<213> ORGANISM: Homo sapiens

<400> SEQUENCE: 139

Cys Ala Arg Val Gln Trp Leu Gly Leu Thr Gly Pro Asn Asp Tyr
1               5                   10                  15

<210> SEQ ID NO 140
<211> LENGTH: 45
<212> TYPE: DNA
<213> ORGANISM: Homo sapiens

<400> SEQUENCE: 140
tgtgctaggg ttcagtggct gggcctgacg gggccgaatg actac            45

<210> SEQ ID NO 141
<211> LENGTH: 14
<212> TYPE: PRT
<213> ORGANISM: Homo sapiens

<400> SEQUENCE: 141

Cys Ala Arg Gly Gln Trp Leu Val Ile Leu Asn Phe Asp Tyr
1               5                   10

<210> SEQ ID NO 142
<211> LENGTH: 42
<212> TYPE: DNA
<213> ORGANISM: Homo sapiens

<400> SEQUENCE: 142
tgtgcgaggg gacagtggct ggtcatccta aactttgact ac            42

<210> SEQ ID NO 143
<211> LENGTH: 14
<212> TYPE: PRT
<213> ORGANISM: Homo sapiens

<400> SEQUENCE: 143

Cys Ala Arg Asp Gln Trp Leu Pro Thr Asn Asn Phe Asp Tyr
1               5                   10

```
<210> SEQ ID NO 144
<211> LENGTH: 42
<212> TYPE: DNA
<213> ORGANISM: Homo sapiens

<400> SEQUENCE: 144
tgtgcgagag atcagtggct gcccacgaac aactttgact ac            42

<210> SEQ ID NO 145
<211> LENGTH: 14
<212> TYPE: PRT
<213> ORGANISM: Homo sapiens

<400> SEQUENCE: 145

Cys Ala Arg Glu Gln Trp Leu Val Leu Ser His Phe Asp Tyr
1               5                   10

<210> SEQ ID NO 146
<211> LENGTH: 42
<212> TYPE: DNA
<213> ORGANISM: Homo sapiens

<400> SEQUENCE: 146
tgtgcgaggg agcagtggtt ggtactatct cactttgact ac            42

<210> SEQ ID NO 147
<211> LENGTH: 14
<212> TYPE: PRT
<213> ORGANISM: Homo sapiens

<400> SEQUENCE: 147

Cys Ala Arg Gln Gln Trp Leu Gly Gly Asp Tyr Phe Asp Tyr
1               5                   10

<210> SEQ ID NO 148
<211> LENGTH: 42
<212> TYPE: DNA
<213> ORGANISM: Homo sapiens

<400> SEQUENCE: 148
tgtgcgaggc agcagtggct gggtggcgac tactttgact ac            42

<210> SEQ ID NO 149
<211> LENGTH: 14
<212> TYPE: PRT
<213> ORGANISM: Homo sapiens

<400> SEQUENCE: 149

Cys Ala Arg Arg Gln Trp Leu Ala Leu Gly His Phe Asp Tyr
1               5                   10

<210> SEQ ID NO 150
<211> LENGTH: 42
<212> TYPE: DNA
<213> ORGANISM: Homo sapiens

<400> SEQUENCE: 150
tgtgcgagaa ggcagtggct ggccctaggc cactttgact ac            42

<210> SEQ ID NO 151
<211> LENGTH: 14
<212> TYPE: PRT
<213> ORGANISM: Homo sapiens
```

```
<400> SEQUENCE: 151

Cys Ala Arg Gln Gln Trp Phe Gly Val Tyr Tyr Phe Asp Tyr
1               5                   10

<210> SEQ ID NO 152
<211> LENGTH: 42
<212> TYPE: DNA
<213> ORGANISM: Homo sapiens

<400> SEQUENCE: 152
tgtgcgagac agcaatggtt cggcgtgtac tactttgact ac                42

<210> SEQ ID NO 153
<211> LENGTH: 14
<212> TYPE: PRT
<213> ORGANISM: Homo sapiens

<400> SEQUENCE: 153

Cys Ala Arg Gln Gln Trp Leu Val Leu Pro Tyr Phe Asp Tyr
1               5                   10

<210> SEQ ID NO 154
<211> LENGTH: 42
<212> TYPE: DNA
<213> ORGANISM: Homo sapiens

<400> SEQUENCE: 154
tgtgcgagac agcagtggct ggtacttcca tactttgact ac                42

<210> SEQ ID NO 155
<211> LENGTH: 14
<212> TYPE: PRT
<213> ORGANISM: Homo sapiens

<400> SEQUENCE: 155

Cys Ala Arg Glu Gln Trp Leu Ile Val Thr His Phe Asp Tyr
1               5                   10

<210> SEQ ID NO 156
<211> LENGTH: 42
<212> TYPE: DNA
<213> ORGANISM: Homo sapiens

<400> SEQUENCE: 156
tgtgcgagag agcagtggct catagtaact cactttgact ac                42

<210> SEQ ID NO 157
<211> LENGTH: 14
<212> TYPE: PRT
<213> ORGANISM: Homo sapiens

<400> SEQUENCE: 157

Cys Ala Arg Gln Gln Trp Leu Val Leu Asp Tyr Phe Asp Tyr
1               5                   10

<210> SEQ ID NO 158
<211> LENGTH: 42
<212> TYPE: DNA
<213> ORGANISM: Homo sapiens

<400> SEQUENCE: 158
tgtgcgagac agcagtggct ggtgttggac tactttgact ac                42
```

```
<210> SEQ ID NO 159
<211> LENGTH: 14
<212> TYPE: PRT
<213> ORGANISM: Homo sapiens

<400> SEQUENCE: 159

Cys Ala Arg Glu Gln Trp Leu Val Leu Ser Asn Phe Asp Tyr
1               5                   10

<210> SEQ ID NO 160
<211> LENGTH: 126
<212> TYPE: PRT
<213> ORGANISM: Homo sapiens

<400> SEQUENCE: 160

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Asp Tyr Tyr Asp Tyr Val Trp Gly Ser Tyr Arg Tyr Asp Ala
            100                 105                 110

Phe Asp Val Trp Gly Gln Gly Thr Met Val Thr Val Ser Ser
        115                 120                 125

<210> SEQ ID NO 161
<211> LENGTH: 128
<212> TYPE: PRT
<213> ORGANISM: Homo sapiens

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Asp Tyr Asp Tyr Val Trp Gly Ser Tyr Arg Ser Asn
            100                 105                 110

Asp Ala Phe Asp Val Trp Gly Gln Gly Thr Met Val Thr Val Ser Ser
        115                 120                 125

<210> SEQ ID NO 162
<211> LENGTH: 128
<212> TYPE: PRT
<213> ORGANISM: Homo sapiens
```

<400> SEQUENCE: 162

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Ile Tyr Asp Tyr Val Trp Gly Ser Tyr Arg Pro Asn
            100                 105                 110

Asp Ala Phe Asp Val Trp Gly Gln Gly Thr Met Val Thr Val Ser Ser
        115                 120                 125

<210> SEQ ID NO 163
<211> LENGTH: 128
<212> TYPE: PRT
<213> ORGANISM: Homo sapiens

<400> SEQUENCE: 163

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Pro Tyr Asp Tyr Val Trp Gly Ser Tyr Arg Pro Asn
            100                 105                 110

Asp Ala Phe Asp Val Trp Gly Gln Gly Thr Met Val Thr Val Ser Ser
        115                 120                 125

<210> SEQ ID NO 164
<211> LENGTH: 128
<212> TYPE: PRT
<213> ORGANISM: Homo sapiens

<400> SEQUENCE: 164

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Trp Tyr Asp Tyr Ile Trp Gly Ser Tyr Arg Ser Asn
            100                 105                 110

Asp Ala Phe Asp Val Trp Gly Gln Gly Thr Met Val Thr Val Ser Ser
            115                 120                 125

<210> SEQ ID NO 165
<211> LENGTH: 123
<212> TYPE: PRT
<213> ORGANISM: Homo sapiens

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Asp Tyr Asp Tyr Val Trp Gly Ser Tyr Arg Pro Asn
            100                 105                 110

Asp Ala Phe Asp Val Trp Gly Gln Gly Thr Ile
            115                 120

<210> SEQ ID NO 166
<211> LENGTH: 128
<212> TYPE: PRT
<213> ORGANISM: Homo sapiens

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Asn Tyr Asp Tyr Ile Trp Gly Ser Tyr Arg Ser Asn
            100                 105                 110

Asp Ala Phe Asp Val Trp Gly Gln Gly Thr Val Val Thr Val Ser Ser
            115                 120                 125

<210> SEQ ID NO 167
<211> LENGTH: 128

```
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (111)..(111)
<223> OTHER INFORMATION: X = Ser or Pro

<400> SEQUENCE: 167
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Asn Glu Leu Ser Ser Leu Arg Ser Glu Asp Thr Ala Val Tyr Tyr Cys
                85                  90                  95

Ala Arg Gly Gly Asp Tyr Asp Tyr Val Trp Gly Ser Tyr Arg Xaa Asn
            100                 105                 110

Asp Ala Phe Asp Val Trp Gly Gln Gly Thr Met Val Thr Val Ser Ser
        115                 120                 125

```
<210> SEQ ID NO 168
<211> LENGTH: 128
<212> TYPE: PRT
<213> ORGANISM: Homo sapiens

<400> SEQUENCE: 168
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Val Val Val Pro Ala Ala Ile Tyr Tyr Tyr Tyr
            100                 105                 110

Tyr Gly Met Asp Val Trp Gly Gln Gly Thr Thr Val Thr Val Ser Ser
        115                 120                 125

```
<210> SEQ ID NO 169
<211> LENGTH: 129
<212> TYPE: PRT
<213> ORGANISM: Homo sapiens

<400> SEQUENCE: 169
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
            20                  25                  30
Ala Ile Ser Trp Val Arg Gln Ala Pro Gly Gln Gly Leu Glu Trp Met
         35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                 85                  90                  95
Ala Arg Gly Gly Asp Ile Val Val Pro Ala Ala Met Ser Tyr Tyr
            100                 105                 110
Tyr Tyr Gly Met Asp Val Trp Gly Gln Gly Thr Thr Val Thr Val Ser
            115                 120                 125
Ser
```

<210> SEQ ID NO 170
<211> LENGTH: 129
<212> TYPE: PRT
<213> ORGANISM: Homo sapiens

<400> SEQUENCE: 170

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
         35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                 85                  90                  95
Ala Arg Gly Ala Asp Ile Val Val Pro Ala Ala Met Gly Tyr Tyr
            100                 105                 110
Tyr Tyr Gly Met Asp Val Trp Gly Gln Gly Thr Thr Val Thr Val Ser
            115                 120                 125
Ser
```

<210> SEQ ID NO 171
<211> LENGTH: 129
<212> TYPE: PRT
<213> ORGANISM: Homo sapiens

<400> SEQUENCE: 171

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
         35                  40                  45
Gly Gly Ile Ile Pro Ile Phe Gly Thr Ala Asn Tyr Ala Gln Lys Phe
 50                  55                  60
Gln Gly Arg Val Thr Ile Thr Ala Asp Glu Ser Thr Ser Thr Ala Tyr
65                  70                  75                  80
```

Met Glu Leu Ser Ser Leu Arg Ser Glu Asp Thr Ala Val Tyr Tyr Cys
                85                  90                  95

Ala Arg Gly Gly Asp Ile Val Val Pro Ala Ala Met Arg Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 172
<211> LENGTH: 127
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (108)..(108)
<223> OTHER INFORMATION: X = Arg, Gly or Ser

<400> SEQUENCE: 172

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asp Ile Val Val Pro Ala Ala Xaa Tyr Tyr Tyr Tyr
            100                 105                 110

Gly Met Asp Val Trp Gly Gln Gly Thr Thr Val Thr Val Ser Ser
        115                 120                 125

<210> SEQ ID NO 173
<211> LENGTH: 126
<212> TYPE: PRT
<213> ORGANISM: Homo sapiens

<400> SEQUENCE: 173

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Met Val Arg Gly Val Ile Ile Tyr Tyr Tyr Tyr Gly
            100                 105                 110

Met Asp Val Trp Gly Gln Gly Thr Thr Val Thr Val Ser Ser 115                 120                 125

<210> SEQ ID NO 174
<211> LENGTH: 127
<212> TYPE: PRT
<213> ORGANISM: Homo sapiens

<400> SEQUENCE: 174

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Met Val Gln Gly Val Ile Gln Tyr Tyr Tyr Tyr Tyr Tyr
            100                 105                 110

Tyr Met Asp Val Trp Gly Lys Gly Thr Thr Val Thr Val Ser Ser
        115                 120                 125

<210> SEQ ID NO 175
<211> LENGTH: 127
<212> TYPE: PRT
<213> ORGANISM: Homo sapiens

<400> SEQUENCE: 175

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Met Val Arg Gly Val Ile Ile Tyr Tyr Tyr Tyr Tyr Tyr
            100                 105                 110

Tyr Met Asp Val Trp Gly Lys Gly Thr Thr Val Thr Val Ser Ser
        115                 120                 125

<210> SEQ ID NO 176
<211> LENGTH: 127
<212> TYPE: PRT
<213> ORGANISM: Homo sapiens

<400> SEQUENCE: 176

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Met Val Arg Gly Val Ile Ile Tyr Tyr Tyr Tyr Tyr Tyr
                100                 105                 110

Tyr Met Asp Val Trp Gly Lys Gly Thr Thr Val Thr Val Ser Ser
            115                 120                 125
```

<210> SEQ ID NO 177
<211> LENGTH: 127
<212> TYPE: PRT
<213> ORGANISM: Homo sapiens

<400> SEQUENCE: 177

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Glu Gly Met Val Gln Gly Val Ile Gly Ile Tyr Tyr Tyr Tyr Tyr
                100                 105                 110

Gly Met Asp Val Trp Gly Gln Gly Thr Thr Val Thr Val Ser Ser
            115                 120                 125
```

<210> SEQ ID NO 178
<211> LENGTH: 126
<212> TYPE: PRT
<213> ORGANISM: Homo sapiens

<400> SEQUENCE: 178

```
Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Met Val Arg Gly Val Ile Ile Tyr Tyr Tyr Tyr Tyr Gly
                100                 105                 110
```

```
Met Asp Val Trp Gly Gln Gly Thr Thr Val Thr Val Ser Ser
        115                 120                 125
```

<210> SEQ ID NO 179
<211> LENGTH: 127
<212> TYPE: PRT
<213> ORGANISM: Homo sapiens

<400> SEQUENCE: 179

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Met Val Arg Gly Val Ile His Leu Asp Tyr Tyr Tyr Tyr
            100                 105                 110

Tyr Met Asp Val Trp Gly Lys Gly Thr Thr Val Thr Val Ser Ser
        115                 120                 125
```

<210> SEQ ID NO 180
<211> LENGTH: 127
<212> TYPE: PRT
<213> ORGANISM: Homo sapiens

<400> SEQUENCE: 180

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Met Val Arg Gly Val Ile Ser Leu Asp Tyr Tyr Tyr Tyr
            100                 105                 110

Tyr Met Asp Val Trp Gly Lys Gly Thr Leu Val Thr Val Ser Ser
        115                 120                 125
```

<210> SEQ ID NO 181
<211> LENGTH: 127
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (99)..(99)
<223> OTHER INFORMATION: X = Val, Ala, Ser, Gly or Asp

```
<220> FEATURE:
<221> NAME/KEY: MISC_FEATURE
<222> LOCATION: (107)..(107)
<223> OTHER INFORMATION: X = Leu, Val, Ile, Tyr or Thr

<400> SEQUENCE: 181

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Met Val Arg Gly Val Ile Thr Xaa Tyr Tyr Tyr Tyr Tyr
            100                 105                 110

Tyr Met Asp Val Trp Gly Lys Gly Thr Thr Val Thr Val Ser Ser
        115                 120                 125

<210> SEQ ID NO 182
<211> LENGTH: 124
<212> TYPE: PRT
<213> ORGANISM: Homo sapiens

<400> SEQUENCE: 182

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Val Asp Thr Ala Met Val Tyr Tyr Tyr Tyr Gly Met Asp
            100                 105                 110

Val Trp Gly Gln Gly Thr Thr Val Thr Val Ser Ser
        115                 120

<210> SEQ ID NO 183
<211> LENGTH: 126
<212> TYPE: PRT
<213> ORGANISM: Homo sapiens

<400> SEQUENCE: 183

Gln Leu Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Ser Pro Gly Lys Gly Leu Glu Trp Ile
        35                  40                  45
```

Gly Glu Ile Asn His Ser Gly Ser Thr Thr Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                 85                  90                  95

Arg Gly Tyr Gly Asp Thr Pro Thr Ile Arg Arg Tyr Tyr Tyr Tyr Gly
            100                 105                 110

Met Asp Val Trp Gly Gln Gly Thr Arg Val Thr Val Ser Ser
            115                 120                 125

<210> SEQ ID NO 184
<211> LENGTH: 126
<212> TYPE: PRT
<213> ORGANISM: Homo sapiens

<400> SEQUENCE: 184

Gln Val Gln Leu Gln Gln Trp Gly Ala Gly Leu Leu Lys Pro Ser Glu
 1               5                  10                  15

Thr Leu Ser Leu Met Cys Ala Val Tyr Gly Glu Ser Phe Ser Gly Tyr
                 20                  25                  30

Tyr Trp Thr Trp Ile Arg Gln Ser Pro Gly Lys Gly Leu Glu Trp Ile
             35                  40                  45

Gly Glu Ile Asn His Ser Gly Ser Thr Thr Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Ala Ala Ile Tyr Tyr Cys Ala
                 85                  90                  95

Arg Gly Tyr Ala Asp Thr Pro Val Phe Arg Arg Tyr Tyr Tyr Tyr Gly
            100                 105                 110

Met Asp Val Trp Ala Lys Gly Thr Arg Val Thr Val Ser Ser
            115                 120                 125

<210> SEQ ID NO 185
<211> LENGTH: 126
<212> TYPE: PRT
<213> ORGANISM: Homo sapiens

<400> SEQUENCE: 185

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Glu Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
 65                  70                  75                  80

Lys Leu Thr Ser Val Thr Ala Ala Asp Thr Ala Val Tyr Phe Cys Ala
                 85                  90                  95

Arg Gly Asn Gly Asp Thr Pro Met Leu Lys Arg Tyr Tyr Tyr Tyr Gly
            100                 105                 110

Leu Asp Val Trp Gly Gln Gly Thr Thr Val Thr Val Ser Ser
            115                 120                 125

<210> SEQ ID NO 186
<211> LENGTH: 126
<212> TYPE: PRT
<213> ORGANISM: Homo sapiens

<400> SEQUENCE: 186

Gln Val Gln Leu Gln Gln Trp Gly Ala Gly Leu Leu Lys Pro Ser Glu
1               5                   10                  15

Thr Leu Ala Leu Thr Cys Ala Val Tyr Gly Ser Phe Ser Gly Phe
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn His Ser Pro Ser Leu Arg
    50                  55                  60

Ser Arg Val Thr Ile Ser Val Asp Thr Ser Lys Asn Gln Phe Ser Leu
65                  70                  75                  80

Lys Leu Lys Ser Val Thr Ala Ala Asp Thr Ala Val Tyr Tyr Cys Ala
                85                  90                  95

Arg Ala Tyr Pro Asp Thr Pro Met Val Arg Arg Tyr Tyr Tyr Ser
            100                 105                 110

Val Glu Val Trp Gly Gln Gly Thr Leu Val Thr Val Ser Ser
        115                 120                 125

<210> SEQ ID NO 187
<211> LENGTH: 120
<212> TYPE: PRT
<213> ORGANISM: Homo sapiens

<400> SEQUENCE: 187

Gln Val Gln Leu Gln Gln Trp Gly Ala Gly Leu Leu Lys Pro Ser Glu
1               5                   10                  15

Thr Leu Ser Leu Thr Cys Ala Val Tyr Val Asp Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asp Ala Ser Ser Asn Pro Ser Leu Asn
    50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg Gly Phe Pro Asp Thr Asp Val Ile Lys Arg Tyr Tyr Tyr Gly
            100                 105                 110

Pro Asp Val Trp Gly Gln Gly Thr
        115                 120

<210> SEQ ID NO 188
<211> LENGTH: 127
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (106)..(106)
<223> OTHER INFORMATION: X = Ile, Leu, Phe or Val

<400> SEQUENCE: 188

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Glu Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Gly Asp Thr Thr Pro Met Xaa Arg Arg Tyr Tyr Tyr Tyr
            100                 105                 110

Gly Met Asp Val Trp Gly Gln Gly Thr Thr Val Thr Val Ser Ser
            115                 120                 125

<210> SEQ ID NO 189
<211> LENGTH: 118
<212> TYPE: PRT
<213> ORGANISM: Homo sapiens

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Trp Leu Val Tyr Phe Asp Tyr Trp Gly Gln Gly Thr
            100                 105                 110

Leu Val Thr Val Ser Ser
        115

<210> SEQ ID NO 190
<211> LENGTH: 121
<212> TYPE: PRT
<213> ORGANISM: Homo sapiens

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

-continued

```
Met Glu Leu Ser Arg Leu Arg Ser Asp Asp Thr Ala Val Tyr Tyr Cys
            85                  90                  95

Ala Arg Glu Gln Trp Leu Val Leu Glu His Tyr Phe Asp Tyr Trp Gly
        100                 105                 110

Gln Gly Thr Leu Val Thr Val Ser Ser
        115                 120

<210> SEQ ID NO 191
<211> LENGTH: 120
<212> TYPE: PRT
<213> ORGANISM: Homo sapiens

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Gln Trp Leu Gly Ala Glu Asn Phe Asp Tyr Trp Gly Gln
        100                 105                 110

Gly Thr Leu Val Thr Val Ser Ser
        115                 120

<210> SEQ ID NO 192
<211> LENGTH: 120
<212> TYPE: PRT
<213> ORGANISM: Homo sapiens

<400> SEQUENCE: 192

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Val Gln Trp Leu Gly Leu Arg His Phe Asp Tyr Trp Gly Gln
        100                 105                 110

Gly Thr Leu Val Thr Val Ser Ser
        115                 120

<210> SEQ ID NO 193
<211> LENGTH: 120
<212> TYPE: PRT
<213> ORGANISM: Homo sapiens
```

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gln Trp Leu Val Leu Lys Asn Phe Asp Tyr Trp Gly Gln
            100                 105                 110

Gly Thr Leu Val Thr Val Ser Ser
            115                 120

<210> SEQ ID NO 194
<211> LENGTH: 120
<212> TYPE: PRT
<213> ORGANISM: Homo sapiens

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Arg Asn Pro Asn Ser Asn Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Val Gln Trp Leu Leu Leu Glu Arg Phe Asp Tyr Trp Gly Gln
            100                 105                 110

Gly Thr Leu Val Thr Val Ser Ser
            115                 120

<210> SEQ ID NO 195
<211> LENGTH: 88
<212> TYPE: PRT
<213> ORGANISM: Homo sapiens

<400> SEQUENCE: 195

Gly Tyr Thr Phe Thr Gly Tyr Tyr Met His Trp Val Arg Gln Ala Pro
1               5                   10                  15

Gly Gln Gly Leu Glu Trp Met Gly Trp Ile Asn Pro Asn Ser Gly Gly
            20                  25                  30

Thr Asn Tyr Ala Gln Glu Phe Gln Gly Arg Val Thr Met Thr Arg Asp
        35                  40                  45

Thr Ser Ile Ser Thr Ala Tyr Met Glu Leu Ser Arg Leu Arg Ser Asp
    50                  55                  60

Asp Thr Ala Val Tyr Tyr Cys Ala Arg Asp Asn Trp Leu Val Gly Leu

```
                65                   70                  75                  80
Asp Phe Asp Tyr Trp Gly Gln Gly
                    85

<210> SEQ ID NO 196
<211> LENGTH: 104
<212> TYPE: PRT
<213> ORGANISM: Homo sapiens

<400> SEQUENCE: 196

Ser Val Lys Val Ser Cys Lys Ala Ser Gly Tyr Thr Phe Thr Gly Tyr
1               5                   10                  15

Tyr Met His Trp Val Arg Gln Ala Pro Gly Gln Gly Leu Glu Trp Met
                20                  25                  30

Gly Trp Ile Asn Pro Asn Ser Gly Gly Thr Asn Tyr Ala Gln Glu Phe
            35                  40                  45

Gln Gly Arg Val Thr Met Thr Arg Asp Thr Ser Ile Ser Thr Ala Tyr
    50                  55                  60

Met Glu Leu Ser Arg Leu Arg Ser Asp Asp Thr Ala Val Tyr Tyr Cys
65                  70                  75                  80

Ala Arg Glu Gln Trp Leu Val Arg Thr Ser Phe Asp Tyr Trp Gly Gln
                85                  90                  95

Gly Thr Leu Val Thr Val Ser Ser
                100

<210> SEQ ID NO 197
<211> LENGTH: 120
<212> TYPE: PRT
<213> ORGANISM: Artificial
<220> FEATURE:
<223> OTHER INFORMATION: consensus sequence

<400> SEQUENCE: 197

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Gln Trp Leu Val Leu Glu Asn Phe Asp Tyr Trp Gly Gln
                100                 105                 110

Gly Thr Leu Val Thr Val Ser Ser
            115                 120

<210> SEQ ID NO 198
<211> LENGTH: 118
<212> TYPE: PRT
<213> ORGANISM: Homo sapiens

<400> SEQUENCE: 198

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Glu Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Met Ala Val Tyr Tyr Cys
                85                  90                  95

Ala Arg Asp Gln Trp Leu Val Tyr Phe Asp Tyr Trp Gly Gln Gly Thr
                100                 105                 110

Leu Val Thr Val Ser Ser
            115

<210> SEQ ID NO 199
<211> LENGTH: 120
<212> TYPE: PRT
<213> ORGANISM: Homo sapiens

<400> SEQUENCE: 199

Gln Val Gln Leu Val Gln Ser Gly Ala Glu Val Lys Asn Pro Gly Ala
 1               5                   10                  15

Ser Val Lys Val Ser Cys Lys Ala Ser Gly Tyr Thr Phe Ile Thr Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Glu Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Met Ala Val Tyr Tyr Cys
                85                  90                  95

Ala Arg Glu Gln Trp Leu Val Leu Ser Tyr Phe Asp Tyr Trp Gly Gln
                100                 105                 110

Gly Thr Leu Val Thr Val Ser Ser
            115                 120

<210> SEQ ID NO 200
<211> LENGTH: 119
<212> TYPE: PRT
<213> ORGANISM: Homo sapiens

<400> SEQUENCE: 200

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Glu Phe
 50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Met Ala Val Tyr Tyr Cys
                85                  90                  95

Ala Arg Glu Gln Trp Leu Val Leu Tyr Phe Asp Tyr Trp Gly Gln Gly
                100                 105                 110

Thr Leu Val Thr Val Ser Ser
        115

<210> SEQ ID NO 201
<211> LENGTH: 120
<212> TYPE: PRT
<213> ORGANISM: Homo sapiens

<400> SEQUENCE: 201

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Val His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gln Trp Leu Ala Leu Lys Pro Phe Asp Tyr Trp Gly Gln
                100                 105                 110

Gly Thr Leu Val Thr Val Ser Ser
        115                 120

<210> SEQ ID NO 202
<211> LENGTH: 121
<212> TYPE: PRT
<213> ORGANISM: Homo sapiens

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Lys Gln Trp Leu Ala Ile Val Asn Tyr Phe Asp Tyr Trp Gly
                100                 105                 110

Gln Gly Thr Leu Val Thr Val Ser Ser
            115                 120

<210> SEQ ID NO 203
<211> LENGTH: 104
<212> TYPE: PRT
<213> ORGANISM: Homo sapiens

<400> SEQUENCE: 203

Ser Val Lys Val Ser Cys Lys Ala Ser Gly Tyr Thr Gly Thr Ser Tyr

```
                1               5                   10                  15
Ala Met His Trp Val Arg Gln Ala Pro Gly Gln Arg Leu Glu Trp Met
                20                  25                  30

Gly Trp Ile Asn Ala Gly Asn Gly Asn Thr Lys Tyr Ser Gln Glu Phe
            35                  40                  45

Gln Gly Arg Val Thr Ile Thr Arg Asp Thr Ser Ala Ser Thr Ala Tyr
        50                  55                  60

Met Glu Leu Ser Ser Leu Arg Ser Glu Asp Met Ala Val Tyr Tyr Cys
65                  70                  75                  80

Ala Arg Glu Gln Trp Leu Gly Leu Pro Thr Phe Asp Tyr Trp Gly Gln
                85                  90                  95

Gly Thr Leu Val Thr Val Ser Ser
            100

<210> SEQ ID NO 204
<211> LENGTH: 104
<212> TYPE: PRT
<213> ORGANISM: Homo sapiens

<400> SEQUENCE: 204

Ser Val Lys Val Ser Cys Lys Ala Ser Gly Tyr Thr Phe Thr Ser Tyr
1               5                   10                  15

Ala Met His Trp Val Arg Gln Ala Pro Gly Gln Arg Leu Glu Trp Met
                20                  25                  30

Gly Trp Ile Asn Ala Gly Asn Gly Asn Thr Lys Tyr Ser Gln Glu Phe
            35                  40                  45

Gln Gly Arg Val Thr Ile Thr Arg Asp Thr Ser Ala Ser Thr Ala Tyr
        50                  55                  60

Met Glu Leu Ser Ser Leu Arg Ser Glu Asp Met Ala Val Tyr Tyr Cys
65                  70                  75                  80

Ala Arg Asp Gln Trp Leu Pro Thr Asn Asn Phe Asp Tyr Trp Gly Gln
                85                  90                  95

Gly Thr Leu Val Thr Val Ser Ser
            100

<210> SEQ ID NO 205
<211> LENGTH: 120
<212> TYPE: PRT
<213> ORGANISM: Artificial
<220> FEATURE:
<223> OTHER INFORMATION: consensus sequence

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Glu Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Glu Gln Trp Leu Ala Leu Asn Tyr Phe Asp Tyr Trp Gly Gln
            100                 105                 110
```

```
Gly Thr Leu Val Thr Val Ser Ser
        115                 120

<210> SEQ ID NO 206
<211> LENGTH: 118
<212> TYPE: PRT
<213> ORGANISM: Homo sapiens

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gln Trp Leu Val Tyr Phe Asp Tyr Trp Gly Gln Gly Thr
            100                 105                 110

Leu Val Thr Val Ser Ser
        115

<210> SEQ ID NO 207
<211> LENGTH: 120
<212> TYPE: PRT
<213> ORGANISM: Homo sapiens

<400> SEQUENCE: 207

His Val Gln Leu Val Gln Ser Gly Ala Glu Val Asn Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Gly Tyr
65                  70                  75                  80

Met Glu Leu Arg Ser Leu Arg Ser Asp Asp Thr Ala Val Tyr Tyr Cys
                85                  90                  95

Ala Arg Glu Gln Trp Leu Val Leu Ser His Phe Asp Tyr Trp Gly Gln
            100                 105                 110

Gly Thr Leu Val Thr Val Ser Ser
        115                 120

<210> SEQ ID NO 208
<211> LENGTH: 117
<212> TYPE: PRT
<213> ORGANISM: Homo sapiens

<400> SEQUENCE: 208

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Trp Leu Val Tyr Phe Asp Tyr Trp Gly Gln Gly Thr
            100                 105                 110

Leu Val Thr Val Ser
        115

<210> SEQ ID NO 209
<211> LENGTH: 119
<212> TYPE: PRT
<213> ORGANISM: Homo sapiens

<400> SEQUENCE: 209

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Trp Leu Val Ile Leu Asn Phe Asp Tyr Trp Gly Gln
            100                 105                 110

Gly Thr Leu Val Thr Val Ser
        115

<210> SEQ ID NO 210
<211> LENGTH: 120
<212> TYPE: PRT
<213> ORGANISM: Homo sapiens

<400> SEQUENCE: 210

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

```
Ala Arg Asp Gln Trp Val Gly Leu Thr Gly Pro Asn Asp Tyr Trp Gly
                100                 105                 110

Gln Gly Thr Leu Val Thr Val Ser
        115                 120

<210> SEQ ID NO 211
<211> LENGTH: 120
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (102)..(102)
<223> OTHER INFORMATION: X = Val or Leu
<220> FEATURE:
<221> NAME/KEY: MISC_FEATURE
<222> LOCATION: (103)..(103)
<223> OTHER INFORMATION: X = Gly or Val
<220> FEATURE:
<221> NAME/KEY: MISC_FEATURE
<222> LOCATION: (104)..(104)
<223> OTHER INFORMATION: X = Leu or Ile
<220> FEATURE:
<221> NAME/KEY: MISC_FEATURE
<222> LOCATION: (105)..(105)
<223> OTHER INFORMATION: X = Thr or Leu
<220> FEATURE:
<221> NAME/KEY: MISC_FEATURE
<222> LOCATION: (106)..(106)
<223> OTHER INFORMATION: X = Gly or Asn
<220> FEATURE:
<221> NAME/KEY: MISC_FEATURE
<222> LOCATION: (107)..(107)
<223> OTHER INFORMATION: X = Pro or Tyr
<220> FEATURE:
<221> NAME/KEY: MISC_FEATURE
<222> LOCATION: (108)..(108)
<223> OTHER INFORMATION: X = Asn or Phe

<400> SEQUENCE: 211

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gln Trp Xaa Xaa Xaa Xaa Xaa Xaa Xaa Asp Tyr Trp Gly
                100                 105                 110

Gln Gly Thr Leu Val Thr Val Ser
        115                 120

<210> SEQ ID NO 212
<211> LENGTH: 118
<212> TYPE: PRT
<213> ORGANISM: Homo sapiens

<400> SEQUENCE: 212

Glu Val Gln Leu Val Gln Ser Gly Ala Glu Val Lys Lys Pro Gly Glu
1               5                   10                  15
```

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Trp Leu Val Tyr Phe Asp Tyr Trp Gly Gln Gly Thr
            100                 105                 110

Leu Val Thr Val Ser Ser
            115

<210> SEQ ID NO 213
<211> LENGTH: 120
<212> TYPE: PRT
<213> ORGANISM: Homo sapiens

<400> SEQUENCE: 213

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Trp Leu Gly Gly Asp Tyr Phe Asp Tyr Trp Gly Gln
            100                 105                 110

Gly Thr Leu Val Thr Val Ser Ser
            115                 120

<210> SEQ ID NO 214
<211> LENGTH: 120
<212> TYPE: PRT
<213> ORGANISM: Homo sapiens

<400> SEQUENCE: 214

Glu Val Gln Leu Gln Glu Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly Val Val Thr Ile Ser Ser Asp Lys Ser Ile Ser Ser Ala Tyr
65                  70                  75                  80

Leu Gln Trp Ser Ser Leu Lys Ala Ser Asp Thr Ala Met Tyr Tyr Cys
                85                  90                  95

```
Ala Arg Arg Gln Trp Leu Ala Leu Gly His Phe Asp Tyr Trp Gly Gln
            100                 105                 110

Gly Thr Leu Val Thr Val Ser Ser
        115                 120

<210> SEQ ID NO 215
<211> LENGTH: 120
<212> TYPE: PRT
<213> ORGANISM: Homo sapiens

<400> SEQUENCE: 215

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Trp Phe Gly Val Tyr Tyr Phe Asp Tyr Trp Gly Gln
            100                 105                 110

Gly Thr Leu Val Thr Val Ser Ser
        115                 120

<210> SEQ ID NO 216
<211> LENGTH: 120
<212> TYPE: PRT
<213> ORGANISM: Homo sapiens

<400> SEQUENCE: 216

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Trp Leu Val Leu Pro Tyr Phe Asp Tyr Trp Gly Gln
            100                 105                 110

Gly Thr Leu Val Thr Val Ser Ser
        115                 120

<210> SEQ ID NO 217
<211> LENGTH: 120
<212> TYPE: PRT
<213> ORGANISM: Homo sapiens

<400> SEQUENCE: 217

Glu Val Gln Leu Val Gln Ser Gly Ala Glu Val Lys Lys Pro Gly Glu
```

```
                1               5                   10                  15
Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
            50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Glu Gln Trp Leu Ile Val Thr His Phe Asp Tyr Trp Gly Gln
            100                 105                 110

Gly Thr Leu Val Thr Val Ser Ser
            115                 120
```

<210> SEQ ID NO 218
<211> LENGTH: 113
<212> TYPE: PRT
<213> ORGANISM: Homo sapiens

<400> SEQUENCE: 218

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
            50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg Gln Gln Trp Leu Val Leu Asp Tyr Phe Asp Tyr Trp Gly Gln
            100                 105                 110

Gly
```

<210> SEQ ID NO 219
<211> LENGTH: 119
<212> TYPE: PRT
<213> ORGANISM: Homo sapiens

<400> SEQUENCE: 219

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
            50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95
```

Ala Arg Glu Gln Trp Leu Leu Ser Asn Phe Asp Tyr Trp Gly Gln Gly
            100                 105                 110

Thr Leu Val Thr Val Ser Ser
        115

<210> SEQ ID NO 220
<211> LENGTH: 120
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (105)..(105)
<223> OTHER INFORMATION: X = Ser, Asp, Thr, Pro, Tyr or Gly

<400> SEQUENCE: 220

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gln Trp Leu Val Leu Xaa Tyr Phe Asp Tyr Trp Gly Gln
            100                 105                 110

Gly Thr Leu Val Thr Val Ser Ser
        115                 120

<210> SEQ ID NO 221
<211> LENGTH: 109
<212> TYPE: PRT
<213> ORGANISM: Homo sapiens

<400> SEQUENCE: 221

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Pro Thr Phe Gly Gln Gly Thr Lys Val Glu Ile Lys
            100                 105

<210> SEQ ID NO 222
<211> LENGTH: 109
<212> TYPE: PRT
<213> ORGANISM: Homo sapiens

<400> SEQUENCE: 222

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Pro Thr Phe Gly Gly Gly Thr Lys Val Glu Ile Lys
            100                 105
```

<210> SEQ ID NO 223
<211> LENGTH: 109
<212> TYPE: PRT
<213> ORGANISM: Homo sapiens

<400> SEQUENCE: 223

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Pro Thr Phe Gly Gln Gly Thr Lys Leu Glu Ile Lys
            100                 105
```

<210> SEQ ID NO 224
<211> LENGTH: 107
<212> TYPE: PRT
<213> ORGANISM: Homo sapiens

<400> SEQUENCE: 224

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95
```

Thr Phe Gly Gly Gly Thr Lys Val Asp Ile Lys
            100                 105

<210> SEQ ID NO 225
<211> LENGTH: 107
<212> TYPE: PRT
<213> ORGANISM: Homo sapiens

<400> SEQUENCE: 225

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gly Gly Lys Val Asp Ile Lys
            100                 105

<210> SEQ ID NO 226
<211> LENGTH: 110
<212> TYPE: PRT
<213> ORGANISM: Homo sapiens

<400> SEQUENCE: 226

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 227
<211> LENGTH: 110
<212> TYPE: PRT
<213> ORGANISM: Homo sapiens

<400> SEQUENCE: 227

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser

```
                50                  55                  60
Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Arg Val Phe Gly Gly Gly Thr Lys Leu Thr Val Leu
                100                 105                 110

<210> SEQ ID NO 228
<211> LENGTH: 109
<212> TYPE: PRT
<213> ORGANISM: Homo sapiens

<400> SEQUENCE: 228

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
                 35                  40                  45

Ile Tyr Ser Asn Asn Gln Arg Pro Ser Gly Val Pro Asp Arg Phe Ser
             50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Phe Phe Gly Gly Gly Thr Lys Leu Thr Val Leu
                100                 105

<210> SEQ ID NO 229
<211> LENGTH: 110
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (99)..(99)
<223> OTHER INFORMATION: X = Arg or Pro
<220> FEATURE:
<221> NAME/KEY: MISC_FEATURE
<222> LOCATION: (100)..(100)
<223> OTHER INFORMATION: X = Val or Phe

<400> SEQUENCE: 229

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
                 35                  40                  45

Ile Tyr Ser Asn Asn Gln Arg Pro Ser Gly Val Pro Asp Arg Phe Ser
             50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Xaa Xaa Phe Gly Gly Gly Thr Lys Leu Thr Val Leu
                100                 105                 110
```

<210> SEQ ID NO 230
<211> LENGTH: 113
<212> TYPE: PRT
<213> ORGANISM: Homo sapiens

<400> SEQUENCE: 230

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Tyr Thr Phe Gly Gln Gly Thr Lys Leu Glu Leu
                100                 105                 110

Lys

<210> SEQ ID NO 231
<211> LENGTH: 113
<212> TYPE: PRT
<213> ORGANISM: Homo sapiens

<400> SEQUENCE: 231

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gly
                85                  90                  95

Thr His Trp Pro Pro Tyr Thr Phe Gly Gln Gly Thr Lys Leu Glu Leu
                100                 105                 110

Lys

<210> SEQ ID NO 232
<211> LENGTH: 112
<212> TYPE: PRT
<213> ORGANISM: Homo sapiens

<400> SEQUENCE: 232

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asp Gly Asn Thr Tyr Leu Leu Trp Phe Leu Gln Arg Pro Gly Gln Ser
        35                  40                  45

```
Pro Arg Arg Leu Leu Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Leu Lys
            100                 105                 110
```

<210> SEQ ID NO 233
<211> LENGTH: 108
<212> TYPE: PRT
<213> ORGANISM: Homo sapiens

<400> SEQUENCE: 233

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105
```

<210> SEQ ID NO 234
<211> LENGTH: 109
<212> TYPE: PRT
<213> ORGANISM: Homo sapiens

<400> SEQUENCE: 234

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Trp Thr Phe Gly Gln Gly Thr Lys Val Glu Ile Lys
            100                 105
```

<210> SEQ ID NO 235
<211> LENGTH: 108
<212> TYPE: PRT
<213> ORGANISM: Homo sapiens

<400> SEQUENCE: 235

Asp Ile Gln Met Thr Gln Ser Pro Ser Ser Leu Ser Ala Ser Val Gly

```
                1               5                  10                 15
Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
 65                 70                 75                 80

Glu Asp Phe Ala Thr Tyr Tyr Cys Gln Gln Ser Tyr Ser Thr Pro Pro
                85                 90                 95

Lys Thr Phe Gly Gln Gly Thr Lys Leu Glu Ile Lys
                100                105

<210> SEQ ID NO 236
<211> LENGTH: 108
<212> TYPE: PRT
<213> ORGANISM: Homo sapiens

<400> SEQUENCE: 236

Asp Ile Gln Met Thr Gln Ser Pro Ser Ser Leu Ser Ala Ser Val Gly
 1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
 65                 70                 75                 80

Glu Asp Phe Ala Thr Tyr Tyr Cys Gln Gln Ser Tyr Ser Thr Pro Pro
                85                 90                 95

Tyr Thr Phe Gly Gln Gly Thr Lys Leu Glu Ile Lys
                100                105

<210> SEQ ID NO 237
<211> LENGTH: 108
<212> TYPE: PRT
<213> ORGANISM: Homo sapiens

<400> SEQUENCE: 237

Asp Ile Gln Met Thr Gln Ser Pro Ser Ser Leu Ser Ala Ser Val Gly
 1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
 65                 70                 75                 80

Glu Asp Phe Ala Thr Tyr Tyr Cys Gln Gln Ser Tyr Ser Pro Pro
                85                 90                 95

Tyr Thr Phe Gly Gln Gly Thr Lys Leu Glu Ile Lys
                100                105
```

```
<210> SEQ ID NO 238
<211> LENGTH: 107
<212> TYPE: PRT
<213> ORGANISM: Homo sapiens

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 239
<211> LENGTH: 108
<212> TYPE: PRT
<213> ORGANISM: Homo sapiens

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Arg Thr Phe Gly Gln Gly Thr Lys Leu Glu Ile Lys
            100                 105

<210> SEQ ID NO 240
<211> LENGTH: 8
<212> TYPE: PRT
<213> ORGANISM: Homo sapiens

<400> SEQUENCE: 240

Gln Gln Tyr Gly Ser Ser Pro Pro
1               5

<210> SEQ ID NO 241
<211> LENGTH: 23
<212> TYPE: DNA
<213> ORGANISM: Homo sapiens

<400> SEQUENCE: 241
cagcagtatg gtagctcacc tcc                                       23
```

-continued

<210> SEQ ID NO 242
<211> LENGTH: 4
<212> TYPE: PRT
<213> ORGANISM: Homo sapiens

<400> SEQUENCE: 242

Trp Thr Phe Gly
1

<210> SEQ ID NO 243
<211> LENGTH: 13
<212> TYPE: DNA
<213> ORGANISM: Homo sapiens

<400> SEQUENCE: 243
gtggacgttc ggc                                                          13

<210> SEQ ID NO 244
<211> LENGTH: 22
<212> TYPE: PRT
<213> ORGANISM: Homo sapiens

<400> SEQUENCE: 244

Cys Ala Arg Gly Gly Pro Tyr Asp Tyr Val Trp Gly Ser Tyr Arg Pro
1               5                   10                  15

Asn Asp Ala Phe Asp Ile
            20

<210> SEQ ID NO 245
<211> LENGTH: 66
<212> TYPE: DNA
<213> ORGANISM: Homo sapiens

<400> SEQUENCE: 245
tgtgcgagag gagggcctta tgattacgtt tggggagtt atcgtccgaa cgatgctttt        60
gatatc                                                                  66

<210> SEQ ID NO 246
<211> LENGTH: 10
<212> TYPE: PRT
<213> ORGANISM: Homo sapiens

<400> SEQUENCE: 246

Gln Gln Tyr Gly Ser Ser Pro Thr Phe Gly
1               5                   10

<210> SEQ ID NO 247
<211> LENGTH: 30
<212> TYPE: DNA
<213> ORGANISM: Homo sapiens

<400> SEQUENCE: 247
cagcagtatg gtagctcacc gacgttcggc                                        30

<210> SEQ ID NO 248
<211> LENGTH: 11
<212> TYPE: PRT
<213> ORGANISM: Homo sapiens

<400> SEQUENCE: 248

Gln Gln Tyr Gly Ser Ser Pro Gly Thr Phe Gly
1               5                   10

-continued

<210> SEQ ID NO 249
<211> LENGTH: 33
<212> TYPE: DNA
<213> ORGANISM: Homo sapiens

<400> SEQUENCE: 249
cagcagtatg gtagctcacc tggcacgttc ggc                                    33

<210> SEQ ID NO 250
<211> LENGTH: 11
<212> TYPE: PRT
<213> ORGANISM: Homo sapiens

<400> SEQUENCE: 250

Gln Gln Tyr Gly Ser Ser Pro Pro Thr Phe Gly
1               5                   10

<210> SEQ ID NO 251
<211> LENGTH: 33
<212> TYPE: DNA
<213> ORGANISM: Homo sapiens

<400> SEQUENCE: 251
cagcagtatg gtagctcacc tccgacgttc ggc                                    33

<210> SEQ ID NO 252
<211> LENGTH: 9
<212> TYPE: PRT
<213> ORGANISM: Homo sapiens

<400> SEQUENCE: 252

Asp Ile Val Val Val Pro Ala Ala Ile
1               5

<210> SEQ ID NO 253
<211> LENGTH: 31
<212> TYPE: DNA
<213> ORGANISM: Homo sapiens

<400> SEQUENCE: 253
aggatattgt agtagtacca gctgctatac c                                      31

<210> SEQ ID NO 254
<211> LENGTH: 8
<212> TYPE: PRT
<213> ORGANISM: Homo sapiens

<400> SEQUENCE: 254

Gln Gln Arg Ser Asn Trp Pro Pro
1               5

<210> SEQ ID NO 255
<211> LENGTH: 23
<212> TYPE: DNA
<213> ORGANISM: Homo sapiens

<400> SEQUENCE: 255
cagcagcgta gcaactggcc tcc                                               23

<210> SEQ ID NO 256
<211> LENGTH: 6
<212> TYPE: PRT
<213> ORGANISM: Homo sapiens

<400> SEQUENCE: 256

Phe Thr Phe Gly Pro Gly
1               5

<210> SEQ ID NO 257
<211> LENGTH: 19
<212> TYPE: DNA
<213> ORGANISM: Homo sapiens

<400> SEQUENCE: 257
attcactttc ggccctggg                                              19

<210> SEQ ID NO 258
<211> LENGTH: 17
<212> TYPE: PRT
<213> ORGANISM: Homo sapiens

<400> SEQUENCE: 258

Cys Ala Arg Gly Gly Asp Ile Val Val Val Pro Ala Ala Met Ser Tyr
1               5                   10                  15

Tyr

<210> SEQ ID NO 259
<211> LENGTH: 48
<212> TYPE: DNA
<213> ORGANISM: Homo sapiens

<400> SEQUENCE: 259
tgtgcgagag ggggcgatat tgtagtacca gctgctatgt cctactac              48

<210> SEQ ID NO 260
<211> LENGTH: 17
<212> TYPE: PRT
<213> ORGANISM: Homo sapiens

<400> SEQUENCE: 260

Cys Ala Arg Gly Ala Asp Ile Val Val Val Pro Ala Ala Met Gly Tyr
1               5                   10                  15

Tyr

<210> SEQ ID NO 261
<211> LENGTH: 17
<212> TYPE: PRT
<213> ORGANISM: Homo sapiens

<400> SEQUENCE: 261

Cys Ala Arg Gly Gly Asp Ile Val Val Val Pro Ala Ala Met Arg Tyr
1               5                   10                  15

Tyr

<210> SEQ ID NO 262
<211> LENGTH: 48
<212> TYPE: DNA
<213> ORGANISM: Homo sapiens

<400> SEQUENCE: 262
tgtgcgagag gcggggatat tgtagtacca gctgctatgt gatactac              48

<210> SEQ ID NO 263
<211> LENGTH: 10
<212> TYPE: PRT
<213> ORGANISM: Homo sapiens

```
<400> SEQUENCE: 263

Gln Gln Arg Ser Asn Gly Pro Pro Pro Gly
1               5                   10

<210> SEQ ID NO 264
<211> LENGTH: 30
<212> TYPE: DNA
<213> ORGANISM: Homo sapiens

<400> SEQUENCE: 264
cagcagcgta gcaacgggcc tccccctggg                                    30

<210> SEQ ID NO 265
<211> LENGTH: 8
<212> TYPE: PRT
<213> ORGANISM: Homo sapiens

<400> SEQUENCE: 265

Trp Asp Asp Ser Leu Asn Gly Pro
1               5

<210> SEQ ID NO 266
<211> LENGTH: 23
<212> TYPE: DNA
<213> ORGANISM: Homo sapiens

<400> SEQUENCE: 266
tgggatgaca gcctgaatgg tcc                                           23

<210> SEQ ID NO 267
<211> LENGTH: 4
<212> TYPE: PRT
<213> ORGANISM: Homo sapiens

<400> SEQUENCE: 267

Tyr Val Phe Gly
1

<210> SEQ ID NO 268
<211> LENGTH: 13
<212> TYPE: DNA
<213> ORGANISM: Homo sapiens

<400> SEQUENCE: 268
ttgggtgttc ggc                                                      13

<210> SEQ ID NO 269
<211> LENGTH: 15
<212> TYPE: PRT
<213> ORGANISM: Homo sapiens

<400> SEQUENCE: 269

Cys Ala Arg Ala Met Val Gln Gly Val Ile Gln Thr Tyr Tyr Tyr
1               5                   10                  15

<210> SEQ ID NO 270
<211> LENGTH: 45
<212> TYPE: DNA
<213> ORGANISM: Homo sapiens

<400> SEQUENCE: 270
tgtgcgagag ctatggttca gggagttatc caaacatact actac                   45
```

```
<210> SEQ ID NO 271
<211> LENGTH: 15
<212> TYPE: PRT
<213> ORGANISM: Homo sapiens

<400> SEQUENCE: 271

Cys Ala Arg Ala Met Val Arg Gly Val Ile Thr Tyr Tyr Tyr Tyr
1               5                   10                  15

<210> SEQ ID NO 272
<211> LENGTH: 45
<212> TYPE: DNA
<213> ORGANISM: Homo sapiens

<400> SEQUENCE: 272
tgtgcgaggg ctatggttcg gggagttatt acttattact actac           45

<210> SEQ ID NO 273
<211> LENGTH: 15
<212> TYPE: PRT
<213> ORGANISM: Homo sapiens

<400> SEQUENCE: 273

Cys Ala Arg Gly Met Val Arg Gly Val Ile Thr Tyr Tyr Tyr Tyr
1               5                   10                  15

<210> SEQ ID NO 274
<211> LENGTH: 45
<212> TYPE: DNA
<213> ORGANISM: Homo sapiens

<400> SEQUENCE: 274
tgtgcgagag gtatggttcg gggagttatt acctattact actac           45

<210> SEQ ID NO 275
<211> LENGTH: 11
<212> TYPE: PRT
<213> ORGANISM: Homo sapiens

<400> SEQUENCE: 275

Trp Asp Asp Ser Leu Asn Gly Arg Val Phe Gly
1               5                   10

<210> SEQ ID NO 276
<211> LENGTH: 33
<212> TYPE: DNA
<213> ORGANISM: Homo sapiens

<400> SEQUENCE: 276
tgggatgaca gcctgaatgg tcgggtgttc ggc                 33

<210> SEQ ID NO 277
<211> LENGTH: 10
<212> TYPE: PRT
<213> ORGANISM: Homo sapiens

<400> SEQUENCE: 277

Trp Asp Asp Ser Leu Asn Gly Phe Phe Gly
1               5                   10

<210> SEQ ID NO 278
<211> LENGTH: 30
<212> TYPE: DNA
<213> ORGANISM: Homo sapiens
```

```
<400> SEQUENCE: 278
tgggatgaca gcctgaatgg tttcttcggc                                        30

<210> SEQ ID NO 279
<211> LENGTH: 8
<212> TYPE: PRT
<213> ORGANISM: Homo sapiens

<400> SEQUENCE: 279

Met Gln Gly Thr His Trp Pro Pro
1               5

<210> SEQ ID NO 280
<211> LENGTH: 23
<212> TYPE: DNA
<213> ORGANISM: Homo sapiens

<400> SEQUENCE: 280
atgcaaggta cacactggcc tcc                                               23

<210> SEQ ID NO 281
<211> LENGTH: 4
<212> TYPE: PRT
<213> ORGANISM: Homo sapiens

<400> SEQUENCE: 281

Trp Thr Phe Gly
1

<210> SEQ ID NO 282
<211> LENGTH: 13
<212> TYPE: DNA
<213> ORGANISM: Homo sapiens

<400> SEQUENCE: 282
gtggacgttc ggc                                                          13

<210> SEQ ID NO 283
<211> LENGTH: 12
<212> TYPE: PRT
<213> ORGANISM: Homo sapiens

<400> SEQUENCE: 283

Met Gln Gly Thr His Trp Pro Pro Trp Thr Phe Gly
1               5                   10

<210> SEQ ID NO 284
<211> LENGTH: 36
<212> TYPE: DNA
<213> ORGANISM: Homo sapiens

<400> SEQUENCE: 284
atgcaaggta cacactggcc cccgtggacg ttcggc                                 36

<210> SEQ ID NO 285
<211> LENGTH: 11
<212> TYPE: PRT
<213> ORGANISM: Homo sapiens

<400> SEQUENCE: 285

Met Gln Gly Thr His Trp Pro Trp Thr Phe Gly
1               5                   10
```

```
<210> SEQ ID NO 286
<211> LENGTH: 33
<212> TYPE: DNA
<213> ORGANISM: Homo sapiens

<400> SEQUENCE: 286
atgcaaggaa cacattggcc ttggacgttc ggc                                    33

<210> SEQ ID NO 287
<211> LENGTH: 36
<212> TYPE: DNA
<213> ORGANISM: Homo sapiens

<400> SEQUENCE: 287
atgcaaggta cacactggcc tccgtggacg ttcggc                                 36

<210> SEQ ID NO 288
<211> LENGTH: 8
<212> TYPE: PRT
<213> ORGANISM: Homo sapiens

<400> SEQUENCE: 288

Gln Gln Ser Tyr Ser Thr Pro Pro
1               5

<210> SEQ ID NO 289
<211> LENGTH: 23
<212> TYPE: DNA
<213> ORGANISM: Homo sapiens

<400> SEQUENCE: 289
caacagagtt acagtacccc tcc                                               23

<210> SEQ ID NO 290
<211> LENGTH: 13
<212> TYPE: PRT
<213> ORGANISM: Homo sapiens

<400> SEQUENCE: 290

Gln Gln Ser Tyr Ser Thr Pro Pro Thr Trp Thr Phe Gly
1               5                   10

<210> SEQ ID NO 291
<211> LENGTH: 36
<212> TYPE: DNA
<213> ORGANISM: Homo sapiens

<400> SEQUENCE: 291
caacagagtt acagtacccc tccgacgtgg ttcggc                                 36

<210> SEQ ID NO 292
<211> LENGTH: 12
<212> TYPE: PRT
<213> ORGANISM: Homo sapiens

<400> SEQUENCE: 292

Gln Gln Ser Tyr Ser Thr Pro Pro Lys Thr Phe Gly
1               5                   10

<210> SEQ ID NO 293
<211> LENGTH: 36
<212> TYPE: DNA
<213> ORGANISM: Homo sapiens

<400> SEQUENCE: 293
```

```
caacagagtt acagtacccc tccgtagacg ttcggc                        36
```

<210> SEQ ID NO 294
<211> LENGTH: 12
<212> TYPE: PRT
<213> ORGANISM: Homo sapiens

<400> SEQUENCE: 294

Gln Gln Ser Tyr Ser Thr Pro Pro Trp Thr Phe Gly
1               5                   10

<210> SEQ ID NO 295
<211> LENGTH: 36
<212> TYPE: DNA
<213> ORGANISM: Homo sapiens

<400> SEQUENCE: 295

```
caacagagtt acagtacccc tccgtggacg ttcggc                        36
```

<210> SEQ ID NO 296
<211> LENGTH: 36
<212> TYPE: DNA
<213> ORGANISM: Homo sapiens

<400> SEQUENCE: 296

```
caacagagtt acagtacccc cccgtggacg ttcggc                        36
```

<210> SEQ ID NO 297
<211> LENGTH: 12
<212> TYPE: PRT
<213> ORGANISM: Homo sapiens

<400> SEQUENCE: 297

Gln Gln Ser Tyr Ser Ser Pro Pro Trp Thr Phe Gly
1               5                   10

<210> SEQ ID NO 298
<211> LENGTH: 36
<212> TYPE: DNA
<213> ORGANISM: Homo sapiens

<400> SEQUENCE: 298

```
caacagagtt acagtagccc cccgtggacg ttcggc                        36
```

<210> SEQ ID NO 299
<211> LENGTH: 12
<212> TYPE: PRT
<213> ORGANISM: Homo sapiens

<400> SEQUENCE: 299

Gln Gln Ser Tyr Ser Thr Pro Pro Arg Thr Phe Gly
1               5                   10

<210> SEQ ID NO 300
<211> LENGTH: 36
<212> TYPE: DNA
<213> ORGANISM: Homo sapiens

<400> SEQUENCE: 300

```
caacagagtt acagtacccc tccgaggacg ttcggc                        36
```